United States Patent
Al-Ali et al.

(10) Patent No.: US 11,986,067 B2
(45) Date of Patent: May 21, 2024

(54) STRAP FOR A WEARABLE DEVICE

(71) Applicant: Masimo Corporation, Irvine, CA (US)

(72) Inventors: Ammar Al-Ali, San Juan Capistrano, CA (US); Chad A. DeJong, Los Angeles, CA (US); Stephen Scruggs, Newport Beach, CA (US)

(73) Assignee: Masimo Corporation, Irvine, CA (US)

( * ) Notice: Subject to any disclaimer, the term of this patent is extended or adjusted under 35 U.S.C. 154(b) by 458 days.

(21) Appl. No.: 17/404,838

(22) Filed: Aug. 17, 2021

(65) Prior Publication Data

US 2022/0053892 A1    Feb. 24, 2022

Related U.S. Application Data

(60) Provisional application No. 63/068,256, filed on Aug. 20, 2020, provisional application No. 63/067,622, filed on Aug. 19, 2020.

(51) Int. Cl.
*A44C 5/02* (2006.01)
*A44C 5/00* (2006.01)
*A44C 5/10* (2006.01)

(52) U.S. Cl.
CPC ............ *A44C 5/107* (2013.01); *A44C 5/0061* (2013.01)

(58) Field of Classification Search
CPC ..... A44C 5/107; A44C 5/0061; A44C 5/0053; A44C 5/02; A44C 5/025
See application file for complete search history.

(56) References Cited

U.S. PATENT DOCUMENTS 1,750,125 A * 3/1930 Prestinari ................. A44C 5/02
  63/3
1,817,475 A   8/1931 Becker
(Continued)

FOREIGN PATENT DOCUMENTS

CA    2 454 130    2/2003
CN    1190337      8/1998
(Continued)

OTHER PUBLICATIONS

AIVAnet, "Garmin Vivofit Jr Release Date, Price and Specs—CNET", Sep. 29, 2016, https://blog.aivanet.com/2016/09/29/garmin-vivofit-jr-release-date-price-and-specs-cnet/ in 3 pages.

(Continued)

*Primary Examiner* — Jack W Lavinder
(74) *Attorney, Agent, or Firm* — Knobbe, Martens, Olson & Bear, LLP

(57) ABSTRACT

A strap for a wearable device configured to secure to a portion of a body of a user can include a base and a plurality of strap members secured to portions of the base. In some implementations, the base is made of a first material and each of the plurality of strap members are made of a second material, the first material being more pliable than the second material. In some implementations, the base includes a plurality of openings spaced from one another along a length of the base and a plurality of stems. In some implementations, each of the plurality of strap members is a channel secured to one of the stems. In some implementations, the first material includes at least one of rubber and silicone and the second material is a metallic material.

20 Claims, 27 Drawing Sheets

(56) References Cited

U.S. PATENT DOCUMENTS

| | | | |
|---|---|---|---|
| 1,898,402 A | 2/1933 | Smith | |
| 2,505,044 A | 4/1950 | Heinrich | |
| 3,747,171 A | 7/1973 | Montague, Jr. | |
| 4,059,267 A | 11/1977 | Noble | |
| 4,197,618 A | 4/1980 | Bourguignon | |
| 4,249,267 A | 2/1981 | Voss | |
| 4,266,400 A * | 5/1981 | Tabata | B21L 11/005 224/179 |
| 4,447,238 A | 5/1984 | Eldridge, Jr. | |
| 4,847,820 A | 7/1989 | Thinesen et al. | |
| 4,941,236 A | 7/1990 | Sherman et al. | |
| 4,960,128 A | 10/1990 | Gordon et al. | |
| 4,964,408 A | 10/1990 | Hink et al. | |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| 5,436,499 A | 7/1995 | Namavar et al. | |
| D361,840 S | 8/1995 | Savage et al. | |
| D362,063 S | 9/1995 | Savage et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,494,043 A | 2/1996 | O'Sullivan et al. | |
| 5,533,511 A | 7/1996 | Kaspari et al. | |
| 5,561,275 A | 10/1996 | Savage et al. | |
| 5,590,649 A | 1/1997 | Caro et al. | |
| 5,602,924 A | 2/1997 | Durand et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,671,914 A | 9/1997 | Kalkhoran et al. | |
| 5,726,440 A | 3/1998 | Kalkhoran et al. | |
| D393,830 S | 4/1998 | Tobler et al. | |
| 5,743,262 A | 4/1998 | Lepper, Jr. et al. | |
| 5,747,806 A | 5/1998 | Khalil et al. | |
| 5,750,994 A | 5/1998 | Schlager | |
| 5,758,644 A | 6/1998 | Diab et al. | |
| 5,760,910 A | 6/1998 | Lepper, Jr. et al. | |
| D407,342 S | 3/1999 | Ishizaka | |
| D408,314 S | 4/1999 | Kojima et al. | |
| 5,890,929 A | 4/1999 | Mills et al. | |
| 5,919,134 A | 7/1999 | Diab | |
| 5,987,343 A | 11/1999 | Kinast | |
| 5,997,343 A | 12/1999 | Mills et al. | |
| 6,002,952 A | 12/1999 | Diab et al. | |
| 6,010,937 A | 1/2000 | Karam et al. | |
| 6,027,452 A | 2/2000 | Flaherty et al. | |
| 6,040,578 A | 3/2000 | Malin et al. | |
| 6,066,204 A | 5/2000 | Haven | |
| 6,088,607 A | 7/2000 | Diab et al. | |
| 6,115,673 A | 9/2000 | Malin et al. | |
| 6,124,597 A | 9/2000 | Shehada et al. | |
| 6,128,521 A | 10/2000 | Marro et al. | |
| 6,129,675 A | 10/2000 | Jay | |
| 6,144,868 A | 11/2000 | Parker | |
| 6,152,754 A | 11/2000 | Gerhardt et al. | |
| 6,184,521 B1 | 2/2001 | Coffin, IV et al. | |
| 6,232,609 B1 | 5/2001 | Snyder et al. | |
| 6,241,683 B1 | 6/2001 | Macklem et al. | |
| 6,253,097 B1 | 6/2001 | Aronow et al. | |
| 6,255,708 B1 | 7/2001 | Sudharsanan et al. | |
| 6,280,381 B1 | 8/2001 | Malin et al. | |
| 6,285,896 B1 | 9/2001 | Tobler et al. | |
| 6,301,754 B1 | 10/2001 | Grunberger et al. | |
| 6,308,089 B1 | 10/2001 | von der Ruhr et al. | |
| 6,317,627 B1 | 11/2001 | Ennen et al. | |
| 6,321,100 B1 | 11/2001 | Parker | |
| 6,334,065 B1 | 12/2001 | Al-Ali et al. | |
| 6,360,114 B1 | 3/2002 | Diab et al. | |
| 6,368,283 B1 | 4/2002 | Xu et al. | |
| 6,408,491 B2 | 6/2002 | Guyard | |
| 6,411,373 B1 | 6/2002 | Garside et al. | |
| 6,415,167 B1 | 7/2002 | Blank et al. | |
| 6,430,437 B1 | 8/2002 | Marro | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,487,429 B2 | 11/2002 | Hockersmith et al. | |
| 6,505,059 B1 | 1/2003 | Kollias et al. | |
| 6,525,386 B1 | 2/2003 | Mills et al. | |
| 6,526,300 B1 | 2/2003 | Kiani et al. | |
| 6,534,012 B1 | 3/2003 | Hazen et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,587,196 B1 | 7/2003 | Stippick et al. | |
| 6,587,199 B1 | 7/2003 | Luu | |
| 6,595,316 B2 | 7/2003 | Cybulski et al. | |
| 6,597,932 B2 | 7/2003 | Tian et al. | |
| 6,606,511 B1 | 8/2003 | Ali et al. | |
| 6,635,559 B2 | 10/2003 | Greenwald et al. | |
| 6,639,668 B1 | 10/2003 | Trepagnier | |
| 6,640,116 B2 | 10/2003 | Diab | |
| 6,640,117 B2 | 10/2003 | Makarewicz et al. | |
| 6,647,597 B2 | 11/2003 | Reiter | |
| 6,650,917 B2 | 11/2003 | Diab et al. | |
| 6,658,276 B2 | 12/2003 | Kiani et al. | |
| 6,661,161 B1 | 12/2003 | Lanzo et al. | |
| 6,697,656 B1 | 2/2004 | Al-Ali | |
| 6,697,658 B2 | 2/2004 | Al-Ali | |
| RE38,476 E | 3/2004 | Diab et al. | |
| 6,699,194 B1 | 3/2004 | Diab et al. | |
| RE38,492 E | 4/2004 | Diab et al. | |
| 6,738,652 B2 | 5/2004 | Mattu et al. | |
| 6,760,607 B2 | 7/2004 | Al-Ali | |
| 6,788,965 B2 | 9/2004 | Ruchti et al. | |
| 6,816,241 B2 | 11/2004 | Grubisic | |
| 6,822,564 B2 | 11/2004 | Al-Ali | |
| 6,850,787 B2 | 2/2005 | Weber et al. | |
| 6,850,788 B2 | 2/2005 | Al-Ali | |
| 6,876,931 B2 | 4/2005 | Lorenz et al. | |
| 6,880,364 B1 * | 4/2005 | Vidolin | A44C 5/025 40/633 |
| 6,920,345 B2 | 7/2005 | Al-Ali et al. | |
| 6,934,570 B2 | 8/2005 | Kiani et al. | |
| 6,943,348 B1 | 9/2005 | Coffin IV | |
| 6,956,649 B2 | 10/2005 | Acosta et al. | |
| 6,961,598 B2 | 11/2005 | Diab | |
| 6,970,792 B1 | 11/2005 | Diab | |
| 6,985,764 B2 | 1/2006 | Mason et al. | |
| 6,990,364 B2 | 1/2006 | Ruchti et al. | |
| 6,991,364 B2 | 1/2006 | Yang | |
| 6,998,247 B2 | 2/2006 | Monfre et al. | |
| 7,003,338 B2 | 2/2006 | Weber et al. | |
| 7,015,451 B2 | 3/2006 | Dalke et al. | |
| 7,027,849 B2 | 4/2006 | Al-Ali | |
| D522,900 S | 6/2006 | Yamamoto et al. | |
| D526,719 S | 8/2006 | Richie, Jr. et al. | |
| 7,096,052 B2 | 8/2006 | Mason et al. | |
| 7,096,054 B2 | 8/2006 | Abdul-Hafiz et al. | |
| D529,616 S | 10/2006 | Deros et al. | |
| 7,133,710 B2 | 11/2006 | Acosta et al. | |
| 7,142,901 B2 | 11/2006 | Kiani et al. | |
| 7,146,731 B2 | 12/2006 | Kraus et al. | |
| 7,225,006 B2 | 5/2007 | Al-Ali et al. | |
| RE39,672 E | 6/2007 | Shehada et al. | |
| D549,602 S | 8/2007 | Oberrieder et al. | |
| 7,254,429 B2 | 8/2007 | Schurman et al. | |
| 7,254,431 B2 | 8/2007 | Al-Ali et al. | |
| 7,254,434 B2 | 8/2007 | Schulz et al. | |
| 7,274,955 B2 | 9/2007 | Kiani et al. | |
| D554,263 S | 10/2007 | Al-Ali et al. | |
| 7,280,858 B2 | 10/2007 | Al-Ali et al. | |
| 7,289,835 B2 | 10/2007 | Mansfield et al. | |
| 7,292,883 B2 | 11/2007 | De Felice et al. | |
| D560,520 S | 1/2008 | Oberrieder et al. | |
| 7,341,559 B2 | 3/2008 | Schulz et al. | |
| 7,343,186 B2 | 3/2008 | Lamego et al. | |

(56) References Cited

U.S. PATENT DOCUMENTS

| | | |
|---|---|---|
| D566,282 S | 4/2008 | Al-Ali et al. |
| 7,356,365 B2 | 4/2008 | Schurman |
| 7,363,687 B2 | 4/2008 | Kraus et al. |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,640,632 B2 | 1/2010 | Lazarus |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |
| D631,780 S | 2/2011 | Levy |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,029,185 B2 | 10/2011 | Faucher et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,235,585 B2 | 8/2012 | Speichinger |
| 8,255,026 B1 | 8/2012 | Al-Ali |
| 8,261,416 B2 | 9/2012 | Rothbaum et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| 8,316,515 B2 | 11/2012 | Slank |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| D711,760 S | 8/2014 | Savoy |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| D715,668 S | 10/2014 | Roush et al. |
| 8,852,094 B2 | 10/2014 | Al-Ali et al. |
| 8,852,994 B2 | 10/2014 | Wojtczuk et al. |
| 8,893,938 B2 | 11/2014 | Grossenbacher et al. |
| 8,897,847 B2 | 11/2014 | Al-Ali |
| 8,911,377 B2 | 12/2014 | Al-Ali |
| 8,989,831 B2 | 3/2015 | Al-Ali et al. |
| 8,997,318 B2 | 4/2015 | Nicolas et al. |
| 8,998,484 B2 | 4/2015 | Savoy |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |

(56) References Cited

U.S. PATENT DOCUMENTS

| | | |
|---|---|---|
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,585,445 B2 | 3/2017 | Qian et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| D795,731 S | 8/2017 | Bayley et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| D800,594 S | 10/2017 | Lasserre |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,907,345 B2 | 3/2018 | O'Neill |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,098,422 B2 | 10/2018 | Fiedler et al. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,518 B1 | 12/2018 | De Iuliis et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,206,463 B2 | 2/2019 | de Jong |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| D850,317 S | 6/2019 | Hinds et al. |
| 10,327,337 B2 | 6/2019 | Schmidt et al. |
| 10,327,713 B2 | 6/2019 | Barker et al. |
| 10,332,630 B2 | 6/2019 | Al-Ali |
| D854,960 S | 7/2019 | Yu et al. |
| D857,545 S | 8/2019 | Akana et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D862,459 S | 10/2019 | Choplin et al. |
| D863,095 S | 10/2019 | Akana et al. |
| D863,985 S | 10/2019 | Viry |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,119 B1 | 11/2019 | Chambers et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| D874,311 S | 2/2020 | Connor et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,287 S | 6/2020 | Kong |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| D901,492 S | 11/2020 | Gao |
| 10,827,961 B1 | 11/2020 | Iyengar et al. |
| 10,828,007 B1 | 11/2020 | Telfort et al. |
| 10,832,818 B2 | 11/2020 | Muhsin et al. |
| D904,919 S | 12/2020 | Barczak et al. |
| D905,584 S | 12/2020 | Register et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| D912,563 S | 3/2021 | Akana et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| D919,619 S | 5/2021 | Kozlovskaya et al. |
| 11,006,867 B2 | 5/2021 | Ai-Ali |
| D921,202 S | 6/2021 | Al-Ali et al. |
| 11,024,064 B2 | 6/2021 | Muhsin et al. |
| 11,026,604 B2 | 6/2021 | Chen et al. |

(56) References Cited

U.S. PATENT DOCUMENTS

| | | |
|---|---|---|
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D932,321 S | 10/2021 | Jung |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| D939,360 S | 12/2021 | Qu |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,266,349 B2 | 3/2022 | Mizuno et al. |
| 11,272,839 B2 | 3/2022 | Al-Ali et al. |
| 11,289,199 B2 | 3/2022 | Ai-Ali |
| RE49,034 E | 4/2022 | Al-Ali |
| D948,057 S | 4/2022 | Rahman |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D952,499 S | 5/2022 | Akana et al. |
| D957,648 S | 7/2022 | Al-Ali |
| D957,977 S | 7/2022 | Cao |
| 11,382,567 B2 | 7/2022 | O'Brien et al. |
| 11,389,093 B2 | 7/2022 | Triman et al. |
| D959,993 S | 8/2022 | Qin |
| D961,437 S | 8/2022 | Tian |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,769 S | 12/2022 | Yi |
| D971,933 S | 12/2022 | Ahmed |
| D972,431 S | 12/2022 | Huang |
| D973,072 S | 12/2022 | Ahmed |
| D973,532 S | 12/2022 | Zheng |
| D973,685 S | 12/2022 | Ahmed |
| D973,686 S | 12/2022 | Ahmed |
| D974,185 S | 1/2023 | He et al. |
| D974,193 S | 1/2023 | Forrest et al. |
| D975,572 S | 1/2023 | Akana et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 2001/0016971 A1 | 8/2001 | Guyard |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0026170 A1 | 2/2003 | Yang |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2003/0229974 A1 | 12/2003 | Zemer et al. |
| 2004/0106163 A1 | 6/2004 | Workman, Jr. et al. |
| 2005/0055276 A1 | 3/2005 | Kiani et al. |
| 2005/0102802 A1 | 5/2005 | Sitbon et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2007/0073116 A1 | 3/2007 | Kiani et al. |
| 2007/0167106 A1 | 7/2007 | Hoover |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2009/0010110 A1 | 1/2009 | Chariton |
| 2009/0036759 A1 | 2/2009 | Ault et al. |
| 2009/0049667 A1 | 2/2009 | Takahashi |
| 2009/0093687 A1 | 4/2009 | Telfort et al. |
| 2009/0095926 A1 | 4/2009 | MacNeish, III |
| 2009/0113870 A1* | 5/2009 | Rejzner ............... A44C 5/107 59/80 |
| 2009/0182216 A1 | 7/2009 | Roushey, III et al. |
| 2009/0247984 A1 | 10/2009 | Lamego et al. |
| 2009/0275844 A1 | 11/2009 | Al-Ali |
| 2009/0289090 A1 | 11/2009 | Fullerton et al. |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0200627 A1 | 8/2010 | Shen |
| 2010/0234718 A1 | 9/2010 | Sampath et al. |
| 2010/0243688 A1 | 9/2010 | Gutierrez et al. |
| 2010/0270257 A1 | 10/2010 | Wachman et al. |
| 2010/0302914 A1 | 12/2010 | Faucher et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0083254 A1 | 4/2011 | Trutna et al. |
| 2011/0087081 A1 | 4/2011 | Kiani et al. |
| 2011/0099771 A1 | 5/2011 | Grossenbacher et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0230733 A1 | 9/2011 | Al-Ali |
| 2012/0113760 A1 | 5/2012 | Pagrani |
| 2012/0123231 A1 | 5/2012 | O'Reilly |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0074545 A1 | 3/2013 | Moloney |
| 2013/0096405 A1 | 4/2013 | Garfio |
| 2013/0205476 A1 | 8/2013 | Gentile et al. |
| 2013/0235546 A1 | 9/2013 | Sedillo et al. |
| 2013/0296672 A1 | 11/2013 | O'Neil et al. |
| 2013/0326790 A1 | 12/2013 | Cauwels et al. |
| 2013/0345921 A1 | 12/2013 | Al-Ali et al. |
| 2014/0000312 A1 | 1/2014 | Nicolas et al. |
| 2014/0078871 A1 | 3/2014 | Savoy |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0257050 A1 | 9/2014 | Kuroda et al. |

(56) References Cited

U.S. PATENT DOCUMENTS

| | | |
|---|---|---|
| 2014/0275871 A1 | 9/2014 | Lamego et al. |
| 2014/0275872 A1 | 9/2014 | Merritt et al. |
| 2014/0276119 A1 | 9/2014 | Venkatraman et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2016/0026215 A1 | 1/2016 | Armstrong |
| 2016/0066842 A1 | 3/2016 | Kokkoneva et al. |
| 2016/0128209 A1 | 5/2016 | Yoon et al. |
| 2016/0196388 A1 | 7/2016 | Lamego |
| 2016/0283665 A1 | 9/2016 | Sampath et al. |
| 2016/0367173 A1 | 12/2016 | Dalvi et al. |
| 2017/0024748 A1 | 1/2017 | Haider |
| 2017/0086535 A1 | 3/2017 | De Iuliis et al. |
| 2017/0119314 A1 | 5/2017 | Just et al. |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0168293 A1* | 6/2018 | Leiggener ............... A44C 5/107 |
| 2018/0184920 A1 | 7/2018 | Rabinovich et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0310823 A1 | 11/2018 | Al-Ali et al. |
| 2018/0338721 A1 | 11/2018 | Wang et al. |
| 2019/0117070 A1 | 4/2019 | Muhsin et al. |
| 2019/0239787 A1 | 8/2019 | Pauley et al. |
| 2019/0320906 A1 | 10/2019 | Olsen |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0323440 A1 | 10/2020 | Vule et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0181012 A1 | 6/2021 | Simmendinger |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0039707 A1 | 2/2022 | Sharma et al. |
| 2022/0071562 A1 | 3/2022 | Kiani |
| 2022/0096603 A1 | 3/2022 | Kiani et al. |
| 2022/0148724 A1 | 5/2022 | Pasternak et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |

FOREIGN PATENT DOCUMENTS

| | | |
|---|---|---|
| CN | 1309938 | 8/2001 |
| CN | 1221195 | 10/2005 |
| CN | 101836780 | 7/2014 |
| CN | 102854793 | 4/2017 |
| CN | 107106907 A | 8/2017 |
| CN | 103376734 | 9/2017 |
| CN | 107411248 | 12/2017 |
| CN | 206960868 | 2/2018 |
| CN | 105392418 | 5/2018 |
| CN | 108464585 | 8/2018 |
| CN | 107106907 B | 10/2018 |
| CN | 208972735 | 6/2019 |
| EP | 0 198 279 | 10/1986 |
| EP | 0 824 328 | 2/1999 |
| EP | 1 412 840 | 4/2004 |
| EP | 2 098 131 | 9/2009 |
| EP | 2 316 298 A1 | 5/2011 |
| EP | 2 382 890 A2 | 11/2011 |
| EP | 2 316 298 B1 | 5/2012 |
| EP | 2 382 890 B1 | 7/2015 |
| EP | 3 015 948 | 5/2016 |
| FR | 2579426 A1 * | 4/1985 |
| FR | 2 946 159 | 12/2010 |
| GB | 361942 | 11/1931 |
| GB | 2 223 665 | 4/1990 |
| GB | 2 384 162 | 7/2003 |
| IN | 201003219 I4 | 7/2011 |
| JP | 11-300864 | 11/1999 |
| JP | 11-342010 | 12/1999 |
| JP | 11-342011 | 12/1999 |
| JP | 2001-178525 | 7/2001 |
| JP | 2001-272479 | 10/2001 |
| JP | 2004-537802 | 12/2004 |
| JP | 2006-034654 | 2/2006 |
| JP | 3947768 | 4/2007 |
| JP | 2016-045207 | 4/2016 |
| JP | 2016-114600 | 6/2016 |

(56) References Cited

FOREIGN PATENT DOCUMENTS

| | | |
|---|---|---|
| JP | 6182583 | 7/2017 |
| KR | 10-2011-0047163 | 5/2011 |
| KR | 10-2011-0055419 | 5/2011 |
| KR | 10-2016-0088157 | 7/2016 |
| WO | WO 03/012615 | 2/2003 |
| WO | WO 2014/184649 | 11/2014 |
| WO | WO 2020/019192 | 1/2020 |
| WO | WO-2021028840 A1 * | 2/2021 |
| WO | WO 2022/040231 | 2/2022 |
| WO | WO 2023/003980 | 1/2023 |

OTHER PUBLICATIONS

Apollo, "Apollo® Wearable", as archived Oct. 3, 2022, https://web.archive.org/web/20221003190714/https://apolloneuro.com/products/apollo-wearable?variant=41447575945413, pp. 8.

"Batfree, World First Power Strap for Apple Watch", as uploaded Dec. 18, 2018, https://www.youtube.com/watch?v=v38-9wJyBoE, in 1 page.

Comstock, Jonah, "Whoop, a wearable for athletes, raises $12 million", https://www.mobihealthnews.com/46964/whoop-a-wearable-for-athletes-raises-12-million, Sep. 22, 2015, pp. 2.

DC Rainmaker, "Garmin Vivofit Jr. 2: Everything you ever wanted to know", DC Rainmaker, Sep. 27, 2017, https://www.dcrainmaker.com/2017/09/garmin-vivofit-jr-2-review-everything-you-ever-wanted-to-know.html in 52 pages.

Duffy, Jill, "MIO Alpha BLE Review", PC Magazine, Jan. 28, 2013, https://www.pcmag.com/reviews/mio-alpha-ble in 7 pages.

Faust, Erik, "The Togvu Batfree is an Apple Watch band that charges your watch while you wear it", May 1, 2019, https://thegadgeteer.com/2019/05/01/the-togvu-batfree-is-an-apple-watch-band-that-charges-your-watch-while-you-wear-it/ in 4 pages.

Flex Watches, "Black Band", as printed Oct. 4, 2023, https://flexwatches.com/products/black-silicone-replaceable-band?variant=410473941&currency=USD&utm_medium=product_sync&utm_source=google&utm_content=sag_organic&utm_campaign=sag_organic&srsltid=ASuE1wRzDWxvsf2DTXqquBCKplYT15e4vfPv6argqpEJ9yDqBWOS2zjk5zs&com_cvv=a0ca8cf311e059d8bc8090c0d8ed53ef9363e1dc2aeea0d3bd8c43122e608eab in 2 pages.

Flex Watches, "The Black Band", as archived Dec. 29, 2011,|https://web.archive.org/web/20111229082626/http:/flexwatches.com/store/the-black-band.html in 2 pages.

Gadgetsin, "Batfree Apple Watch Power Strap with Built-in Batteries", Mar. 16, 2019, https://gadgetsin.com/batfree-apple-watch-power-strap-with-built-in-batteries.htm in 5 pages.

Garmin Vivofit Jr. 3, Fitness Tracker for Kids, Includes Interactive App Experience, Swim-Friendly, Up To 1-year Battery Life, Blue Stars, Date first available: Oct. 15, 2020, as archived Oct. 4, 2023, https://web.archive.org/web/20231004210347/https://www.amazon.com/Garmin-Interactive-Experience-Swim-Friendly-010-02441-22/dp/B08JWZ5WY2/ref=sr_1_2?keywords=garmin%2Bvivofit%2Bjr%2B3&qid=1689620317&sr=8-2&th=1 in 4 pages.

Garmin, Blue Stars Band, Accessory Band for Vivofit® Jr. 3, Date first available: Oct. 15, 2020, as printed Oct. 4, 2023, https://web.archive.org/web/20231004204515/https://www.garmin.com/en-us/p/742671 in 3 pages.

Garmin Vivofit Jr. 3: Accessory Band, Disney The Little Mermaid, Date first available: Apr. 26, 2021, as archived Oct. 4, 2023, https://web.archive.org/web/20231004203105/https://www.amazon.com/Garmin-Vivofit-Accessory-Mermaid-010-12666-43/dp/B093JR6LD7/ref=asc_df_B093JR6LD7/?tag=hyprod-20&linkCode=df0&hvadid=649684855167&hvpos=&hvnetw=g&hvrand=6991608940390168035&hvpone=&hvptwo=&hvqmt=&hvdev=c&hvdvcmdl=&hvlocint=&hvlocphy=9031529&hvtargid=pla-1679549217739&psc=1 in 3 pages.

Iiteeology, Compatible with Apple Watch Band 44mm SE/Series 6 5 4, Upgraded Stainless Steel Link Replacement Band with iWatch Screen Protector Case Silver/Silver, Date first available: Jul. 10, 2020, as printed Oct. 4, 2023, https://www.amazon.com/iiteeology-Compatible-Stainless-Replacement-Protector/dp/B08CRSLF4V?th=1 in 7 pages.

International Search Report and Written Opinion as received in PCT Application No. PCT/US2021/046369, dated Nov. 25, 2021 in 15 pages.

International Search Report and Written Opinion as received in PCT Application No. PCT/US2022/037764, dated Sep. 23, 2022 in 15 pages.

JXVM for Apple Watch Band 45mm 44mm 42mm 41mm 40mm 38mm with Case, Uni-body Protective Bumper Band, Crystal Clear Sporty Case, with Adjustable Strap for iWatch Ultra & Series 9 8 7 6 5 4 3 2 1 / SE, Date first available: Jun. 3, 2023, as archived Oct. 4, 2023, https://web.archive.org/web/20231004232401/https://www.amazon.com/dp/B096TLY3QT/ref=sspa_dk_detail_1?pd_rd_i=B096TLY3QT&pd_rd_w=DHOjE&content-id=amzn1.sym.386c274b-4bfe-4421-9052-a1a56db557ab&pf_rd_p=386c274b-4bfe-4421-9052-a1a56db557ab&pf_rd_r=18BQQRTPDVFBCCVA1WE2&pd_rd_wg=jYoke&pd_rd_r=c500a4bf-770c-46aa-9e76-ba98c1a39918&s=apparel&sp_csd=d2lkZ2V0TmFtZT1zcF9kZXRhaWxfdGhlbWF0aWM&spLa=ZW5jcnlwdGVkUXVhbGlmaWVyPUFSSFFRMVpaWkNQM0ImZW5jcnlwdGVkSWQ9QTAxOTMyNDExOEc1RkdLRKNRSUVNJmVuY3J5cHRIRIZEFKSWQ9QTA5MDY2NDQxS05ZODNOUkQxSUNBJndpZGdldE5hbWU9c3BfZGVOYWlsX3RoZW1lhdGljJmFjdGlvbj1jbGlja1JIZGlyZWN0JmRvTm90TG9nQ2xpY2s9dHJ1ZQ&th=1&psc=1 in 5 pages.

"Magnetic Milanese Stainless Steel Strap Band And Frame for Apple Watch Series 42mm—Silver", iSank, Date first available: Jun. 28, 2021, as printed Oct. 4, 2023, https://www.amazon.eg/-/en/Magnetic-Milanese-Stainless-Steel-Silver/dp/B09841V2KX in 3 pages.

"M5 Band Sport Silicone Wrist Strap (M5/M6), For Office", as printed Nov. 2, 2023, https://www.indiamart.com/proddetail/m5-band-sport-silicone-wrist-strap-m5-m6-23772599055.html, pp. 5.

O'Kane, Sean, "Whoop's New Fitness Tracker is Better Thanks to a Battery Breakthrough", The Verge, Sep. 8, 2021, https://www.theverge.com/2021/9/8/22662979/whoop-fitness-tracker-sila-silicon-anode-battery-electric-cars, pp. 4.

Proatl Compatible with Apple Watch Bands Series SE 8 7 6 5 4 3 2 1, Women& Men Sport Clear Soft Silicone Strap with Bumper Protective Cases for Apple Watch Series 45mm 44mm 42mm 41mm 40mm 38mm, Date first available: May 18, 2021, as archived Oct. 4, 2023, https://web.archive.org/web/20231004215422/https://www.amazon.com/dp/B0957P42R5?asc_source=verso&asc_campaign=6220f63a9621fbc9faf148e3%7Cc53mEFfLxx2tam8KkPY43X&asc_refurl=https%3A%2F%2Fwww.wired.com%2Fgallery%2Fbest-apple-watch-accessories%2F&ascsubtag=6220f63a9621fbc9faf148e3&tag=w050b-20 in 3 pages.

"Replacement Bands Compatible with Xiaomi Mi Band 3/Xiaomi Mi band4 Bands, Silicone Wristbands for Women Men", https://www.amazon.com/Replacement-Compatible-Xiaomi-Silicone-Wristbands/dp/B08GLV1B4H?th=1, Aug. 25, 2020, pp. 5.

Ritche Silicone Watch Band 18mm 20mm 22mm Quick Release Rubber Watch Bands for Men Women, first available May 26, 2021, Amazon.com, pp. 10, https://www.amazon.com/Ritche-Silicone-Watch-Release-Rubber/dp/B095KG8PRY/ref=sr%201%208?crid=1%20NZTZ03COTGPC&keywords=rubber%2Bwatch%2Bband&qid=1678448896&sprefix=rubber%2Bwatch%2Bband%2Caps%2C108&sr=8-8&th=1.

SEC Filing for Whoop, Inc. noting incorporation in 2011, CIK #0001582746, https://www.sec.gov/Archives/edgar/data/1582746/000158274614000002/xslFormDX01/primary_doc.xml, dated Jun. 20, 2014, pp. 5.

Stuart, S.C., "24 Hours With the Apollo Mood-Altering Wearable", PC Magazine, Dec. 10, 2019, https://www.pcmag.com/news/24-hours-with-the-apollo-mood-altering-wearable, pp. 10.

Whoop, "The Whoop Strap 3.0", as archived Feb. 3, 2021, https://web.archive.org/web/20210203174156/https://www.whoop.com/membership/strap/, pp. 6.

"Xiaomi Mi Band", Release Date Jul. 22, 2014, Wikipedia, https://en.wikipedia.org/wiki/Xiaomi_Mi_Band, pp. 5.

(56) References Cited

OTHER PUBLICATIONS

"Xiaomi Mi Band 3/4 Silicone Strap", Believed to be available on/before Apr. 15, 2019 based on customer review date, https://judge.me/reviews/www.penguin.com.bd/products/xiaomi-mi-band-3-4-silicone-strap-orange, p. 4.

"Z Create Design strap Strap Smart Sports Bracelet Replacement Strap Wrist Protector Frame ShellReplacement watch strap", https://www.amazon.com/Create-Design-Bracelet-Replacement-Protector/dp/B0B6ZMDJBG?th=1, First available Jul. 19, 2022, pp. 4.

\* cited by examiner

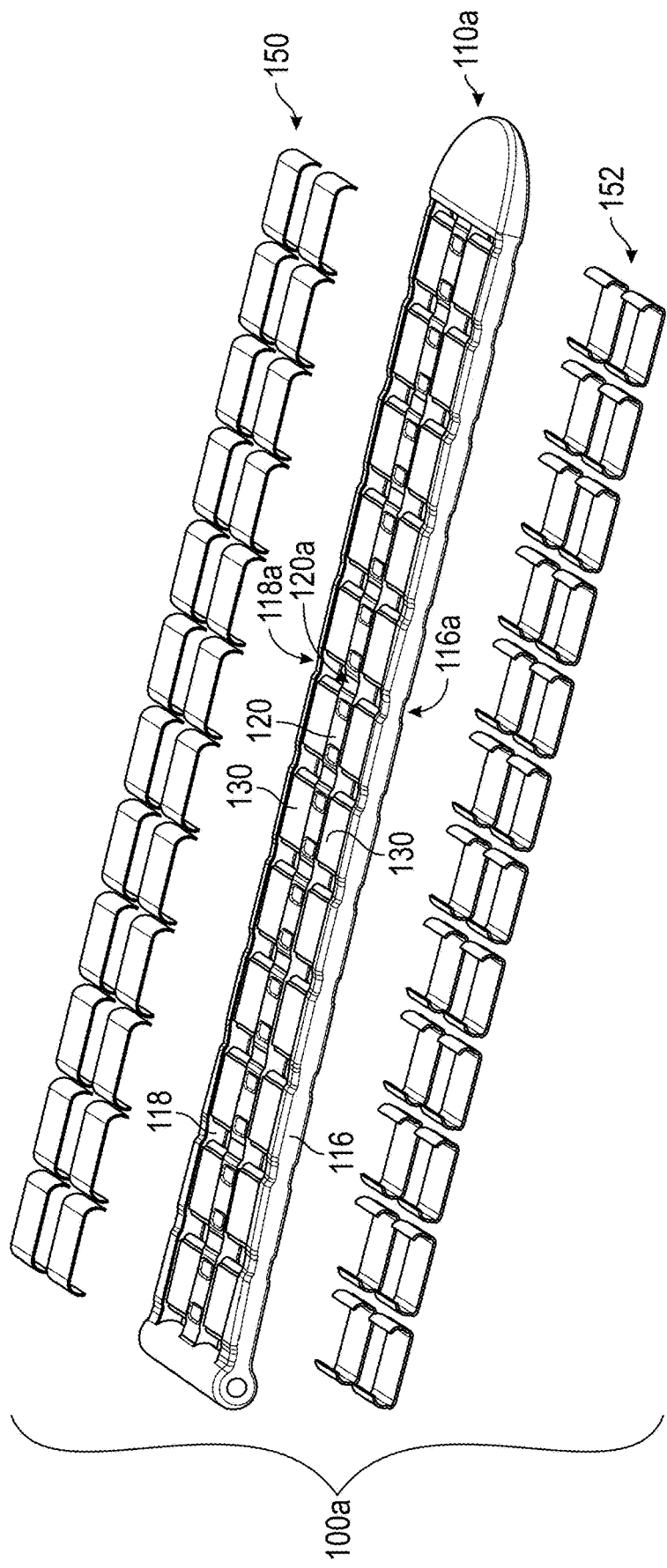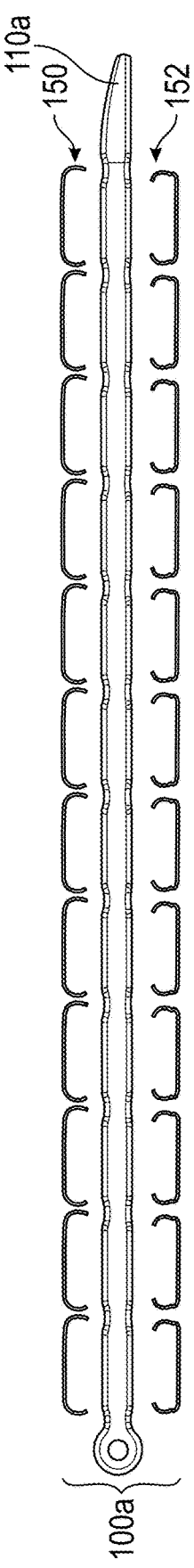
FIG. 3E
FIG. 3F

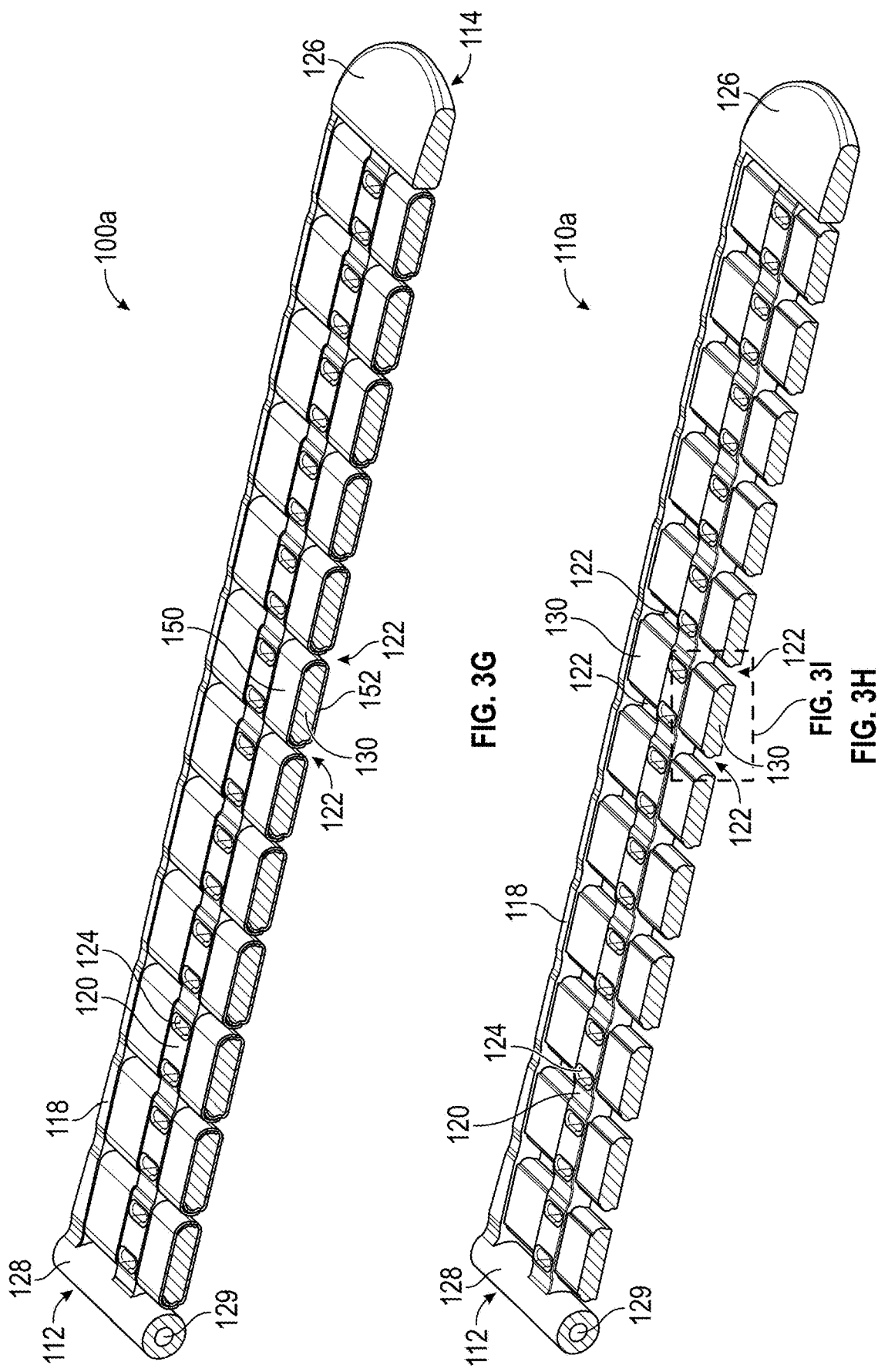

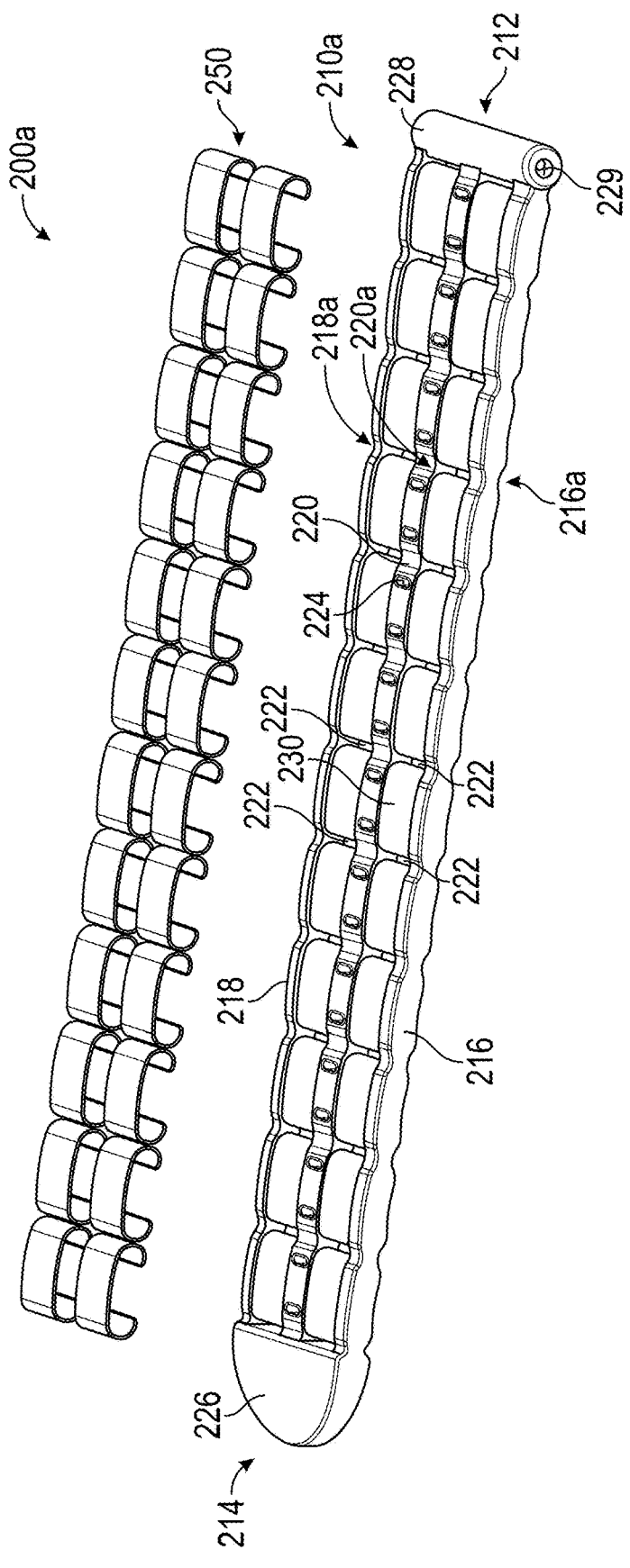
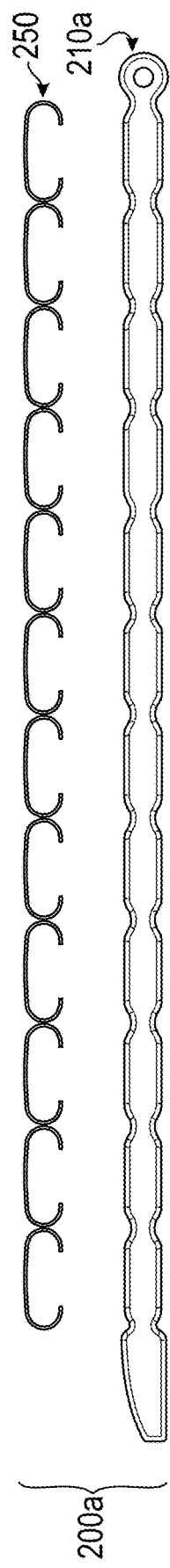
FIG. 4C
FIG. 4D

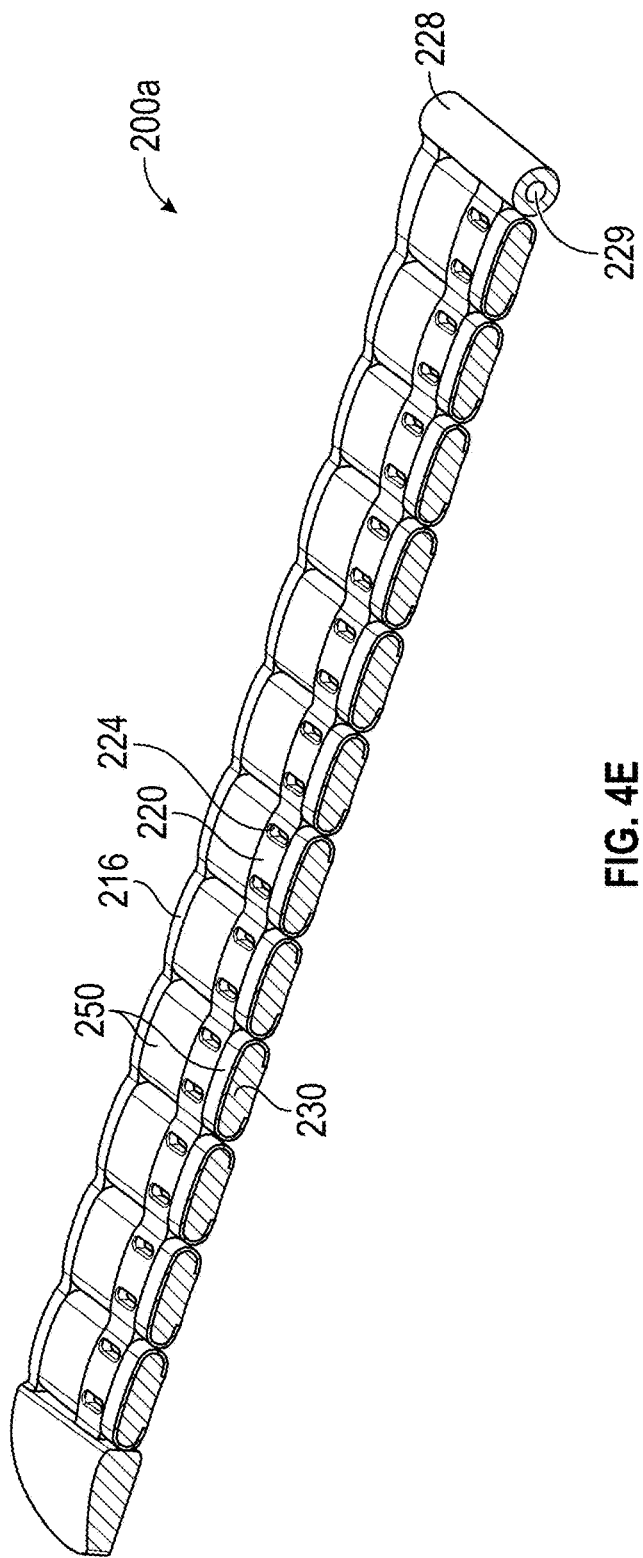
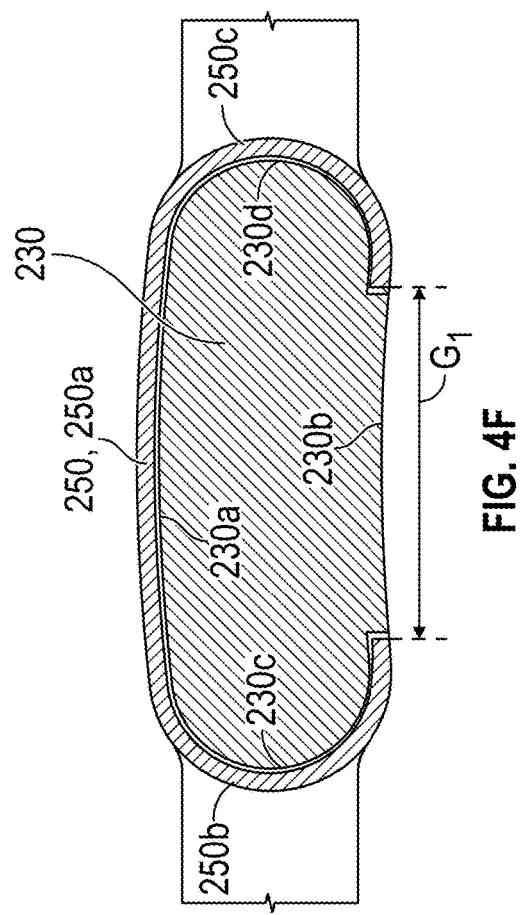
FIG. 4E
FIG. 4F

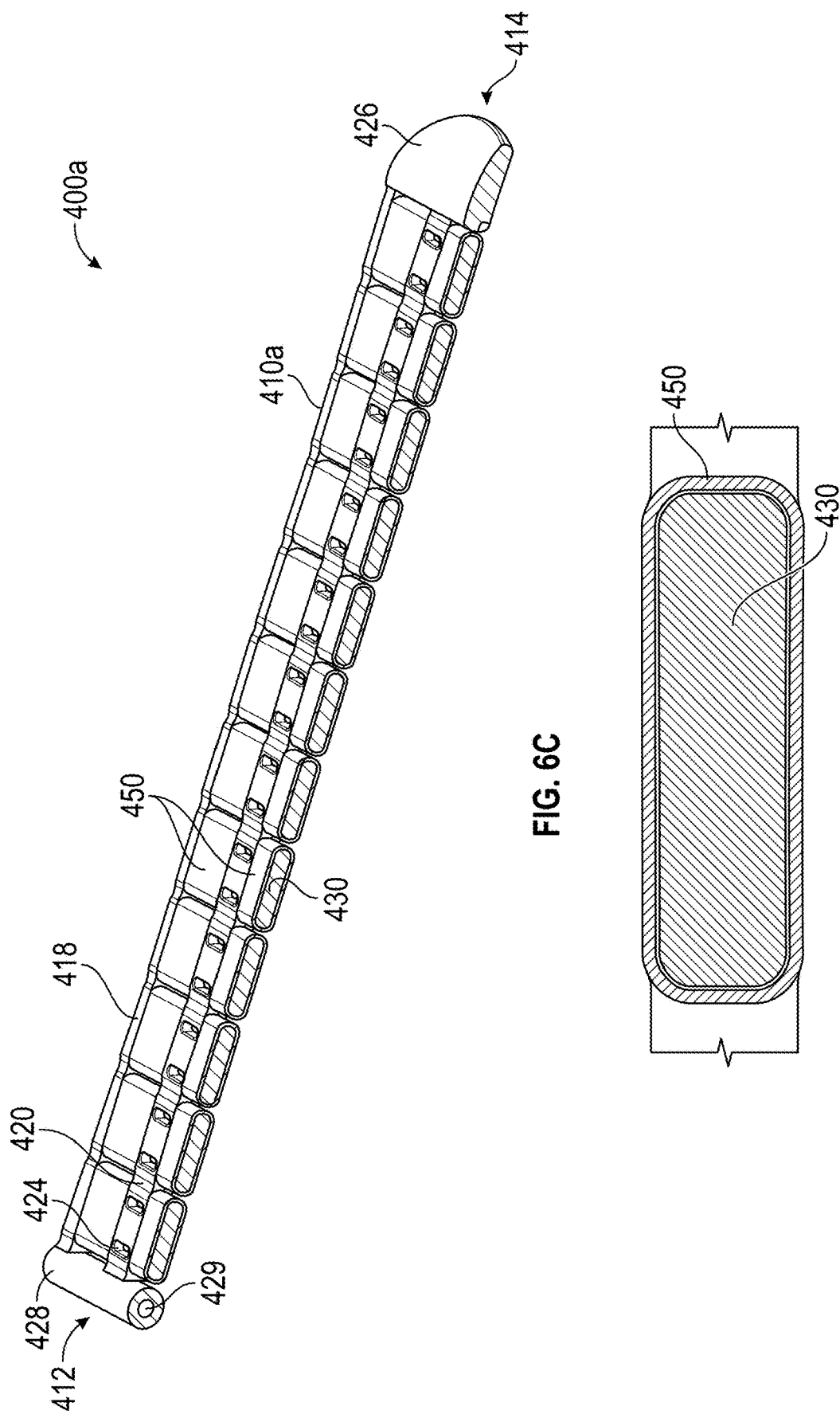

STRAP FOR A WEARABLE DEVICE

INCORPORATION BY REFERENCE TO ANY PRIORITY APPLICATIONS

This application claims the benefit of priority under 35 U.S.C. § 119(e) to U.S. Patent Application No. 63/068,256, entitled "WEARABLE PHYSIOLOGICAL MONITORING DEVICE WITH ADJUSTABLE STRAPS", filed Aug. 20, 2020 and U.S. Patent Application No. 63/067,622, entitled "WEARABLE PHYSIOLOGICAL MONITORING DEVICE WITH ADJUSTABLE STRAPS" filed Aug. 19, 2020, all of which are hereby incorporated by reference herein in their entireties. Any and all applications for which a foreign or domestic priority claim is identified in the Application Data Sheet as filed with the present application are hereby incorporated by reference under 37 CFR 1.57.

FIELD

The present disclosure relates to straps for securing a wearable device, such as a wrist-worn health monitoring device, to a portion of a user's body, such as a wrist.

BACKGROUND

A patient monitoring device can include a pulse oximeter. The oximeter can calculate oxygen saturation ($SpO_2$), pulse rate, a plethysmograph waveform, perfusion index (PI), pleth variability index (PVI), methemoglobin (MetHb), carboxyhemoglobin (CoHb), total hemoglobin (tHb), glucose, and/or otherwise. The oximeter can display on one or more monitors the foregoing parameters individually, in groups, in trends, as combinations, or as an overall wellness or other index.

A pulse oximetry sensor is described in U.S. Pat. No. 6,088,607 entitled Low Noise Optical Probe; pulse oximetry signal processing is described in U.S. Pat. Nos. 6,650,917 and 6,699,194 entitled Signal Processing Apparatus and Signal Processing Apparatus and Method, respectively; a pulse oximeter monitor is described in U.S. Pat. No. 6,584,336 entitled Universal/Upgrading Pulse Oximeter; all of which are assigned to Masimo Corporation, Irvine, CA, and each is incorporated by reference herein in its entirety.

SUMMARY

Monitoring of physiological parameters using pulse oximetry can be useful not only for patients in traditional hospital care settings, but also for individuals in the ordinary course of daily activities. Oximetry utilizes a noninvasive optical sensor to measure physiological parameters of a person. In general, the sensor has light emitting diodes (LEDs) that transmit optical radiation into a tissue site and one or more detectors that detect the optical radiation after absorption (by transmission, reflectance, or transreflectance) by, for example, pulsatile arterial blood flowing within the tissue site. Based on the detected optical radiation, a processor can determine measurements for peripheral oxygen saturation (SpO2), which is an estimate of the percentage of oxygen bound to hemoglobin in the blood, pulse rate, plethysmograph waveforms, which indicate changes in the volume of arterial blood with each pulse beat, and perfusion quality index (for example, an index that quantifies pulse strength at the sensor site), among many others.

A physiological monitoring module, also referred to herein as a plethysmograph module or a module, can be incorporated in a wearable device that is secured to a portion of a person's body, such as a wrist of a person (the "wearer"). Such wearable device can be a watch, for example. The module on the watch can be used to monitor one or more physiological parameters of the wearer. The module can detect pulse rate, oxygen saturation, and/or other physiological parameters, such as any of those disclosed elsewhere herein. The module can include a curvature to improve pressure and contact, and therefore optical coupling, between the wearer's skin and the plethysmograph module. The curvature of the module can be designed to balance pressure of the watch on the wearer's wrist and the wearer's comfort. In some implementations, the module and/or the watch can include a connection port to receive another pulse oximeter sensor configured to be coupled to the wearer at a different measurement site of the wearer's body than the wrist.

Some wearable devices which include components and/or functionality configured to allow measurement of physiological parameters of a user secure to the user via one or more straps. The amount of pressure and/or contact applied by the wearable device when associated straps are secured to the wearer can have a significant affect on the integrity of the physiological parameter measurements obtained by the wearable device. Accordingly, it is desirable to ensure that the straps which secure the wearable device facilitate good pressure and/or contact with the wearer's skin. At the same time, however, wearer comfort is an important consideration. If the straps and/or wearable device are configured such that good pressure and/or contact between the wearable device and the wearer's skin causes discomfort for the wearer, the wearer may only be able to wear the wearable device for short periods of time and/or may loosen the strap(s) in a manner which may impair the integrity of physiological measurements obtained by the wearable device. Some conventional straps for wearable devices are made only of a pliable material which, while providing some comfort to the user, may be allowed to flex and/or stretch too much, thereby impairing the integrity of physiological measurements obtained by the wearable device coupled with the straps. Further, the material of such conventional straps may be rough and/or otherwise uncomfortable to the wearer, especially over long periods of time.

In various implementations, the present disclosure describes straps for securing a wearable device to a user that are made of metal and also with a more pliable material (for example, a more stretchable material) to facilitate both robust physiological parameter measurements and user comfort. For example, various implementations of the straps disclosed herein incorporate metal (for example, a plurality of metal parts and/or sections) and a different material that is more pliable (for example, more stretchable) than metal, such as a material comprising rubber and/or silicone. In some implementations, a majority (for example, greater than 50%, 55%, 60%) of the strap comprises a non-metallic material, such as rubber and/or silicone. In some implementations, less than half of the strap comprises a metallic material (such as stainless steel). In some implementations, at least half of the strap comprises a non-metallic material, such as rubber and/or silicone. In some implementations, a majority (for example, greater than 50%) of a portion of the strap that contacts the user's skin when the wearable device and/or strap is in use comprises a metallic material, for example, a smooth metallic material. Such configurations can increase user comfort since the metallic material can facilitate a smooth contact surface with the wearer's skin. Such configurations can also facilitate greater user comfort at the skin-contact interface in comparison to straps made entirely of a non-metallic material such as rubber or leather, especially when the straps are in use for long periods of time. Various implementations of the straps disclosed herein incorporate openings along a length and/or width of the strap which can, among other things, allow air to reach skin proximate the straps and facilitate breathability. Such openings can be separate from holes along portions of the strap which are configured to receive a buckle tongue of a corresponding strap to form a closed loop around a portion of the wearer's body (for example, wrist). Advantageously, various implementations of the straps disclosed herein incorporate metal and a non-metallic material (for example, silicone and/or rubber) to facilitate optimal pressure and/or contact with the wearer's skin and thus increased accuracy in physiological parameter measurements and increased comfort.

In various implementations, the present disclosure describes straps that do not comprise metal links that join portions of the strap together. In some implementations, the disclosed straps include one or more or a plurality of living hinges in non-metallic portions of the straps, such as in and/or along edge members of the straps which can define sides of the straps. Such living hinges can be spaced apart from one another. In some implementations, such living hinges are formed by narrowing portions of such edge members.

Disclosed herein is a strap for a wearable device configured to secure to a portion of a body of a user. In some implementations, the strap comprises: a base comprising a first material; and a plurality of strap members positioned around portions of the base along a length of the base, each of the plurality of strap members comprising a second material, wherein the first material of the base is more pliable than the second material of each of the plurality of strap members.

In some implementations, the base comprises an integrally molded structure. In some implementations, the first material comprises at least one of rubber and silicone. In some implementations, the second material comprises metal. In some implementations, the second material comprises stainless steel. In some implementations, the plurality of strap members limit an ability of the base to stretch along an axis generally parallel to the length of the base. In some implementations, portions of the plurality of strap members are configured to contact skin of the user when the strap is secured to the user's wrist in use. In some implementations, said portions of the plurality of strap members are smooth.

In some implementations, an amount of the strap that is comprised by the base is greater than an amount of the strap that is comprised by the plurality of strap members. In some implementations, the plurality of strap members are configured to surround said portions of the base. In some implementations, the plurality of strap members do not comprise an integrally formed structure.

In some implementations, the base further comprises a first end configured to connect to a first portion of the wearable device and a second end opposite the first end, and wherein the length of the base extends between the first and second ends. In some implementations, the plurality of strap members are spaced from the first end and the second end of the base. In some implementations, the base further comprises a width extending between opposite sides of the base, and wherein the plurality of strap members are inset from the sides of the base between said width.

In some implementations: the base further comprises: a first end configured to connect to a portion of the wearable device; a second end opposite the first end, wherein said length extends between the first and second ends; a width extending between opposite sides of the base; a plurality of openings spaced from one another along the length; and a plurality of stems, each of the plurality of stems positioned between two of said plurality of openings and extending generally in a direction of the width; and the plurality of strap members comprises a plurality of channels positioned at least partially around the plurality of stems of the base. In some implementations, each of said plurality of channels comprises a web and at least one leg extending from the web, and wherein the web and the at least one leg are configured to surround a portion of one of the plurality of stems.

In some implementations, each of said plurality of channels comprises said web and two legs extending from the web. In some implementations, said legs are curved. In some implementations, said web is substantially planar. In some implementations, said web is curved. In some implementations, said two legs extend from opposite ends of the web. In some implementations, said web and said two legs are configured to surround less than an entirety of a cross-section of the one of the plurality of stems. In some implementations, said web and said two legs are configured to surround an entirety of a cross-section of the one of the plurality of stems.

In some implementations, said plurality of channels comprises a plurality of pairs of channels secured at least partially around the plurality of stems of the base. In some implementations, each of the plurality of pairs of channels comprises: a first channel configured to surround a first portion of one of the plurality of stems; and a second channel configured to surround a second portion of the one of the plurality of stems. In some implementations, the first channel member is configured to surround less than an entirety of a cross-section of the one of the plurality of stems. In some implementations, the second channel member is configured to surround less than said entirety of said cross-section of the one of the plurality of stems.

In some implementations, the first and second channels cooperate to surround an entirety of a cross-section of the one of the one of the plurality of stems. In some implementations, the first channel is configured to surround at least half of a cross-section of the one of the plurality of stems. In some implementations, the second channel is configured to surround at least half of said cross-section of the one of the plurality of stems. In some implementations, at least a portion of the first channel overlaps at least a portion of the second channel. In some implementations, the first channel overlaps less than an entirety of a cross-section of the second channel. In some implementations, overlapping portions of the first and second channels and non-overlapping portions of the first and second channels cooperate to define a generally rounded shape around the one of the plurality of stems. In some implementations, said generally rounded shape comprises an oblong shape.

In some implementations: the first channel comprises a web and legs extending from opposite ends of the web of the first channel; the second channel comprises a web and legs extending from opposite ends of the web of the second channel; and the legs of the first channel overlap the legs of the second channel when the first and second channels are positioned around the one of the plurality of stems. In some implementations, each of the webs of the first and second channels are generally planar. In some implementations, the legs of the first channel overlap only the legs of the second channel. In some implementations, said overlapping legs of the first and second channels and non-overlapping portions of the first and second channels cooperate to define a generally rounded shape around the one of the plurality of stems.

In some implementations: the one of the plurality of stems comprises a top portion, a bottom portion opposite the top portion, and opposing sides connecting the top and bottom portions; the sides of the one of the plurality of stems are positioned adjacent the legs of the second channel; and the overlapping legs of the first and second channels, the non-overlapping portions of the first and second channels, and the sides of the one of the plurality of stems cooperate to define said generally rounded shape around the one of the plurality of stems.

In some implementations, said generally rounded shape comprises an oblong shape. In some implementations: the legs of the second channel contact the sides of the one of the plurality of stems; and the sides of the one of the plurality of stems are configured such that outer surfaces of ends of the legs of the second channel are substantially flush with a plane of the top portion of the one of the plurality of stems. In some implementations: the legs of the second channel contact the sides of the one of the plurality of stems; and the sides of the one of the plurality of stems are configured such that there is a generally smooth transition between ends of the legs of the second channel and the top portion of the one of the plurality of stems. In some implementations, a gap between an outer surface of each of the legs of the second channel and a surface of the top portion of the one of the plurality of stems is less than 0.1 inch.

In some implementations: the first channel comprises a web and legs extending from opposite ends of the web of the first channel; the second channel comprises a web and legs extending from opposite ends of the web of the second channel; each of the legs of the first channel comprise a first end connected to the web of the first channel and a second end opposite the first end; and each of the legs of the first channel comprise a continuous curve between the first and second ends of each of the legs of the first channel. In some implementations: each of the legs of the second channel comprise a first end connected to the web of the second channel and a second end opposite the first end; and only a portion of each of the legs of the second channel comprises a continuous curve. In some implementations, the first channel comprises a generally C-shaped cross-section. In some implementations, the second channel member comprises a generally C-shaped cross-section.

In some implementations, the base further comprises: a first edge member extending along a first side of the base between the first and second ends; a second edge member extending along a second side of the base between the first and second ends; and a spine member extending along at least a portion of the length and positioned between the first and second edge members. In some implementations, the plurality of openings comprises: a first plurality of openings spaced from one another along at least a portion of the length and extending between the first edge member and the spine member; and a second plurality of openings spaced from one another along at least a portion of the length and extending between the second edge member and the spine member. In some implementations, the plurality of stems comprises: a first plurality of stems, each of the first plurality of stems positioned between two of said first plurality of openings and extending between the first edge member and the spine member; and a second plurality of stems, each of the second plurality of stems positioned between two of said second plurality of openings and extending between the second edge member and the spine member. In some implementations, the first edge member, the second edge member, and the spine member are generally parallel to one another. In some implementations, the first edge member, the second edge member, and the spine member comprise an integrally molded structure.

In some implementations, a wearable device comprising a first strap and a second strap, each of the first and second straps comprising any of the straps described above, wherein: the spine member of the first strap comprises a plurality of spine member openings spaced apart from one another along a length of the spine member of the first strap, and wherein the plurality of spine member openings are configured to receive a tongue of a buckle coupled to the second strap thereby allowing a size of a closed loop formed by the first and second straps to be adjusted. In some implementations, a wearable device comprises any of the straps described above, wherein the wearable device is configured to secure to a wrist of the user and wherein the length of the base is configured to wrap around at least a portion of the user's wrist when in use. In some implementations, a wearable device comprises any of the straps described above, wherein the wearable device is configured to measure one or more physiological parameters of the user. In some implementations, the wearable device is configured to measure at least one of oxygen saturation and pulse rate of the user.

In some implementations, the plurality of strap members are configured to be removably secured to the portions of the base. In some implementations, the plurality of strap members are configured to be non-removably secured to the portions of the base. In some implementations, a wearable device comprises any of the straps described above, wherein the wearable device is a watch.

Disclosed herein is a method of manufacturing a strap for a wearable device, the method comprising: forming a base with a first material; and positioning a plurality of strap members around portions of the base along a length of the base, each of the plurality of strap members comprising a second material, wherein the first material of the base is more pliable than the second material of each of the plurality of strap members.

In some implementations, said forming said base with the first material comprises injection molding said base using a mold assembly. In some implementations, said mold assembly comprises a first mold portion and a second mold portion that are separable from one another. In some implementations, the first material comprises at least one of rubber and silicone. In some implementations, the second material comprises metal. In some implementations, the second material comprises stainless steel. In some implementations, an amount of the strap that is comprised by the base is greater than an amount of the strap that is comprised by the plurality of strap members. In some implementations, the plurality of strap members do not comprise an integrally formed structure.

In some implementations, said forming said base with said first material comprises: forming the base with a first end, a second end, and sides separated by a width, wherein said length extends between said first and second ends; forming a plurality of openings in the base, said plurality of openings spaced from one another along the length of the base; and forming a plurality of stems in the base, each of the plurality of stems positioned between two of said plurality of openings and extending generally in a direction of the width. In some implementations, said positioning said plurality of strap members around said portions of the base along the length of the base comprises: positioning said plurality of strap members around the plurality of stems in the base. In some implementations, said plurality of strap members comprises a plurality of channels and wherein the method comprises securing said plurality of channels to the plurality of stems in the base. In some implementations, each of said plurality of channels comprises a web and at least one leg extending from the web, and wherein said securing said plurality of channels to the plurality of stems in the base comprises securing the web and at least one leg of each of the plurality of channels around a portion of one of the plurality of stems.

In some implementations, each of said plurality of channels comprises a web and two legs extending from the web, and wherein said securing the web and said at least one leg of each of the plurality of channels around the portion of the one of the plurality of stems comprises securing the web and the two legs around the portion of the one of the plurality of stems. In some implementations, said securing the web and the two legs around the portion of the one of the plurality of stems comprises securing the web and the two legs around less than an entirety of a cross-section of the one of the plurality of stems. In some implementations, said securing the web and the two legs around the portion of the one of the plurality of stems comprises securing the web and the two legs around an entirety of a cross-section of the one of the plurality of stems.

In some implementations, said plurality of channels comprises a plurality of pairs of channels, each of the plurality of pairs of channels comprising a first channel and a second channel, and wherein said securing said plurality of channels to the plurality of stems in the base comprises: securing the first channel around a first portion of one of the plurality of stems; and securing the second channel around a second portion of the one of the plurality of stems. In some implementations: said securing the first channel around said first portion of one of the plurality of stems comprises securing the first channel around less than an entirety of a cross-section of the one of the plurality of stems; and said securing the second channel around said second portion of the one of the plurality of stems comprises securing the second channel around less than the entirety of the cross-section of the one of the plurality of stems. In some implementations, said securing said first and second channels around said first and second portions of the one of the plurality of stems comprises securing the first and second channels to the one of the plurality of stems such that the first and second channels cooperate to surround an entirety of a cross-section of the one of the one of the plurality of stems. In some implementations, said securing said first and second channels around said first and second portions of the one of the plurality of stems comprises overlapping portions of the first and second channels with each other.

In some implementations, each of the first and second channels comprises a web and opposing legs extending from the web, and wherein said overlapping portions of the first and second channels comprise said opposing legs of the first and second channels. In some implementations, said securing said first and second channels to said first and second portions of the one of the plurality of stems comprises securing said first and second channels such that overlapping portions of the first and second channels and non-overlapping portions of the first and second channels cooperate to define a generally rounded shape around the one of the plurality of stems. In some implementations, said generally rounded shape comprises an oblong shape.

In some implementations, said forming the said base further comprises: forming the base with a first edge member extending along a first side of the base between the first and second ends; forming the base with a second edge member extending along a second side of the base between the first and second ends; and forming the base with a spine member extending along at least a portion of the length and positioned between the first and second edge members. In some implementations, said forming said plurality of openings in the base comprises: forming a first plurality of openings spaced from one another along at least a portion of the length and between the first edge member and the spine member; and forming a second plurality of openings spaced from one another along at least a portion of the length and between the second edge member and the spine member.

In some implementations, said forming said plurality of stems in the base comprises: forming a first plurality of stems, each of the first plurality of stems positioned between two of said first plurality of openings and extending between the first edge member and the spine member; and forming a second plurality of stems, each of the second plurality of stems positioned between two of said second plurality of openings and extending between the second edge member and the spine member. In some implementations, the first edge member, the second edge member, and the spine member are formed generally parallel to one another. In some implementations, the first edge member, the second edge member, and the spine member are integrally molded. In some implementations, the method further comprises forming a plurality of spine member openings spaced apart from one another along a length of the spine member, wherein each of the plurality of spine member openings are configured to receive a tongue of a buckle coupled to a separate strap of the wearable device thereby allowing a size of a closed loop formed by the strap and the separate strap to be adjusted.

Disclosed herein is a strap for a wearable device configured to secure to a wrist of a user, the wearable device configured to measure one or more physiological parameters of the user. In some implementations, the strap comprises a base comprising an integral structure made of a first material, the base further comprising: a first end configured to connect to a portion of the wearable device; a second end opposite the first end; a length extending between the first and second ends, wherein the base is configured to bend along the length to allow the strap to wrap around at least a portion of the user's wrist when in use; a width extending between opposite sides of the base; a plurality of openings spaced from one another along the length; and a plurality of stems, each of the plurality of stems positioned between two of said plurality of openings and extending generally in a direction of the width. The strap can further comprise a plurality of pairs of channels positioned around the plurality of stems, each of the plurality of pairs of channels comprising: a first channel positioned partially around one of the plurality of stems such that the first channel surrounds less than an entirety of the one of the plurality of stems, wherein the first channel comprises a second material; and a second channel positioned partially around the one of the plurality of stems such that the second channel surrounds less than said entirety of the one of the plurality of stems, wherein the second channel comprises the second material. In some implementations, the first and second channels are secured to one another around the one of the plurality of stems such that portions of the first and second channels overlap one another. In some implementations, the second material of the first and second channels is less pliable than the first material of the base.

In some implementations, the first material comprises stainless steel. In some implementations, the second material comprises at least one of silicone and rubber. In some implementations: the first channel comprises a web and legs extending from opposite ends of the web of the first channel; the second channel comprises a web and legs extending from opposite ends of the web of the second channel; and the legs of the first channel overlap the legs of the second channel. In some implementations, the webs of the first and second channels do not overlap one another. In some implementations, the webs of the first and second channels are generally planar and wherein the legs of the first and second channels are curved. In some implementations, the legs of the first channel overlap only the legs of the second channel.

In some implementations: the one of the plurality of stems comprises a top portion, a bottom portion opposite the top portion, and opposing sides connecting the top and bottom portions; the sides of the one of the plurality of stems are positioned adjacent the legs of the second channel; and the overlapping legs of the first and second channels, non-overlapping portions of the first and second channels, and the sides of the one of the plurality of stems cooperate to define a generally rounded shape around the one of the plurality of stems. In some implementations: the legs of the second channel contact the sides of the one of the plurality of stems; and the sides of the one of the plurality of stems are configured such that at least a portion of an outer surface of each of the legs of the second channel is substantially flush with a plane of the top portion of the one of the plurality of stems.

In some implementations, the base further comprises: a first edge member at least partially defining a first side of the base between the first and second ends; a second edge member at least partially defining a second side of the base between the first and second ends, said second side being opposite said first side; and a spine member extending along at least a portion of the length and positioned between the first and second edge members, wherein the spine member is generally parallel to the first and second edge members. In some implementations, the plurality of openings comprises: a first plurality of openings spaced from one another along at least a portion of the length and extending between the first edge member and the spine member; and a second plurality of openings spaced from one another along at least a portion of the length and extending between the second edge member and the spine member. In some implementations, the plurality of stems comprises: a first plurality of stems, each of the first plurality of stems positioned between two of said first plurality of openings and extending between the first edge member and the spine member; and a second plurality of stems, each of the second plurality of stems positioned between two of said second plurality of openings and extending between the second edge member and the spine member. In some implementations, a wearable device comprises any of the straps described above, wherein the wearable device is configured to measure at least one of oxygen saturation and pulse rate of the user.

Disclosed herein is a strap for a wearable device configured to secure to a wrist of a user. In some implementations, the strap comprises a base comprising an integral structure made of a first material, the base further comprising: a first end configured to connect to a portion of the wearable device; a second end opposite the first end; a length extending between the first and second ends; a width extending between opposite sides of the base; a plurality of openings spaced from one another along the length; and a plurality of stems, each of the plurality of stems positioned between two of said plurality of openings and extending generally in a direction of the width. In some implementations, the strap further comprises a plurality of pairs of channels positioned around the plurality of stems, each of the plurality of pairs of channels comprising: a first channel positioned at least partially around one of the plurality of stems; and a second channel positioned at least partially around the one of the plurality of stems and secured to the first channel; wherein the first and second channels comprise a second material that is less pliable than the first material of the base.

In some implementations, the first material comprises a metallic material and wherein the second material comprises at least one of silicone and rubber. In some implementations, the first and second channels are not integral with one another. In some implementations: the first channel comprises a web and legs extending from opposite ends of the web of the first channel; the second channel comprises a web and legs extending from opposite ends of the web of the second channel; and the legs of the first channel overlap the legs of the second channel. In some implementations, the webs of the first and second channels do not overlap one another. In some implementations: the one of the plurality of stems comprises a top portion, a bottom portion opposite the top portion, and opposing sides connecting the top and bottom portions; the sides of the one of the plurality of stems contact the legs of the second channel; the legs of the second channel are sandwiched between the sides of the one of the plurality of stems and the legs of the first channel; and the overlapping legs of the first and second channels, non-overlapping portions of the first and second channels, and the sides of the one of the plurality of stems cooperate to define a generally rounded shape around the one of the plurality of stems.

Disclosed herein is a strap for a wearable device configured to secure to a portion of a user's body, the strap comprising: a base and a plurality of strap members secured to and/or positioned around portions of the base. In some implementations, the base comprises a first material and further comprises: a first end, a second end opposite the first end, and a length extending between the first and second ends; a plurality of openings spaced from one another along the length; and a plurality of stems, each of the plurality of stems positioned between two of said plurality of openings. In some implementations, the plurality of strap members are positioned around the plurality of stems and comprise a second material that is less pliable than the first material.

In some implementations, the first material comprises a metallic material and the second material comprises at least one of silicone and rubber. In some implementations, the plurality of strap members comprises a plurality of pairs of channels positioned around the plurality of stems, each of the plurality of pairs of channels comprising: a first channel positioned partially around one of the plurality of stems such that the first channel surrounds less than an entirety of the one of the plurality of stems; and a second channel positioned partially around the one of the plurality of stems such that the second channel surrounds less than said entirety of the one of the plurality of stems. In some implementations, the first and second channels are secured to one another around the one of the plurality of stems such that portions of the first and second channels overlap one another.

Although various implementations of the straps disclosed herein may be described with reference to a wearable device that measures and/or monitors physiological parameters and/or characteristics of a wearer, any of the disclosed straps can be utilized with a wearable device that does not measure and/or monitor physiological parameters and/or characteristics of a wearer. For example, any of the straps disclosed herein may be utilized with a watch that does not does not measure and/or monitor physiological parameters and/or characteristics of a wearer. In such configurations, various implementations of the disclosed straps can advantageously provide increased comfort to the wearer, for example, via the incorporation of metal and pliable materials, such as metal channel members secured to a non-metallic (for example, silicone and/or rubber) body of the straps.

For purposes of summarizing the disclosure, certain aspects, advantages, and novel features are discussed herein. It is to be understood that not necessarily all such aspects, advantages, or features will be embodied in any particular embodiment of the disclosure, and an artisan would recognize from the disclosure herein a myriad of combinations of such aspects, advantages, or features.

BRIEF DESCRIPTION OF THE DRAWINGS

Certain features of this disclosure are described below with reference to the drawings. The illustrated embodiments are intended to illustrate, but not to limit, the embodiments. Various features of the different disclosed embodiments can be combined to form further embodiments, which are part of this disclosure.

FIG. 3E illustrates an exploded perspective view of the strap of FIG. 3C in accordance with aspects of this disclosure.

FIG. 3F illustrates an exploded side view of the strap of FIG. 3C in accordance with aspects of this disclosure.

FIG. 3G illustrates a perspective view of a cross-section taken through the strap of FIG. 3C in accordance with aspects of this disclosure.

FIG. 3H illustrates the perspective view of FIG. 3G with a portion of the strap of FIG. 3C removed in accordance with aspects of this disclosure.

FIG. 4C illustrates an exploded perspective view of the strap of FIG. 4A in accordance with aspects of this disclosure.

FIG. 4D illustrates an exploded side view of the strap of FIG. 4A in accordance with aspects of this disclosure.

FIG. 4E a perspective view of a cross-section taken through the strap of FIG. 4A in accordance with aspects of this disclosure.

FIG. 4F illustrates an enlarged cross-sectional view of a portion of the strap of FIG. 4A in accordance with aspects of this disclosure.

FIG. 6C a perspective view of a cross-section taken through the strap of FIG. 5A in accordance with aspects of this disclosure.

FIG. 6D illustrates an enlarged cross-sectional view of a portion of the strap of FIG. 6A in accordance with aspects of this disclosure.

DETAILED DESCRIPTION

Although certain embodiments and examples are described below, those of skill in the art will appreciate that the disclosure extends beyond the specifically disclosed embodiments and/or uses and obvious modifications and equivalents thereof based on the disclosure herein. Thus, it is intended that the scope of the disclosure herein disclosed should not be limited by any particular embodiments described below.

Daily use of a wearable health monitoring device can be beneficial to a wearer. Wearable devices which incorporate pulse oximetry components can be utilized to measure and/or monitor various physiological parameters and/or characteristics such as oxygen saturation ($SpO_2$), pulse rate, a plethysmograph waveform, perfusion index (PI), pleth variability index (PVI), methemoglobin (MetHb), carboxyhemoglobin (CoHb), total hemoglobin (tHb), glucose, electrocardiogram (ECG) parameters, among others.

Figure 1A:
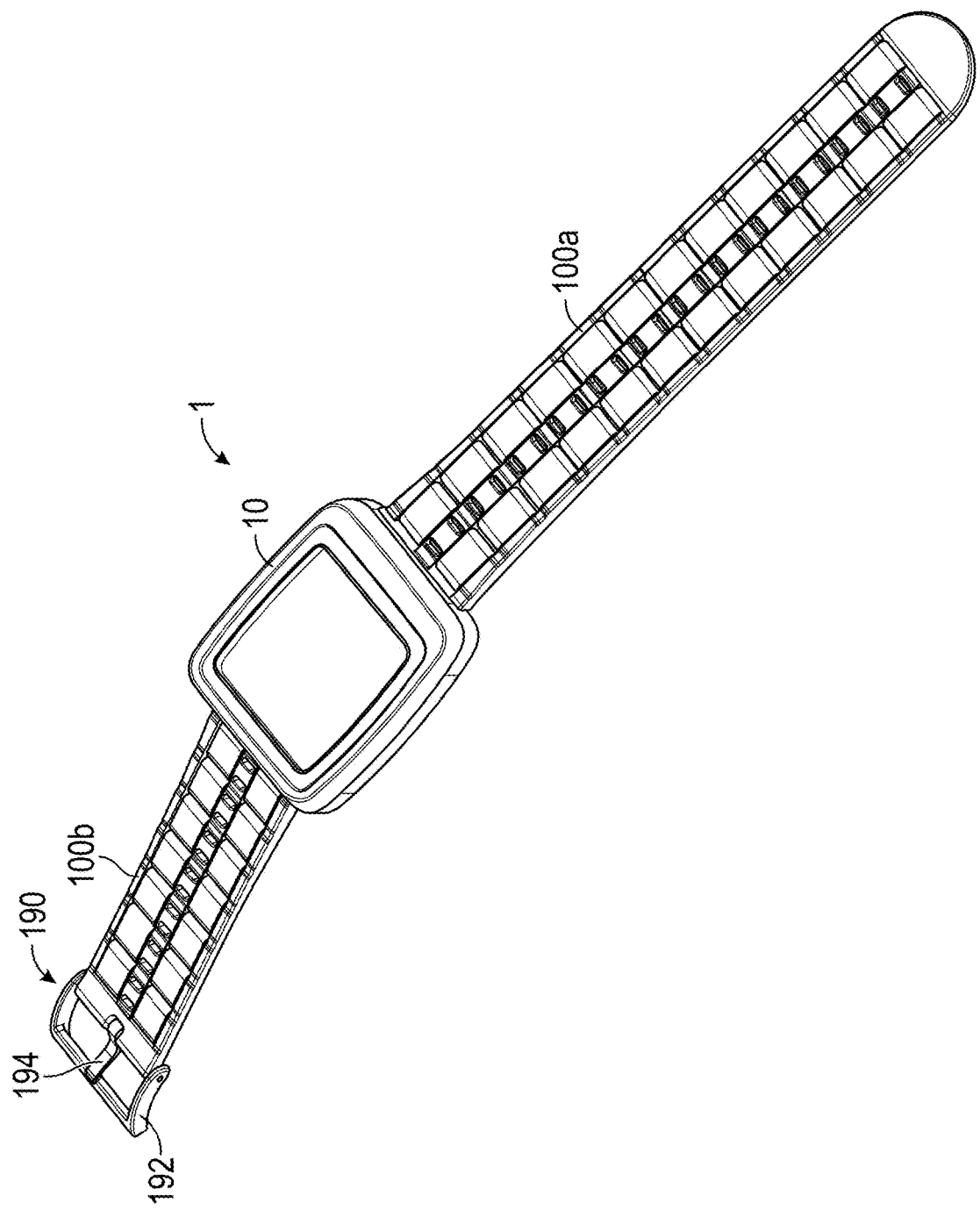
FIGS. 1A-1B illustrate perspective views of a wearable device including straps in accordance with aspects of this disclosure.
Figure 1B:
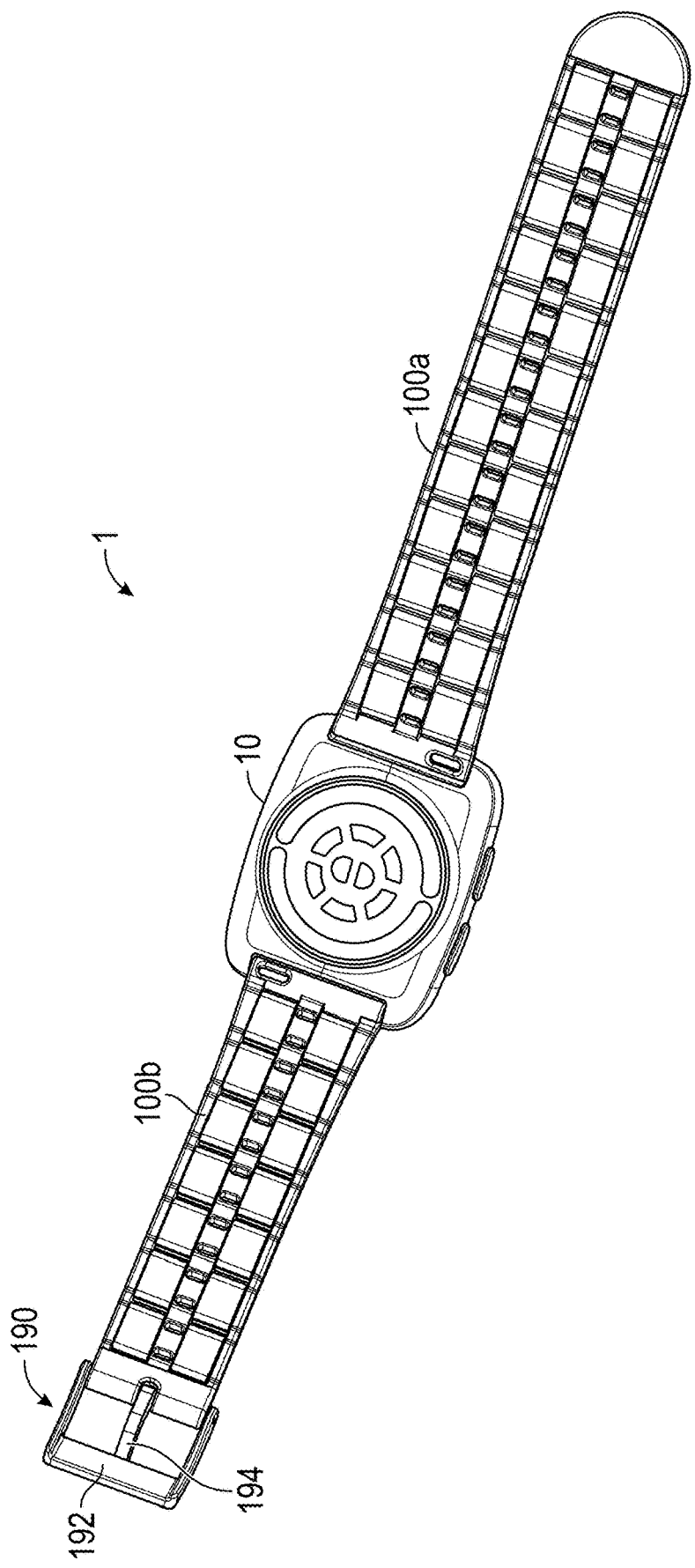

FIGS. 1A-1B illustrate perspective views of a wearable device 1. The wearable device 1 can include one or more straps. For example, the wearable device 1 can include strap 100a and strap 100b. Straps 100a, 100b can be configured to secure to a portion of a user's body. For example, straps 100*a*, 100*b* can secure around a wrist of the user and/or can secured to one another. While straps disclosed herein may be described and/or shown with reference to a wearer's wrist, any of the straps disclosed herein can be configured to secure to other portions of a wearer's body, such as an ankle, leg, arm, chest, among other locations.

Figure 1C:
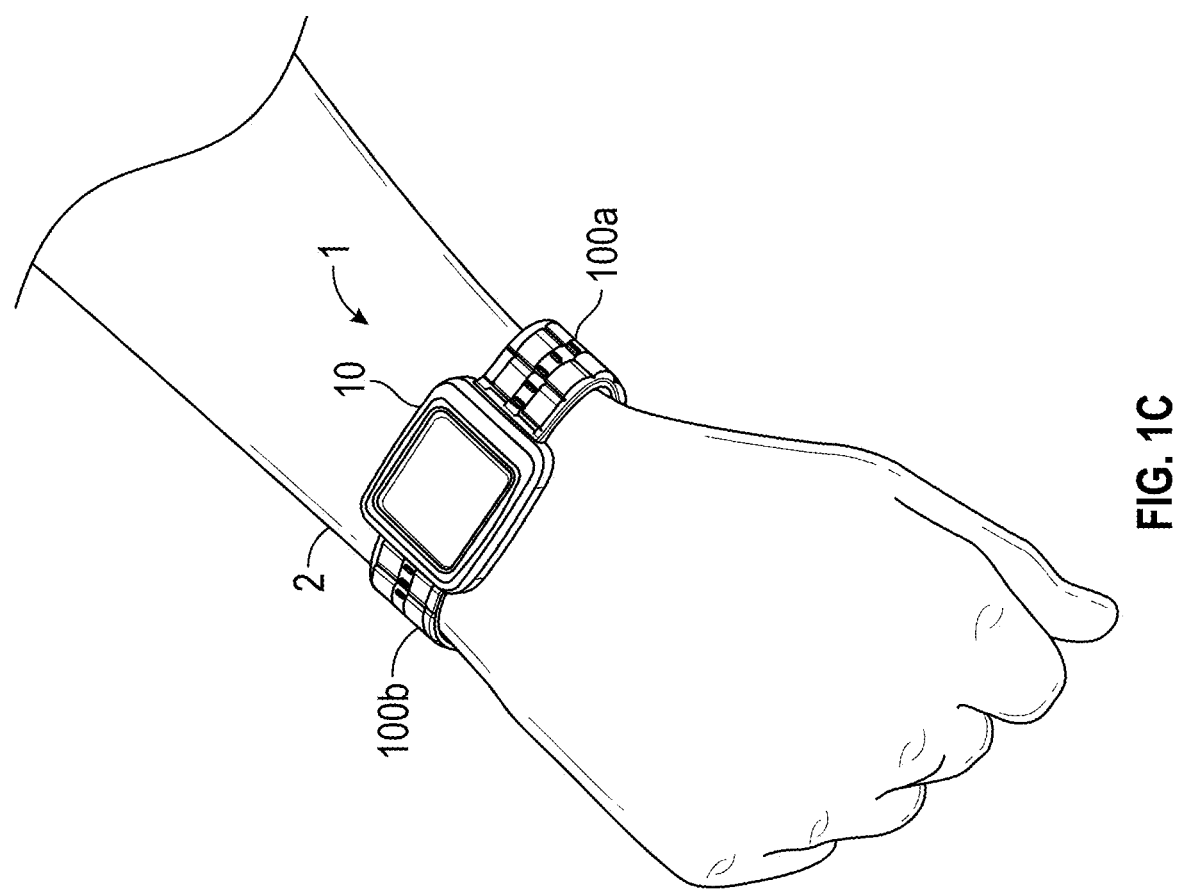
FIG. 1C illustrates a perspective view of the wearable device and straps of FIGS. 1A-1B secured to a user's wrist in accordance with aspects of this disclosure.

FIG. 1C illustrates the wearable device 1 secured around a wrist 2 of a user. Wearable device 1 (for example, strap 100*a* and/or strap 100*b*) can include a mechanism configured to allow the straps 100*a*, 100*b* to secure around a portion of the user's body (for example, wrist 2). For example, with reference to FIGS. 1A-1B and 3A-3B, the wearable device 1 can include a buckle 190 that can facilitate securement of the straps 100*a*, 100*b* to one another. Buckle 190 can include a buckle body 192 and a tongue 194 (which can also be referred to as a "buckle tongue"). Straps 100*a*, 100*b* can be secured to one another via insertion of at least a portion of strap 100*a* through an opening defined by buckle body 192 and insertion of tongue 194 through one of a plurality of openings in strap 100*a* (such as one of a plurality of openings 124 of strap 100*b* as shown in FIGS. 3C-3D and discussed further below). Buckle 190 can be coupled with an end of strap 100*b*. For example, buckle 190 can be coupled to an end of strap 100*b* via a pin that extends through a through-hole in an end of strap 100*b* and opposing holes in the buckle body 192. Such securement can rotatably couple the buckle body 192 to the end of the strap 100*b*. In some implementations, as shown in at least FIG. 1A, tongue 194 can be coupled (for example, rotatably coupled) to an end of strap 100*b*, for example, via the above-described pin that can extend through a through-hole in the end of strap 100*b* and at least partially through such opposing holes in buckle body 192. As shown, buckle body 192 can define an opening (for example, when coupled to an end of strap 100*b*) that can be configured to receive an end of strap 100*a* to facilitate securement of straps 100*a*, 100*b* and/or formation of a closed loop around a portion of the wearer's body.

Wearable device 1 can be a wristwatch incorporating a plethysmograph sensor (which may also be referred to as a "pulse oximeter" or "oximetry sensor" or "optical sensor") with built-in watch and/or time-indicating functions. Straps 100*a*, 100*b* can be pliable as described in more detail below which can allow tightness of the device 1 around the wrist 2 of the wearer be adjusted so as to provide better contact between the plethysmograph sensor and the wrist 2 while not compromising the comfort of the wearer and/or reducing the blood flow across the wrist 2 in a way that reduces the accuracy of physiological parameter measurement by the plethysmograph sensor. Accordingly, in some implementations, the wearable device 1 can eliminate the need to wear an additional sensor (for example, a pulse oximetry sensor) when going about daily activities. Incorporation of an oximetry sensor in wearable device 1 can provide the benefits of physiological information monitoring in a discrete (for example, hidden) form. A wearer of the wearable device 1 can be informed of physiological parameters, such as vital signs including but not limited to heart rate and oxygen saturation. This information can be helpful in providing feedback to the wearer and/or a third party user, for example, a healthcare professional or the wearer's family member, when the wearer is exercising, or otherwise for warning the wearer of possible health-related conditions, including but not limited to changes in the wearer's physiological parameters in response to medication that is being administered to the wearer.

Figure 2:
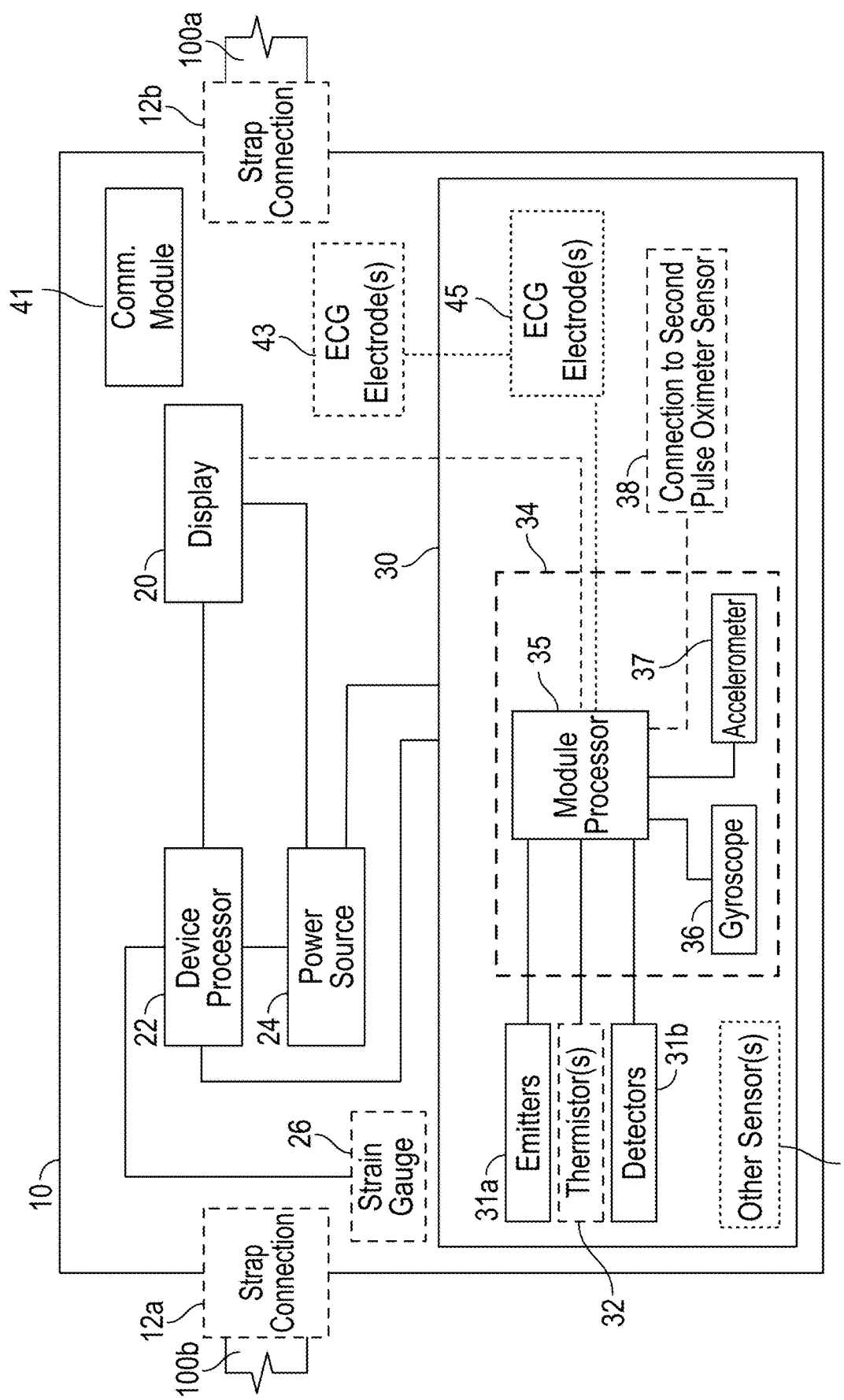
FIG. 2 illustrates a schematic diagram illustrating certain features that can be incorporated into the wearable device of FIGS. 1A-1C in accordance with aspects of this disclosure.

FIG. 2 shows an illustrative schematic diagram of certain features that can be incorporated into wearable device 1.

Wearable device 1 can include straps 100*a*, 100*b* and a module 10, which can be referred to as an electronic module or a watch module (for example, when the wearable device 1 is worn on a wrist like a wrist-watch). Watch module 10 can include strap connections 12*a*, 12*b* that can allow the straps 100*a*, 100*b* to couple to the watch module 10. Such strap connections 12*a*, 12*b* can be, for example, pin type connections between ends of straps 100*a*, 100*b* and the watch module 10. For example, strap connections 12*a*, 12*b* can comprise one or more holes in portions of the watch module 10 (for example, a body of the watch module 10) that receive ends of a pin, such as pin 403 shown in FIG. 6A) that can extend through holes in ends of straps 100*a*, 100*b*.

Watch module 10 can be similar or identical to any of those described in U.S. application Ser. No. 17/148,303, filed Jan. 13, 2021, and titled "Wearable Device with Physiological Parameters Monitoring", which is incorporated by reference herein in its entirety. Watch module 10 can include a physiological parameter measurement module 30 configured to measure an indication of the wearer's physiological parameters and/or characteristics, which can include, for example, pulse rate, respiration rate, SpO2, Pleth Variability Index (PVI), Perfusion Index (PI), Respiration from the pleth (RRp), hydration, and/or other parameters and/or characteristics. The physiological parameter measurement module 30 can include a skin-interfacing cover that encloses one or more or a plurality of emitters 31*a* (such as LEDs) and one or more detectors 31*b* (such as photodiodes). Such cover can include a plurality of lenses separated by a plurality of light barriers, for example, as described in U.S. application Ser. No. 17/148,303.

In some implementations, watch module 10 includes a module processor 35 (which can include a memory) for driving the emitter(s) 31*a* to emit light of different wavelengths and/or to process one or more signals responsive to attenuated light after absorption by the body tissue of the wearer from the detectors 31*b*. Optionally, the module processor 35 can also determine and output for display the physiological parameters based on the detected signals. Alternatively, the module 10 can send the signals from the detectors 31*b* (for example, preprocessed signals) to a device processor 22, which can determine and output for display the physiological parameters based on the detected signals. The absorption of light can be via reflectance and/or transreflectance by the wearer's body tissue, for example, by the pulsatile arterial blood flowing within a tissue site where the wearable device 1 is worn (for example, the wrist).

The emitter(s) 31*a* of the pulse oximeter module can be configured to emit a plurality of (for example, three, four, or more) wavelengths. The emitters 31*a* can be configured to emit light of a first wavelength providing an intensity signal that can act as a reference signal. The first wavelength can be more absorbent by the human body than light of other wavelengths emitted by the emitters 31*a*. The reference signal can be stronger and less likely to be affected by noise than the signals from other wavelengths emitted by the emitters 31*a*. The reference signal can be used by the module processor 35 to extract information from the other signals, for example, information relevant to and/or indicative of the pulsing rate, harmonics, or otherwise. The module processor 35 can focus the analysis on the extracted information for calculating physiological parameters of the wearer. The first wavelength can be from about 530 nm to about 650 nm, or from about 580 nm to about 585 nm, or from about 645 nm to about 650 nm, or about 580 nm, or about 645 nm. The light providing the reference signal can have an orange color. Alternatively, the light providing the reference signal can have a green color.

The emitters 31a can be configured to emit light having a second wavelength having a red color. The second wavelength can be from about 620 nm to about 660 nm. Light of the second wavelength can be more sensitive to changes in oxygen saturation (SpO2). The second wavelength is preferably closer to 620 nm, which results in greater absorption by the body tissue of the wearer, and therefore a stronger signal and/or a stepper curve in the signal, than a wavelength that is closer to 660 nm. The module processor 35 can extract information such as the pleth waveform from signals of the second wavelength.

The emitter(s) 31a can be configured to emit light having a third wavelength of about 900 nm to about 910 nm, or about 905 nm, or about 907 nm. The pulse oximeter processor can use the third wavelength as a normalizing wavelength when calculating ratios of the intensity signals of the other wavelengths.

Additionally or optionally, the emitters 31a can be configured to emit light having a fourth wavelength that is more sensitive to changes in water than the rest of the emitted wavelengths. The fourth wavelength can be about 970 nm. The module processor 35 can determine physiological parameters such as a hydration status of the wearer based at least in part on a comparison of the intensity signals of the fourth wavelength and a different wavelength detected by certain detectors 31b. The detectors 31b used for hydration monitoring, which will be described in greater detail below, can be located a predetermined distance away from the emitters 31a so that light travels through a certain depth of the tissue before being detected by those detectors 31b.

The watch module 10 can optionally include one or more thermistors 32 or other types of temperature sensors. The thermistor(s) 32 can be placed near one or more groups of emitters 31a. The thermistor(s) 32 can provide for wavelength correction of the light emitted by the emitters 31a. Optionally, the thermistor(s) 32 can additionally measure a temperature of the wearer of the wearable device 10. Optionally there can be one or more thermistors 32 located at other places of the watch module 10. The watch module 10 can include a gyroscope 36, an accelerometer 37, and/or other position and/or posture detection sensor(s). Optionally, the module processor 35, the gyroscope 36, and/or the accelerometer 37 can be located on a printed circuit board (PCB) 34 represented in FIG. 2 in dotted lines. The emitters 31a, the thermistor(s) 32, and/or the detectors 31b can also be positioned on the PCB 34 in some implementations.

As shown in FIG. 2, the watch module 10 can include its own device processor 22, which can be a digital/analog chip or other processor(s), such as a digital watch processor or a smartwatch processor. The watch module 10 can include a power source 24, which can be a battery, for powering the device processor 22, the display screen 20, and/or the pulse oximeter module 30. Optionally, the physiological parameter measurement module 30 can be preassembled before being integrated into the watch module 10. For example, a preassembled physiological parameter measurement module 30 can be secured within a device housing that includes two components releasably connected to each other using one or more screws or other fasteners. An electrical connection can be established between the pulse oximeter module PCB 34 and the circuit of the rest of the watch module 10, including for example, the device processor 22 and the display 20. Optionally, the electrical connection can include a flex circuit. The physiological parameter measurement module 30 can be characterized before being assembled with the rest of the watch module 10. Alternatively, a housing of the physiological parameter measurement module 30 can be an integral component of a housing of the watch module 10.

Optionally, as shown in FIG. 2, the watch module 10 can include an electrocardiogram (ECG) sensor including a plurality of electrodes 43, 45 configured to make contact with the wearer's skin. One or more ECG electrodes 45 may be located on and/or within the physiological parameter measurement module 30. One or more ECG electrodes 43 may be located elsewhere on the watch module 10 (for example, an ECG electrode 43 can form a part of a housing of the watch module 10. The ECG sensor can be in electrical communication with the module processor 35 via an ECG connector. Optionally, as shown in FIG. 2, the watch module 10 can include one or more other sensors 47, for example, one or more temperature sensors, a magnetometer, a moisture sensor, an impedance sensor, an acoustic sensor, among others.

With continued reference to FIG. 2, in some implementations, the watch module 10 includes a communication module 41. The communication module 41 can facilitate communicate (via wires and/or wireless connection) between the watch module 10 (and/or components thereof) and separate devices, such as separate monitoring and/or mobile devices. For example, the communication module 41 can be configured to allow the watch module 10 to wirelessly communicate with other devices, systems, and/or networks over any of a variety of communication protocols. The communication module 41 can be configured to use any of a variety of wireless communication protocols, such as Wi-Fi (802.11x), Bluetooth®, ZigBee®, Z-wave®, cellular telephony, infrared, near-field communications (NFC), RFID, satellite transmission, proprietary protocols, combinations of the same, and the like. The communication module 41 can allow data and/or instructions to be transmitted and/or received to and/or from the watch module 10 and separate computing devices. The communication module 41 can be configured to transmit (for example, wirelessly) processed and/or unprocessed physiological or other information to a separate computing devices, which can include, among others, a mobile device (for example, an iOS or Android enabled smartphone, tablet, laptop), a desktop computer, a server or other computing or processing device for display and/or further processing, among other things. Such separate computing devices can be configured to store and/or further process the received physiological and/or other information, to display information indicative of or derived from the received information, and/or to transmit information—including displays, alarms, alerts, and notifications—to various other types of computing devices and/or systems that may be associated with a hospital, a caregiver (for example, a primary care provider), and/or a user (for example, an employer, a school, friends, family) that have permission to access the subject's data. As another example, the communication module 41 can be configured to wirelessly transmit processed and/or unprocessed obtained physiological information and/or other information (for example, motion and/or location data) to a mobile phone which can include one or more hardware processors configured to execute an application that generates a graphical user interface displaying information representative of the processed or unprocessed physiological and/or other information. The communication module 41 can be and/or include a wireless transceiver.

In some implementations, the watch module 10 includes a strain gauge 26 that can be utilized to measure a pressure of the watch module 10 and/or wearable device 1 on the wearer. Strain gauge 26 can be similar or identical to that described in U.S. application Ser. No. 17/148,303.

Figure 3A:
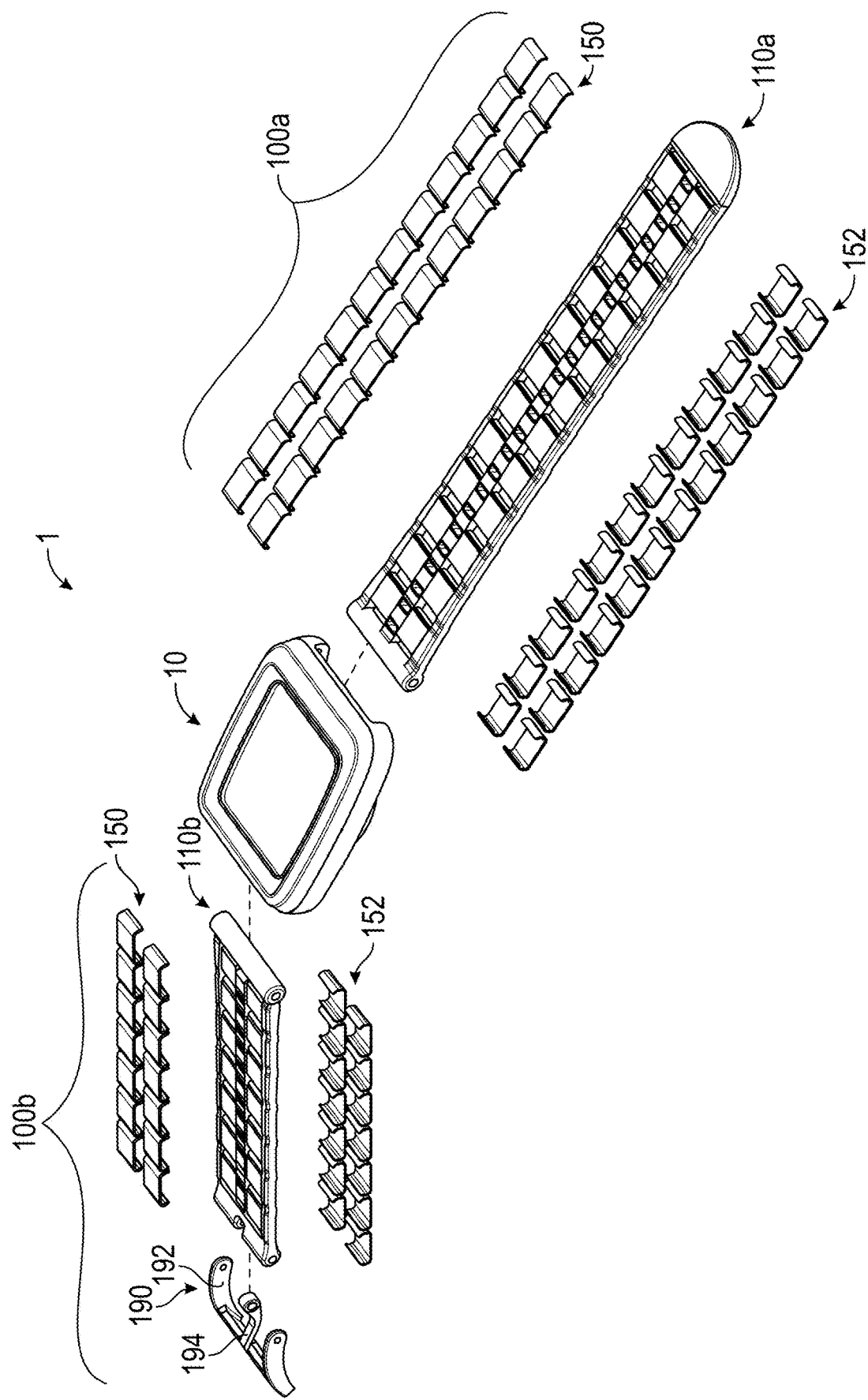
FIGS. 3A-3B illustrate exploded perspective views of the wearable device of FIGS. 1A-1C in accordance with aspects of this disclosure.
Figure 3B:
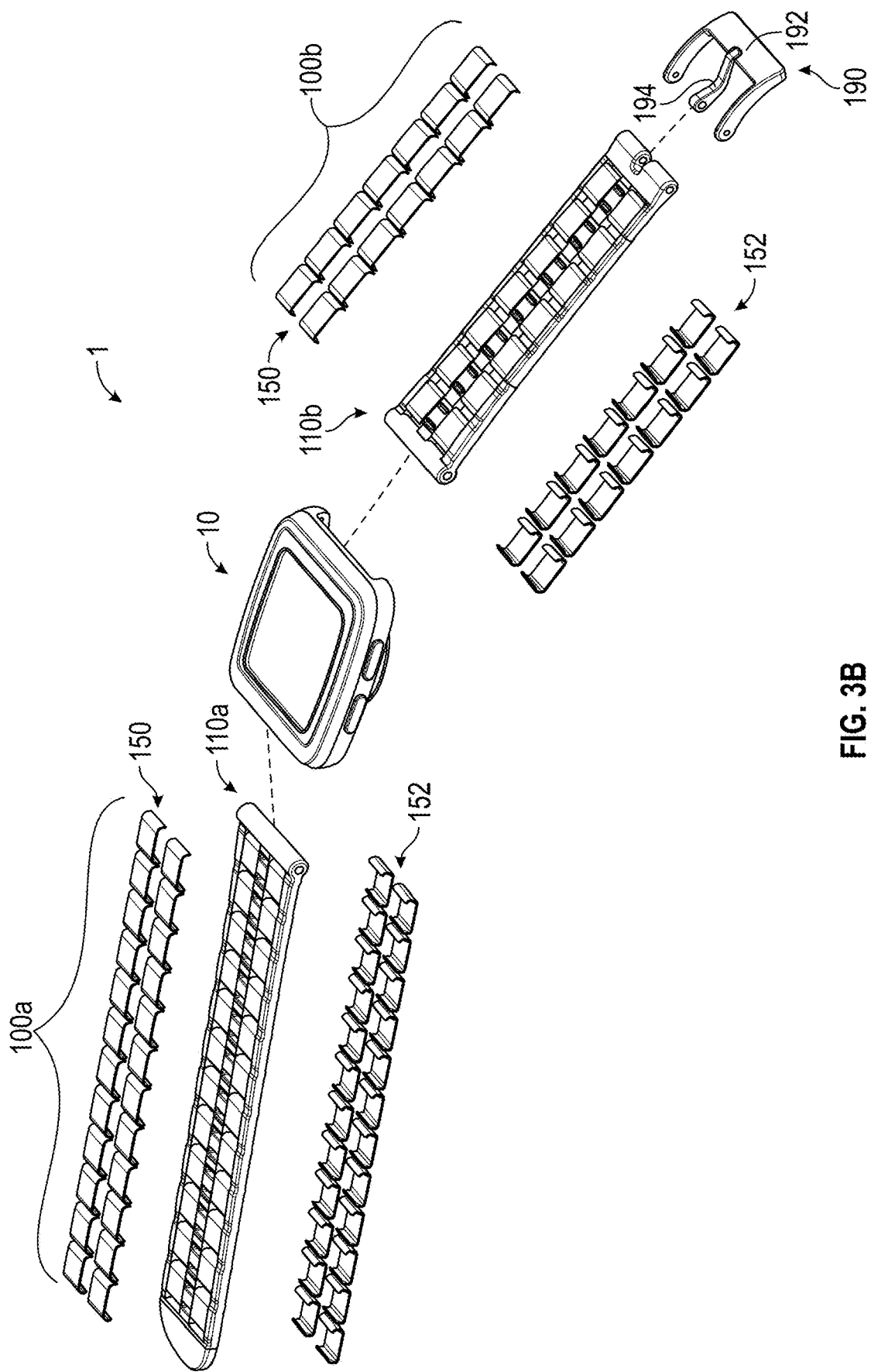
Figure 3C:
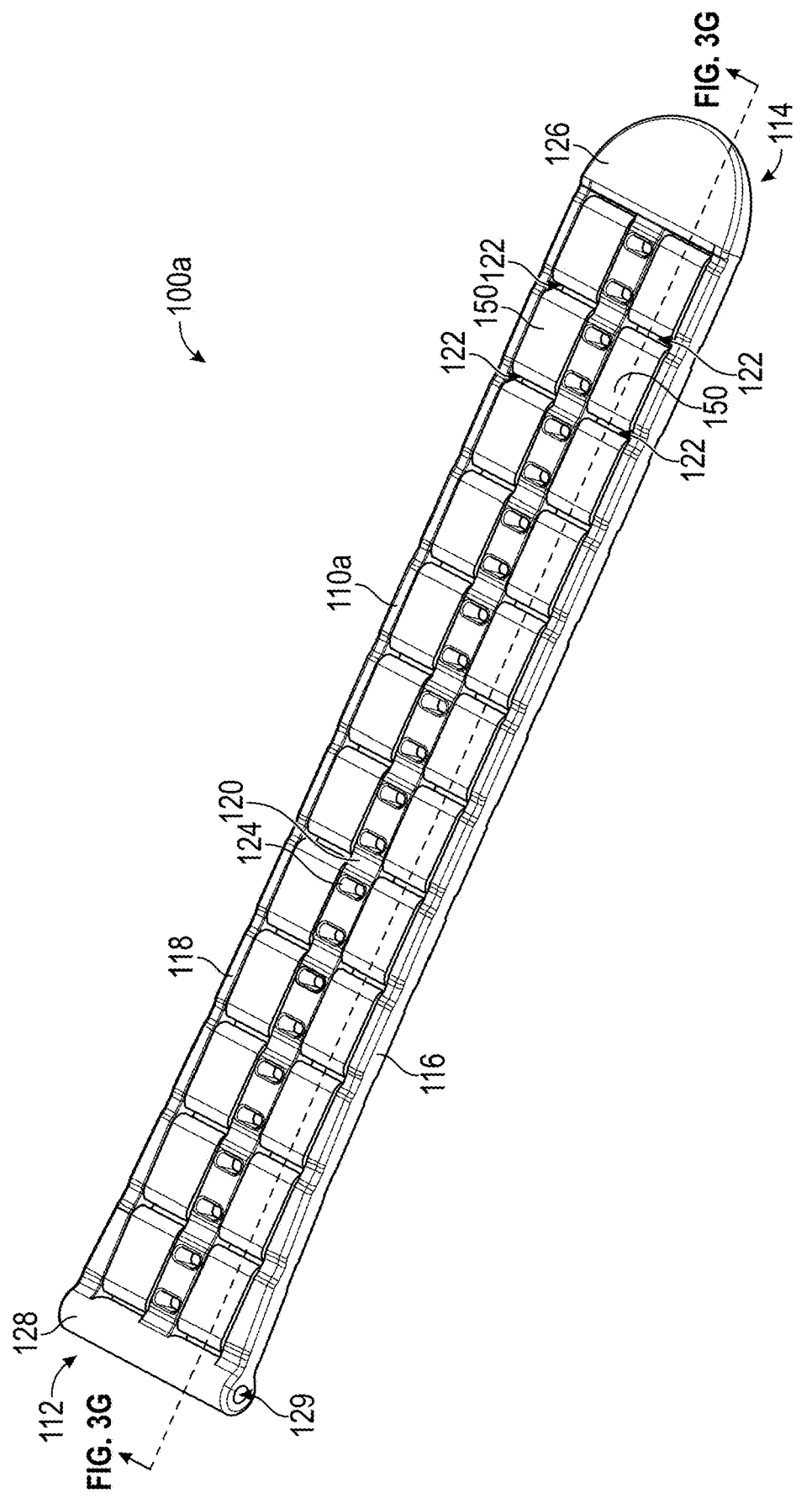
FIG. 3C illustrates a top perspective view of a strap of the wearable device of FIGS. 1A-1C in accordance with aspects of this disclosure.
Figure 3D:
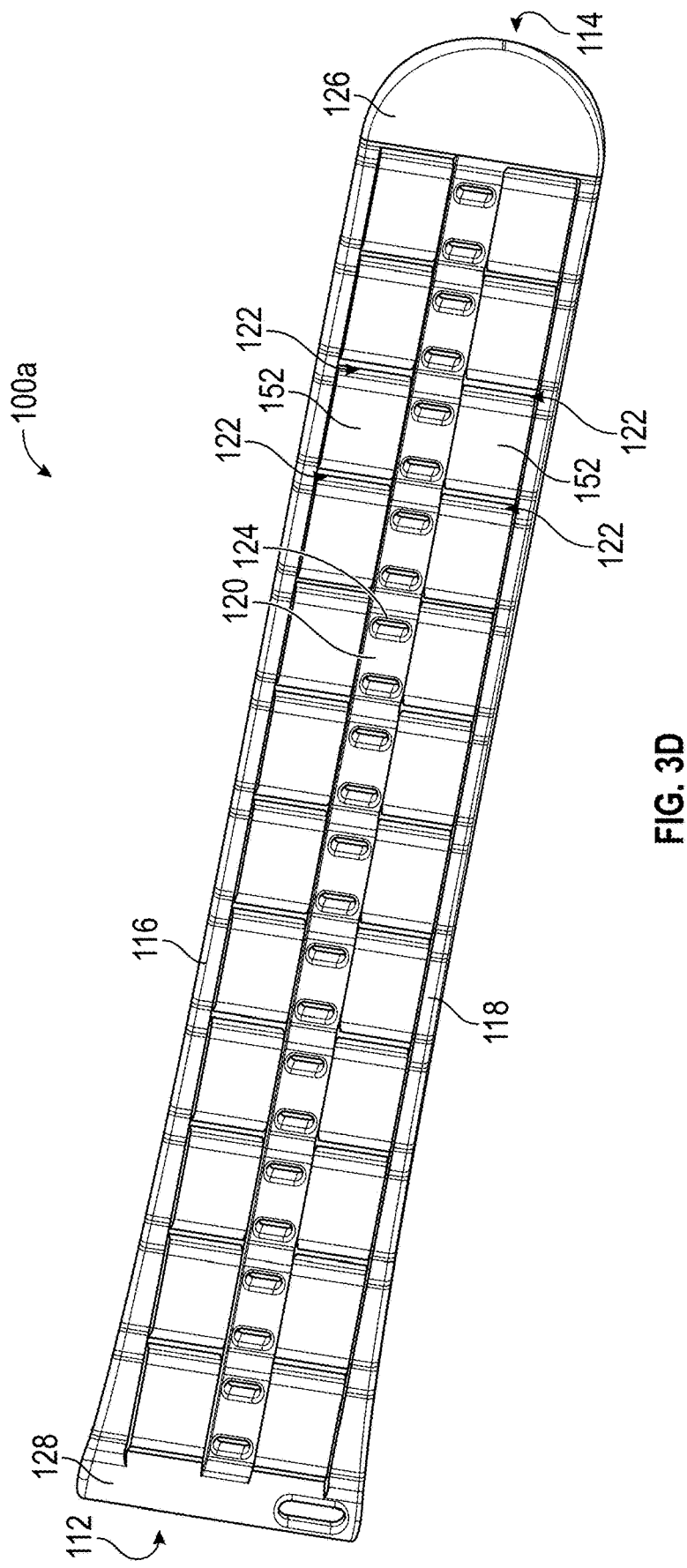
FIG. 3D illustrates a bottom perspective view of the strap of FIG. 3C in accordance with aspects of this disclosure.

FIGS. 3A-3B illustrate exploded perspective views of the wearable device 1 of FIGS. 1A-1C. As shown, the wearable device 1 can include strap 100*a*, strap 100*b*, watch module 10, and a buckle 190 that can include a buckle body 192 and tongue 194 as discussed above. Strap 100*a* and/or strap 100*b* can comprise more than one material. For example, strap 100*a* and/or strap 100*b* can comprise at least two materials. Strap 100*a* and/or strap 100*b* can comprise two materials with different material properties. For example, strap 100*a* and/or strap 100*b* can comprise two materials where one of the two materials is more pliable (for example, more stretchable) than the other.

With reference to FIGS. 3A-3B, strap 100*a* can comprise a base 110*a* (which may also be referred to as a "main body") and/or strap 100*b* can comprise a base 110*b* (which may also be referred to as a "main body"). In some implementations, base 110*a* and/or base 110*b* comprise a pliable (for example, stretchable) material. In some implementations, base 110*a* and/or base 110*b* only comprises one material, and such material can be pliable (for example, stretchable). For example, base 110*a* and/or base 110*b* can comprise an elastomeric material, such as rubber and/or silicone. In some implementations, base 110*a* and/or base 110*b* does not comprise a metallic material.

Each of strap 100*a* and/or strap 100*b* can include one or more or a plurality of strap members secured to portions of the base 110*a*, 110*b* along a length of the base 110*a*, 110*b*. Such strap members can be secured at various locations of the base 110*a*, 110*b*. For example, such strap members can be secured and/or operably positioned by the base 110*a*, 110*b* so as to contact skin of a wearer when the strap 100*a* and/or strap 100*b* is in use (for example, where the wearable device 1 is secured to a portion of the wearer's body). In some implementations, such strap members are secured to interior portions of the base 110*a*, 110*b*, for example, portions of the base 110*a*, 110*b* that are spaced away from edges and/or ends of the base 110*a*, 110*b*. Such strap members can comprise a material that is less pliable (for example, less stretchable) than a material that the base 110*a*, 110*b* is made of. For example, such strap members can comprise a metallic material, such as stainless steel. In some implementations, such strap members do not comprise an elastomeric material. In some implementations, such strap members do not comprise rubber and/or do not comprise silicone. In some implementations, such strap members do not comprise leather and/or do not comprise a fabric material. Such strap members can be non-integrally formed with one another (for example, separate from one another) and/or non-integrally formed with the base 110*a*, 110*b*. In some implementations, such strap members limit an ability of the base 110*a*, 110*b* to stretch, for example, along a width and/or length of the base 110*a*, 110*b* and/or along a direction of an axis that is parallel to the width and/or length of the base 110*a*, 110*b*. In some implementations, such strap members are smooth, thereby aiding user comfort when the strap 100*a*, 100*b* is in use and such strap members contact skin of the wearer. Such strap members can be, for example, channels 150, 152 which are discussed further below.

With continued reference to FIGS. 3A-3B, each of strap 100*a* and 100*b* can include one or more or a plurality of channels 150, 152. Channels 150, 152 can secure to portions of the base 110*a*, 110*b*, for example, as discussed further below. FIGS. 3A-3B illustrate exemplary amounts of channels 150, 152 and/or how channels 150, 152 can be arranged in rows and columns when secured to and/or operably positioned by the base 110*a*, 110*b*. The number and/or arrangement of channels 150, 152 can vary, for example, depending on characteristics of the strap 100*a*, 100*b*. For example, the number and/or arrangement of channels 150, 152 can vary depending on the length and/or width of the strap 100*a*, 100*b*, which can itself vary depending on an intended size of the strap (for example, small, medium, large, etc.) based on the wearer. Accordingly, illustrated number and/or arrangement of the channels 150, 152 is not intended to be limiting.

Channels 150, 152 can comprise a metallic material, such as stainless steel. In some implementations, channels 150, 152 only comprise a metallic material. In some implementations, channels 150, 152 do not comprise an elastomeric material. For example, in some implementations, channels 150, 152 do not comprise rubber and/or do not comprise silicone. In some implementations, channels 150, 152 do not comprise leather and/or do not comprise fabric.

With continued reference to FIGS. 3A-3B, an end of strap 100*a* can be secured to a portion of watch module 10 and/or an end of strap 100*b* can be secured to a portion of watch module 10. For example, an end of strap 100*a* can be secured to a portion of watch module 10 via a pin (for example, pin 403 shown in FIG. 6A) that can extend through an opening (for example, a through-hole such as hole 129 shown in FIG. 3C) at an end of base 110*a* which can secure to a portion of the watch module 10. Additionally or alternatively, an end of strap 100*b* can be secured to a portion of watch module 10 via a pin that can extend through an opening (for example, a through-hole) at an end of base 110*b* which can secure to a portion of the watch module 10. Such securement can allow the strap 100*a*, 100*b* (for example, base 110*a*, 110*b*) to rotate relative to watch module 10 and/or portions thereof which can allow the straps 100*a*, 100*b* to wrap around a portion of the wearer's body in some implementations.

FIGS. 3C-3K illustrate various portions of strap 100*a*. Any or all of the features of strap 100*a* discussed below can be applicable to strap 100*b*. For example, strap 100*b* can include channels 150, 152 discussed below with reference to strap 100*a*. In some implementations, strap 100*b* includes a different amount (for example, less) of the channels 150, 152 than does strap 100*a*, for example, where strap 100*a* is longer than strap 100*b*. As discussed above, strap 100*b* can be coupled with buckle 190, and in some implementations where strap 100*b* is coupled with buckle 190, strap 100*b* is shorter than strap 100*a*. In some implementations as can be seen in FIGS. 3A-3B, "free" ends of straps 100*a*, 100*b* (for example, ends which are not connected to watch module 10) are different from one another, such as where strap 100*b* is coupled with buckle 190 and where strap 100*a* include a tip 126 that can pass through the buckle 190 to facilitate size adjustment of the wearable device 1.

FIG. 3C illustrates a top perspective view of strap 100*a* and FIG. 3D illustrates a bottom perspective view of strap 100*a*. Strap 100*a* can include a first end 112, a second end 114 opposite the first end 112, a length extending between the ends 112, 114, and a width extending between sides of the strap 100*a*. Such ends 112, 114, length, width, and sides can be defined by the base 110*a* of the strap 100*a*.

FIG. 3E illustrates an exploded perspective view of strap 100*a* and FIG. 3F illustrates an exploded side view of strap 100*a*. FIG. 3G illustrates a cross-section taken through the strap 100*a* as shown in FIG. 3C, while FIG. 3H illustrates the strap 100*a* shown in FIG. 3G with channels 150, 152 removed so as to better illustrate portions of the base 110*a* which are described below. FIG. 3E illustrate exploded top and side perspective views of the strap 110a with channels 150, 152 spaced from (for example, disassembled from) base 110a.

Figure 6A:
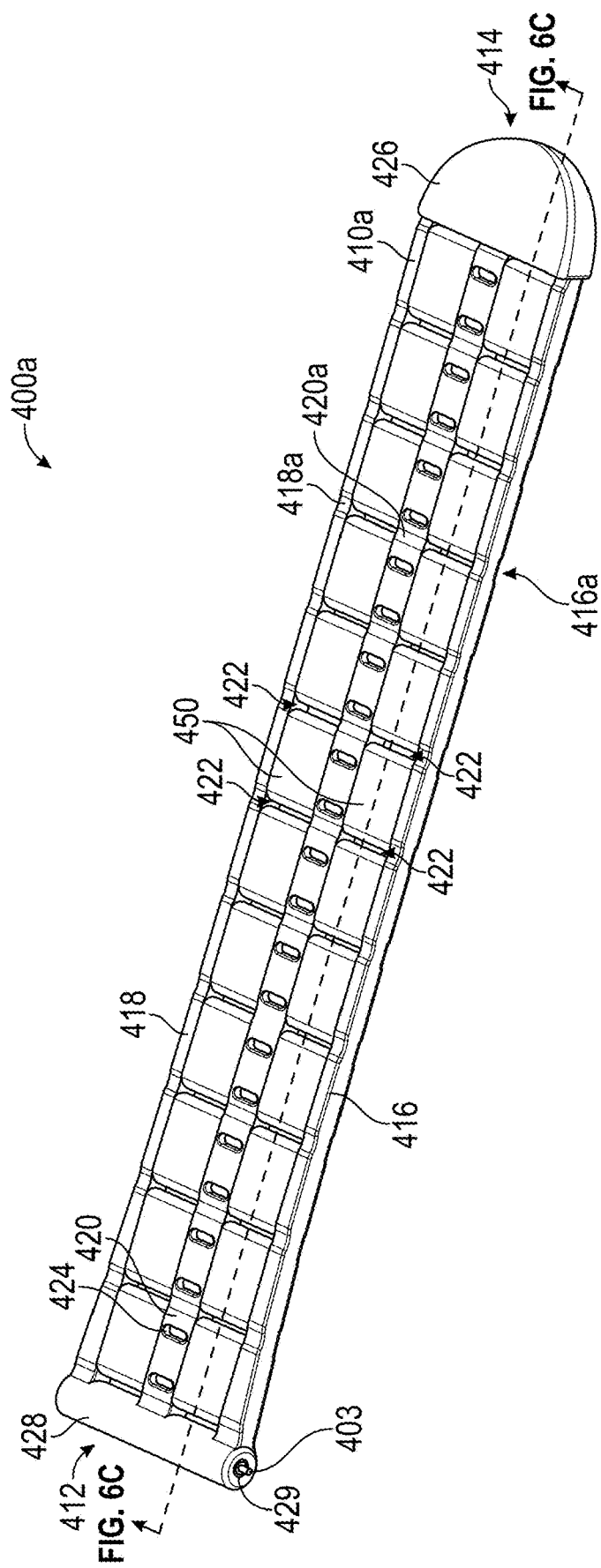
FIG. 6A illustrates a top perspective view of a strap in accordance with aspects of this disclosure.
Figure 6B:
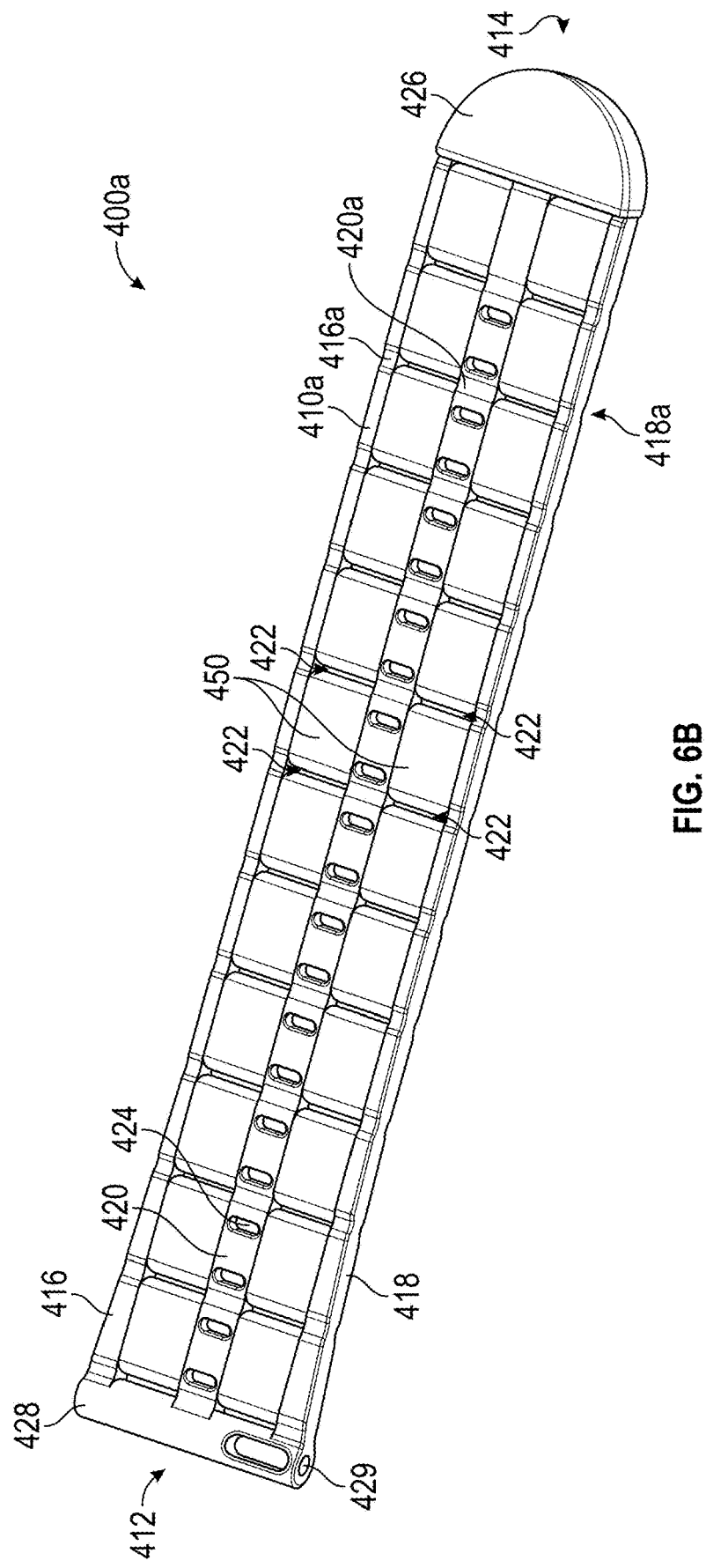
FIG. 6B illustrates a bottom perspective view of the strap of FIG. 6A in accordance with aspects of this disclosure.

With reference to at least FIGS. 3C-3D and 3E, base 110a can include first end 112, second end 114, and edge members 116, 118 that can extend between ends 112, 114 at and/or along sides of base 110a. Edge members 116, 118 can define the sides of the base 110a. As discussed previously, strap 100a can be configured to couple with a portion of watch module 10. Base 110a can include a coupling mechanism that can allow base 110a (and therefore strap 100a) to couple (for example, removably couple) to a portion of the watch module 10. For example, in some implementations, a portion of the base 110a is configured to receive a pin which can itself secure to a portion of the watch module 10. For example, the base 110a can include a coupling portion 128 that includes an opening 129 extending through at least a portion of the coupling portion 128, which is configured to receive a pin (such as pin 403 as shown in FIG. 6A) configured to secure to a portion of the watch module 10. Coupling portion 128 can extend at and/or along end 112 of the base 110a. Coupling portion 128 can extend along a portion (for example, an entirety) of a width of the base 110a. Opening 129 can extend along all or a portion of coupling portion 128. In some implementations, coupling portion 128 is rounded (for example, comprises an at least partially circular cross-section) and/or opening 129 comprises a circular cross-section. Coupling portion 128 can be connected to edge member 116, edge member 118, and/or spine member 120 (discussed further below).

In some implementations, base 110a includes a tip 126 at end 114, which can be opposite end 112 where the coupling portion 128 is located. Tip 126 can be configured to be inserted through an opening defined by buckle body 192, for example, when buckle body 192 is coupled to an end of strap 110b as described above. Tip 126 can be connected to edge member 116, edge member 118, and/or spine member 120.

In some implementations, base 110a includes one or more and/or a plurality of openings along a length and/or width, between ends 112, 114 and/or sides of the base 110a. For example, base 110a can include one, two, three, four, five, six, seven, eight, nine, ten, eleven, twelve, thirteen, fourteen, fifteen, sixteen, seventeen, eighteen, nineteen, or twenty or more openings. As another example, base 110a can include between one and a hundred openings, between ten and ninety openings, between twenty and eighty openings, between thirty and seventy openings, between forty and sixty openings, between ten and fifty openings, or between twenty and thirty openings, or any number of openings between any of these ranges, or any range bounded by any combination of values within these ranges. For example, with reference to FIG. 3H (which shows a cross-section taken through base 110a), base 110a can include one or more openings 122. Openings 122 can be spaced apart from one another along a length of the base 110a between ends 112, 114. For clarity, only some of the openings 122 are labeled in FIGS. 3C-3D and FIGS. 3G-3H. Base 110a can include one or more or a plurality of stems 130 that are positioned between and/or defined by (for example, defined at least partially by) openings 122. For example, base 110a can include one, two, three, four, five, six, seven, eight, nine, ten, eleven, twelve, thirteen, fourteen, fifteen, sixteen, seventeen, eighteen, nineteen, or twenty or more stems 130, and/or between one and a hundred, between ten and ninety, between twenty and eighty, between thirty and seventy, between forty and sixty, between ten and fifty, or between twenty and thirty stems 130, or any number of stems 130 between any of these ranges, or any range bounded by any combination of values within these ranges. Each of stems 130 can be spaced apart from one another by the openings 122. Each of the stems 130 can be positioned between two of the openings 122, for example, as shown. Advantageously, openings 122 can provide greater comfort to the wearer of a wearable device 1 including strap 110a by increasing breathability. Additionally, in some implementations, openings 122 can provide greater flexibility to band 110a, allowing band 110a to better wrap around a portion of the wearer's body.

In some implementations, base 110a includes a spine member 120. Spine member 120 can extend along the length of the base 110a and/or a portion of such length between ends 112, 114. For example, in some implementations of base 110a, spine member 120 extends between coupling portion 128 and tip 126. Spine member 120 can extend along an interior of base 110a. Spine member 120 can be spaced from (for example, inset from) edge member 116 and/or edge member 118. In some implementations, spine member 120 is parallel to edge member 116 and/or edge member 118. Spine member 120 can be separated from edge members 116, 118 by stems 130, for example, where stems 130 extend between edge members 116, 118 and spine member 120. In some implementations, stems 130 are transverse (for example, perpendicular) to edge member 116, edge member 118, and/or spine member 120.

Spine member 120 can include one or more or a plurality of openings 124 configured to facilitate securement of strap 100a to strap 100b. For clarity, only one of such openings 124 is labeled in FIGS. 3C-3D and 3G-3H. Spine member 120 can include one, two, three, four, five, six, seven, eight, nine, ten, eleven, twelve, thirteen, fourteen, fifteen, sixteen, seventeen, eighteen, nineteen, or twenty or more openings 124, and/or between one and a hundred, between ten and ninety, between twenty and eighty, between thirty and seventy, between forty and sixty, between ten and fifty, or between twenty and thirty openings 124, or any number of openings 124 between any of these ranges, or any range bounded by any combination of values within these ranges. Openings 124 can be sized and/or shaped to receive tongue 194 of buckle 190 to be positioned therethrough, thus allowing straps 100a, 100b to form a closed loop around a portion of a wearer's body (for example, wrist, arm, ankle, etc.). Inclusion of a plurality of openings 124 in spine member 120 can allow a size of such closed loop to be adjusted.

The number of stems 130 and/or openings 122 can vary and/or stems 130 and/or openings 122 can be arranged in one or more or a plurality of rows and one or more or a plurality of columns. For example, as shown in at least FIG. 3E, band 110a can include a plurality of stems 130 arranged in two columns and a plurality of rows. While FIG. 3E illustrates band 110a with a plurality of stems 130 arranged in two columns and twelve rows, the band 110a can include a different number and/or arrangement of stems 130. In some implementations such as that illustrated in the figures, band 110a can include two columns of stems 130 separated by spine member 120.

In some implementations, portions of the band 110a are configured to facilitate bending and/or flexing around a portion of the wearer's body when in use (for example, when the strap 100a is forming a closed loop around the portion of the wearer's body). For example, in some implementations, the edge member 116, edge member 118, and/or spine member 120 include one or more or a plurality of living hinges that facilitate bending of the band 110a. With reference to FIG. 3E, such living hinges can be defined by narrowing portions 116a, 118a, 120a in each of edge member 116, edge member 118, and spine member 120 (respectively). Edge member 116, edge member 118, and spine member 120 can include one, two, three, four, five, six, seven, eight, nine, ten, eleven, twelve, thirteen, fourteen, fifteen, sixteen, seventeen, eighteen, nineteen, or twenty or more of narrowing portions 116a, 118a, 120a, and/or between one and a hundred, between ten and ninety, between twenty and eighty, between thirty and seventy, between forty and sixty, between ten and fifty, or between twenty and thirty of narrowing portions 116a, 118a, 120a, or any number of narrowing portions 116a, 118a, 120a between any of these ranges, or any range bounded by any combination of values within these ranges. In some implementations, the number of narrowing portions 116a, 118a, 120a in edge member 116, edge member 118, and spine member 120 (respectively) corresponds to the number of openings 122 in band 110a. Narrowing portions 116a, 118a, 120a can be defined by a reduction in cross-sectional area along the edge member 116, edge member 118, and spine member 120. For example, narrowing portions 116a, 118a, 120a can be defined by a reduction in cross-sectional area caused by a varying height (which may also be referred to as "thickness") along the edge member 116, edge member 118, and spine member 120 (respectively). In some implementations, band 110a includes a plurality of triads of narrowing portions 116a, 118a, 120a, where each triad includes a narrowing portion 116a, a narrowing portion 118a, and a narrowing portion 120a. In some implementations, each of such triads are aligned with one another and/or aligned with one of openings 122.

Figure 3I:
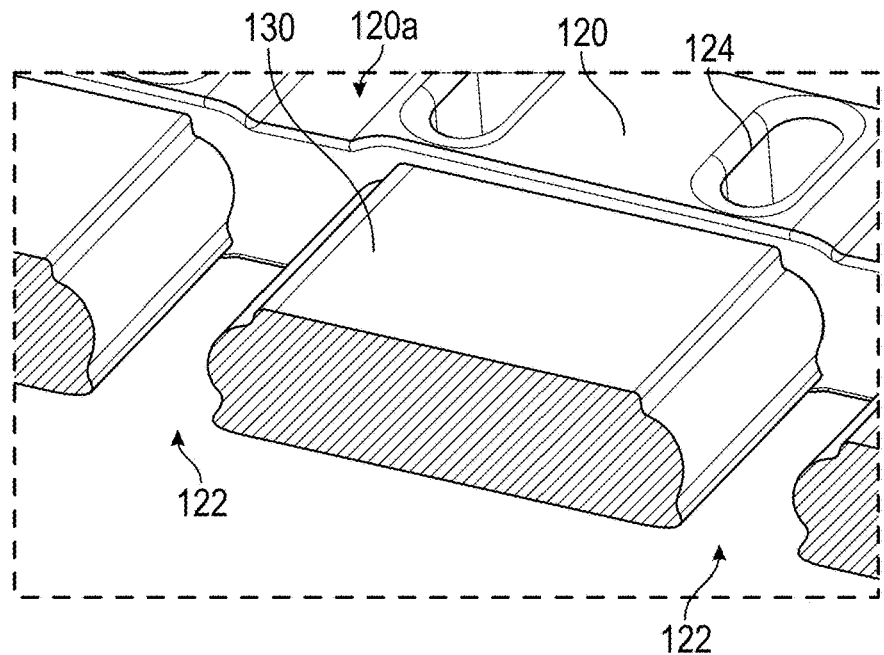
FIG. 3I illustrates an enlarged perspective view of a portion of the strap shown in FIG. 3H in accordance with aspects of this disclosure.
Figure 3J:
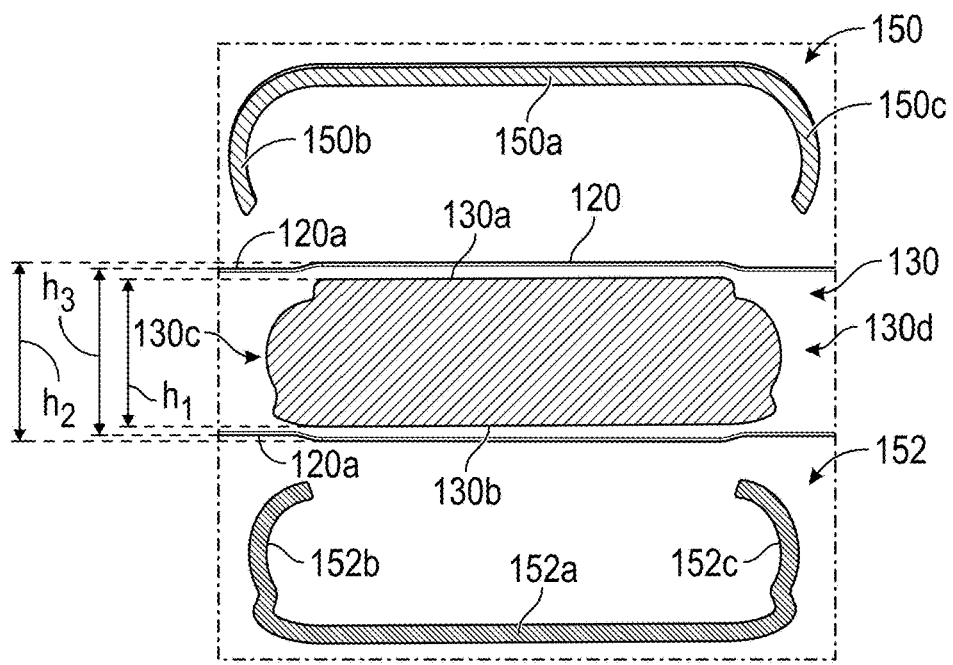
FIGS. 3J-3K illustrate enlarged cross-sectional views of portions of the strap of FIG. 3C in accordance with aspects of this disclosure.
Figure 3K:
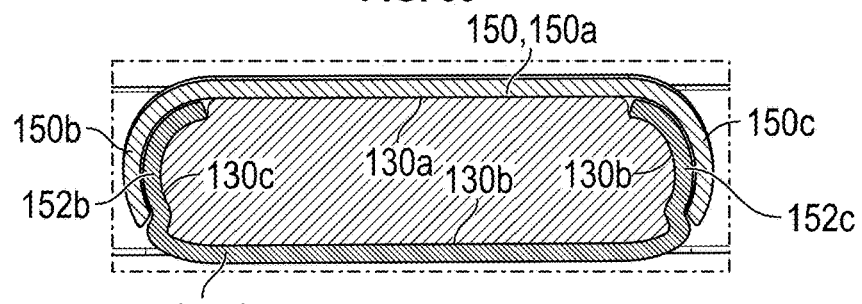

As mentioned previously, FIGS. 3E and 3F illustrate top and side exploded perspective views of strap 100a. FIGS. 3E-3F also illustrate channels 150, 152 detached from band 110a and FIG. 3G illustrates channels 150, 152 secured to band 110a (for example, secured to stems 130). FIG. 3I illustrates an enlarged view of a portion of the band 110a shown in FIG. 3H. More specifically, FIG. 3I illustrates an enlarged view of one of the stems 130 adjacent two openings 122. FIG. 3J shows an enlarged side view of a channel 150 and a channel 152 spaced from a stem 130 (for example, disassembled from stem 130), while FIG. 3K illustrates an enlarged side view of the channels 150, 152 secured to the stem 130.

Channel 150 can be sized and/or shaped to secure to and/or surround stem 130 or a portion thereof. In some implementations, channel 150 is configured to surround a portion of stem 130. In some implementations, channel 150 is configured to surround less than an entirety of a cross-section of stem 130. Channel 150 can include a web 150a and one or more legs extending from web 150a. For example, channel 150 can include one or both of legs 150b, 150c that can extend from web 150a. Legs 150b, 150c can extend transverse (for example, perpendicular to) web 150a. Legs 150b, 150c can extend from ends of web 150a, for example, opposing ends of web 150a. In some implementations, legs 150b, 150c are curved, for example, along all or a portion of lengths of legs 150b, 150b. In some implementations, legs 150b, 150c extend from web 150a and are curved toward each other. In some implementations, legs 150b, 150c are curved along an entirety of their lengths. In some implementations, web 150a comprises a greater length than one or both of legs 150b, 150c. Alternatively, in some implementations, web 150a has an equal or smaller length than one or both of legs 150b, 150c. In some implementations, web 150a is substantially planar. In some implementations, web 150a is not curved. In some implementations, channel 150 is C-shaped.

Channel 152 can be sized and/or shaped to secure to and/or surround stem 130 or a portion thereof. In some implementations, channel 152 is configured to surround a portion of stem 130. In some implementations, channel 152 is configured to surround less than an entirety of a cross-section of stem 130. Channel 152 can include a web 152a and one or more legs extending from web 152a. For example, channel 152 can include one or both of legs 152b, 152c that can extend from web 152a. Legs 152b, 152c can extend transverse (for example, perpendicular to) web 152a. Legs 152b, 152c can extend from ends of web 152a, for example, opposing ends of web 152a. In some implementations, legs 152b, 152c are curved, for example, along all or a portion of lengths of legs 152b, 152b. In some implementations, legs 152b, 152c extend from web 152a and are curved toward each other. In some implementations, legs 152b, 152c comprise notches 152d, 152e at and/or near where legs 152b, 152c connect to web 152a. Notches 152d, 152e can be sized and/or shaped to be accommodated by portions of sides 130c, 130d of stem 130 as discussed in more detail below. In some implementations, legs 152b, 152c are sized and/or shaped to be accommodated by sides 130c, 130d of stem 130 such that outer portions (for example, outer surfaces) of legs 152b, 152c form a rounded shape when positioned adjacent a top portion 130a of stem 130 as explained in more detail below. In some implementations, legs 152b, 152c comprise a continuous curve along only a portion of their lengths. For example, in some implementations where legs 152b, 152c comprise notches 152d, 152e, legs 152b, 152c comprise a continuous curve from the notches 152d, 152e to a free end of the legs 152b, 152c. In some implementations, web 152a comprises a greater length than one or both of legs 152b, 152c. Alternatively, in some implementations, web 152a has an equal or smaller length than one or both of legs 152b, 152c. In some implementations, web 152a is substantially planar. In some implementations, web 152a is not curved. In some implementations, channel 152 is C-shaped.

With reference to FIG. 3J, stem 130 can include a top portion 130a, a bottom portion 130b opposite the top portion 130a, and sides 130c, 130d. Bottom portion 130b can face toward skin of the wearer and/or be positioned closer to skin of the wearer than top portion 130a when the strap 100a is in use, for example, with a wearable device 1 when secured to the wearer. Top portion 130a can face away from skin of the wearer and/or be positioned farther from skin of the wearer than bottom portion 130b when the strap 100a is in use. With reference to FIGS. 3J-3K, sides 130c, 130d can be configured to accommodate a size and/or shape of legs 152b, 152c of channel 152 such that, when channel 152 is secured to stem 130 and legs 152b, 152c are positioned adjacent to and/or contact sides 130c, 130d, free ends of legs 152b, 152c and top portion 130a cooperate to form a generally smooth transition. For example, an outer surface of legs 152b, 152c at free ends of legs 152b, 152c can be substantially flush with an outer surface of top portion 130a. A gap between the top portion 130a and free ends of legs 152b, 152c can be less than approximately 0.2 inch, less than approximately 0.1 inch, less than approximately 0.05 inch, less than approximately 0.01 inch, or less than approximately 0.005 inch, for example, in some implementations.

In some implementations, legs 152b, 152c of channel 152 are configured to accommodate and/or secured adjacent to legs 150b, 150c of channel 150 (for example, when secured to and/or around stem 130) such that channel 150 and channel 152 cooperate to form a generally rounded shape. In some implementations, notches 152d, 152e are configured to allow free ends of legs 150b, 150c of channel 150 to meet web 152a of channel 152 and form a generally smooth transition. In some implementations, an outer surface of legs 150b, 150c at free ends of legs 150b, 150c is substantially flush with an outer surface of web 152a. A gap between the top web 152a and free ends of legs 150b, 150c can be less than approximately 0.2 inch, less than approximately 0.1 inch, less than approximately 0.05 inch, less than approximately 0.01 inch, or less than approximately 0.005 inch, for example, in some implementations. With continued reference to FIG. 3K, in some implementations, when channels 150, 152 secure to stem 130 (and/or to one another), channels 150, 152 and/or stem 130 can form a generally rounded shape, for example, an oblong shape.

Channel 150 and/or channel 152 can surround less than an entirety of stem 130 when secured thereto and/or when secured to one another. In some implementations, channel 150 and/or channel 152 surrounds less than approximately 90%, less than approximately 80%, less than approximately 70%, or less than approximately 60% of a perimeter of a cross-section of stem 130 when secured to stem 130. Additionally or alternatively, in some implementations, channel 150 and/or channel 152 surrounds at least approximately 10%, at least approximately 20%, at least approximately 30%, at least approximately 40%, at least approximately 50%, at least approximately 60%, at least approximately 70%, or at least approximately 80% of a perimeter of a cross-section of stem 130 when secured to stem 130.

When channels 150, 152 are secured to stem 130 and/or each other, portions of channels 150, 152 can overlap one another. For example, in some implementations, when channels 150, 152 are secured to stem 130, portions of channel 150 overlap portions of channel 152. As another example, in some implementations, when channels 150, 152 are secured to stem 130, one or both of legs 150b, 150c of channel 150 overlap one or both of legs 152b, 152c of channel 152. In some implementations, only the legs 150b, 150c of channel 150 overlap portions of channel 152 (for example, legs 152b, 152c). In some implementations, legs 152b, 152c are sandwiched between sides 130c, 130d of stem 130 and legs 150b, 150c when channels 150, 152 are secured to stem 130. In some implementations, overlapping portions of channels 150, 152 (for example, legs 150b, 150c, 152b, 152c) and non-overlapping portions of channels 150, 152 (for example, webs 150a, 152a) form a generally rounded shape when secured to one another and/or around stem 130. Such generally rounded shape can be, for example, an oblong shape. In some implementations, stem 130, channel 150, and channel 152 cooperate to form a generally rounded shape (for example, an oblong shape) when secured to one another. For example, in some implementations, sides 130c, 130d, overlapping portions of channels 150, 152 (for example, legs 150b, 150c, 152b, 152c) and non-overlapping portions of channels 150, 152 (for example, webs 150a, 152a) form a generally rounded shape when channel 150, channel 152, and stem 130 are secured to one another.

With continued reference to FIG. 3J, in some implementations, stems 130 have a height $h_1$ that is smaller than a height $h_2$ of the spine member 120. Heights $h_1$ and $h_2$ can be orthogonal to a length of the strap 100a extending between ends 112, 114 of the strap 100a (see, for example, FIG. 3C) and/or heights $h_1$ and $h_2$ can be orthogonal to a width of the strap 100a (and/or base 110a) extending from sides of the strap 100a (which can be defined by edge members 116, 118). Heights $h_1$ and $h_2$ can be also be referred to as thicknesses of stems 130 and spine member 120, respectively. As shown in FIG. 3J and as discussed previously, spine member 120 can include narrowing portions 120a which can be defined by a height $h_3$. Height $h_3$ can be smaller than height $h_2$. Height $h_3$ can be greater than or equal to height $h_1$.

Strap 100a can be manufactured and/or assembled in a variety of ways. In some implementations, band 110a is formed via a molding (for example, injection molding) process. For example, ends 112, 114, edge members 116, 118, spine member 120, stems 130, tip 126, and/or coupling portion 128 can be formed via injection molding of a material, for example, an elastomeric material. Such elastomeric material can comprise silicone and/or rubber, for example. Such molding process can be utilized to form openings 124, openings 122, and/or opening 129, all of which are discussed elsewhere herein. Channels 150, 152 can be formed of a metallic material (for example, via an extrusion process). As discussed previously, channels 150, 152 can comprise stainless steel. In some implementations, channels 150, 152 only comprise a metallic material. In some implementations, the number of channels 150 and channels 152 corresponds to the number of stems 130 in base 110a. After the channels 150, 152 are formed, channels 150, 152 can be secured to stems 130 of base 110, for example, as shown in FIGS. 3G and 3K. For example, channel 152 can be secured around at least a portion of stem 130, and, thereafter, channel 150 can be secured around at least a portion of stem 130 and at least a portion of channel 152. In some implementations, channel 150 and/or channel 152 can be snapped into engagement around stem 130 and/or with each other. In some implementations, channels 150, 152 are configured and/or are secured to stem 130 so as to be removably attachable by a user (for example, a wearer of a wearable device 1 including strap 100a). Alternatively, in some implementations, channels 150, 152 are configured and/or are secured to stem 130 so as to be not removably attachable by a user (for example, a wearer of a wearable device 1 including strap 100a).

FIGS. 4A-4F illustrate a strap 200a. Strap 200a can be utilized with wearable device 1 and/or watch module 10 in a similar or identical manner as that described elsewhere herein with reference to strap 100a. Further, wearable device 1 can include two straps that are include some, many, or all of the features described below with respect to strap 200a, for example, so that the wearable device 1 can be secured around a portion of a wearer's body with two straps 200a. Strap 200a can be similar or identical to strap 100a in some or many respects. With reference to at least FIGS. 4A-4B, strap 200a can include a base 210a (which may also be referred to as a "main body"), an end 212, end 214, a length extending between ends 212, 214, sides which can include and/or be defined by edge members 216, 218, a tip 226 at or near end 214, and/or a coupling portion 228 including an opening 229 at or near end 212. End 212, end 214, edge members 216, 218, tip 226, coupling portion 228, and/or opening 229 can be similar or identical to end 112, end 114, edge members 116, 118, tip 126, coupling portion 128, and/or opening 129 described above with reference to strap 100a Similar to strap 100a, strap 200a can comprise more than one material. For example, strap 200a can comprise at least two materials. Strap 200a can comprise two materials with different material properties. For example, strap 200a can comprise two materials where one of the two materials is more pliable (for example, more stretchable) than the other. In some implementations, base 210a comprise a pliable (for example, stretchable) material. In some implementations, base 210a only comprises one material, and such material can be pliable (for example, stretchable). For example, base 210a can comprise an elastomeric material, such as rubber and/or silicone. In some implementations, base 210a does not comprise a metallic material.

Similar to strap 100a, strap 200a can include one or more or a plurality of strap members secured to portions of the base 210a along a length of the base 210a and which can be secured at various locations of the base 210a. Such strap members can comprise a material that is less pliable (for example, less stretchable) than a material that the base 210a is made of. For example, such strap members can comprise a metallic material, such as stainless steel. In some implementations, such strap members do not comprise an elastomeric material. In some implementations, such strap members do not comprise rubber and/or do not comprise silicone. In some implementations, such strap members do not comprise leather and/or do not comprise a fabric material. Such strap members can be non-integrally formed with one another (for example, separate from one another) and/or non-integrally formed with the base 210a. In some implementations, such strap members limit an ability of the base 210a to stretch, for example, along a width and/or length of the base 210a and/or along a direction of an axis that is parallel to the width and/or length of the base 210a. Such strap members can be, for example, channels 250. Strap 200a can include one or more or a plurality of channels 250.

FIGS. 4C-4D illustrate exemplary amounts of channels 250 and/or how channels 250 can be arranged in rows and columns when secured to and/or operably positioned by the base 210a. The number and/or arrangement of channels 250 can vary, for example, depending on characteristics of the strap 200a. For example, the number and/or arrangement of channels 250 can vary depending on the length and/or width of the strap 200a, which can itself vary depending on an intended size of the strap (for example, small, medium, large, etc.) based on the wearer. Accordingly, illustrated number and/or arrangement of the channels 250 is not intended to be limiting. Channels 250 can comprise a metallic material, such as stainless steel. In some implementations, channels 250 only comprise a metallic material. In some implementations, channels 250 do not comprise an elastomeric material. For example, in some implementations, channels 250 do not comprise rubber and/or do not comprise silicone. In some implementations, channels 250 do not comprise leather and/or do not comprise fabric.

Base 210a can include one or more and/or a plurality of openings 222 along a length and/or width, between ends 212, 214 and/or sides of the base 210a. With reference to FIG. 4B, the number and/or arrangement of openings 222 can vary and/or the number of openings 222 can be equal to the values discussed above with reference to base 110a, for example. Openings 222 can be spaced apart from one another along a length of the base 210a between ends 212, 214. For clarity, only some of the openings 222 are labeled in FIGS. 4A-4C. Base 210a can include one or more or a plurality of stems 230 that are positioned between and/or defined by (for example, defined at least partially by) openings 222. The number and/or arrangement of stems 230 can vary and the number of stems 230 can be equal to the values discussed above with reference to base 110a, for example. Each of stems 230 can be spaced apart from one another by the openings 222. Each of the stems 230 can be positioned between two of the openings 222, for example, as shown. Openings 222 can provide benefits similar or identical to those discussed above with respect to openings 122.

Base 210a can include a spine member 220 which may be similar or identical to spine member 120 in some or many respects. Spine member 220 can extend along the length of the base 210a and/or a portion of such length between ends 212, 214. For example, in some implementations of base 210a, spine member 220 extends between coupling portion 228 and tip 226. Spine member 220 can extend along an interior of base 210a. Spine member 220 can be spaced from (for example, inset from) edge member 216 and/or edge member 218. In some implementations, spine member 220 is parallel to edge member 216 and/or edge member 218. Spine member 220 can be separated from edge members 216, 218 by stems 230, for example, where stems 230 extend between edge members 216, 218 and spine member 220. In some implementations, stems 230 are transverse (for example, perpendicular) to edge member 216, edge member 218, and/or spine member 220. Spine member 220 can include one or more or a plurality of openings 224 which can be similar or identical to openings 124 described above with reference to spine member 120. For clarity, only some of the openings 124 are labeled in FIGS. 4A-4C. The number and/or arrangement of openings 224 can vary and the number of openings 224 can be equal to the values discussed above with reference to spine member 120, for example.

The number of stems 230 and/or openings 222 can vary, and stems 130 and openings 222 can be arranged in one or more or a plurality of rows and one or more or a plurality of columns, for example, similar to as discussed with reference to stems 130 and openings 122 above. With reference to FIG. 4B, in some implementations, bottom surfaces of stems 230 and spine member 220 extend and/or are defined along a common plane or surface which defines a bottom surface of base 210a.

Band 210a (and/or portions thereof) can be configured to facilitate bending and/or flexing around a portion of the wearer's body when in use in a similar or identical manner as that discussed above with reference to band 110a. For example, edge member 216, edge member 218, and/or spine member 220 can include one or more or a plurality of living hinges that facilitate bending of the band 210a. Such living hinges can be defined by narrowing portions 216a, 218a, 220a in each of edge member 216, edge member 218, and spine member 220 (respectively). Narrowing portions 216a, 218a, 220a can be similar or identical to narrowing portions 116a, 118a, 120a discussed above with reference to edge member 116, edge member 118, and spine member 120 and the number of narrowing portions 216a, 218a, 220a can be similar to those discussed above with reference to edge member 116, edge member 118, and spine member 120.

Figure 4A:
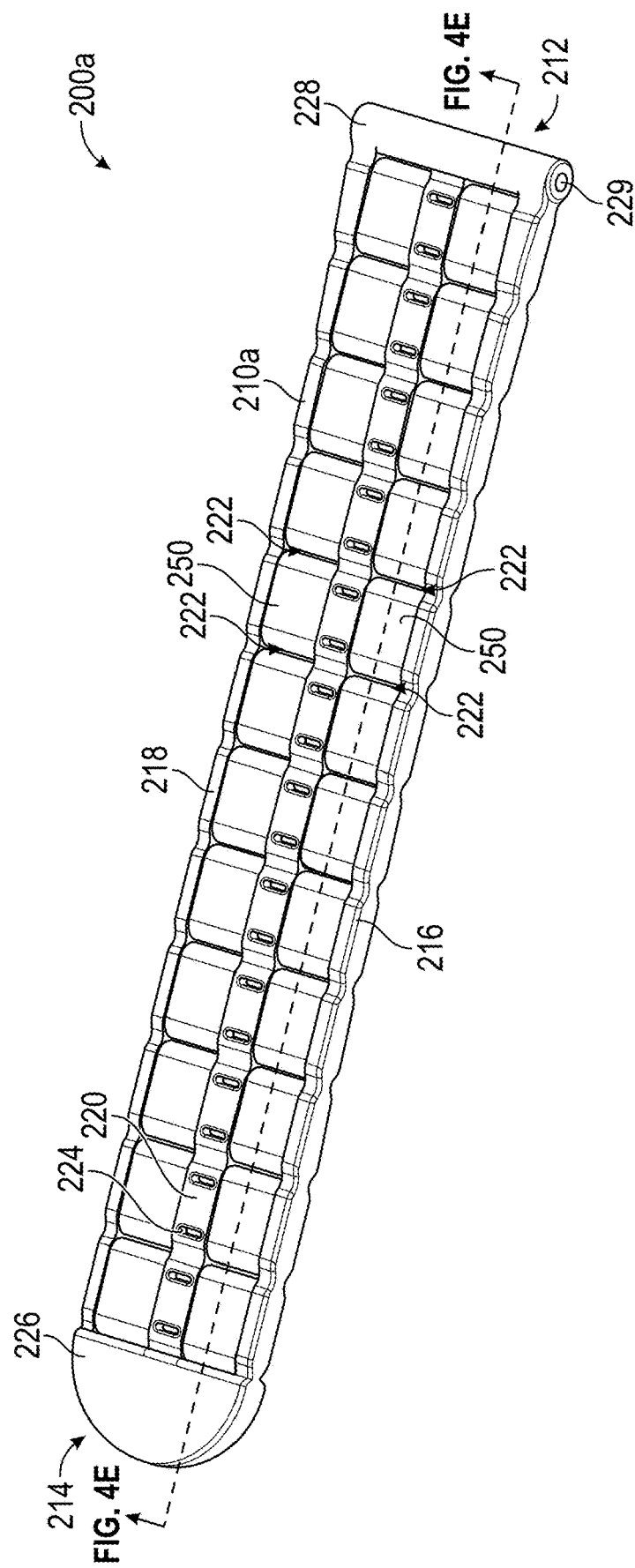
FIG. 4A illustrates a top perspective view of a strap in accordance with aspects of this disclosure.
Figure 4B:
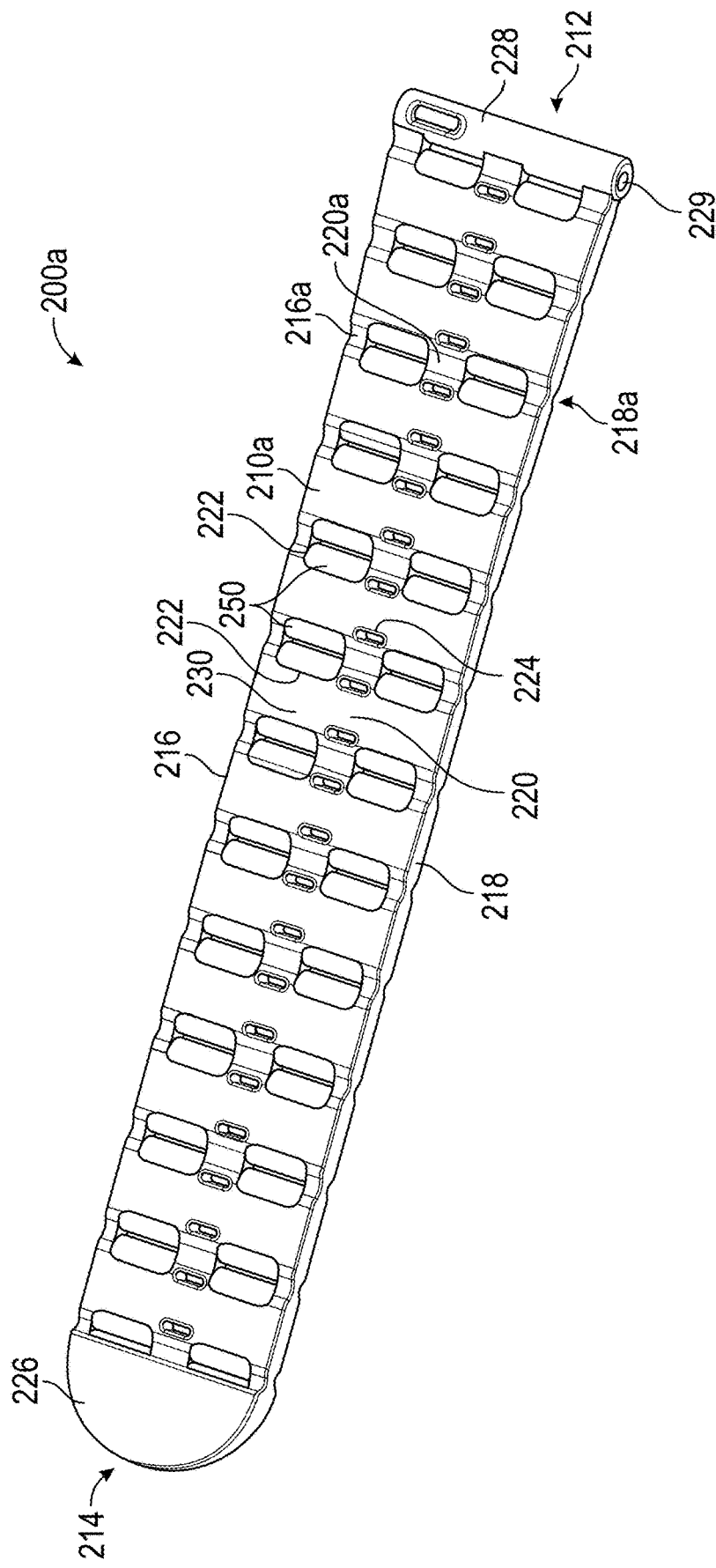
FIG. 4B illustrates a bottom perspective view of the strap of FIG. 4A in accordance with aspects of this disclosure.

FIGS. 4C and 4D illustrate top and side exploded perspective views of strap 200a. FIGS. 4C-4D also illustrate channels 250 detached (for example, disassembled) from base 210a. FIG. 4E illustrates a cross-section taken through strap 200a as shown in FIG. 4A and further illustrates channels 250 secured to base 210a (for example, secured to stems 230). FIG. 4F illustrates an enlarged side view of a channel 250 secured to a stem 230.

Channel 250 can be sized and/or shaped to secure to and/or surround stem 230 or a portion thereof. In some implementations, channel 250 is configured to surround a portion of stem 230. In some implementations, channel 250 is configured to surround less than an entirety of a cross-section of stem 230. Channel 250 can include a web 250a and one or more legs extending from web 250a. For example, channel 250 can include one or both of legs 250b, 250c that can extend from web 250a. Legs 250b, 250c can extend transverse (for example, perpendicular to) web 250a.

Legs 250b, 250c can extend from ends of web 250a, for example, opposing ends of web 250a. In some implementations, legs 250b, 250c are curved, for example, along all or a portion of lengths of legs 250b, 250c. In some implementations, legs 250b, 250c extend from web 250a and are curved toward each other. In some implementations, legs 250b, 250c are curved along an entirety of their lengths. In some implementations, web 250a comprises a greater length than one or both of legs 250b, 250c. Alternatively, in some implementations, web 250a has an equal or smaller length than one or both of legs 250b, 250c. In some implementations, web 250a is substantially planar. In some implementations, web 250a is not curved. In some implementations, channel 250 comprises a C-shape.

With reference to at least FIG. 4F, stem 230 can include a top portion 230a, a bottom portion 230b opposite the top portion 230a, and sides 230c, 230d. When the strap 200a is in use, for example when a wearable device 1 is secured to a user, bottom portion 230b can face toward skin of the wearer and/or be positioned closer to skin of the wearer than top portion 230a, and top portion 230a can face away from skin of the wearer and/or be positioned farther from skin of the wearer than bottom portion 230b. Top portion 230a and sides 230c, 230d can be configured to accommodate a size and/or shape of web 250a and legs 250b, 250c of channel 250 such that, when channel 250 is secured to stem 230, web 250a is positioned adjacent to and/or contact the top portion 230a and legs 250b, 250c are positioned adjacent to and/or to contact sides 230c, 230d. Bottom portion 230b can be configured to accommodate a size and/or shape of ends of legs 250b, 250c such that, when channel 250 is secured to stem 230, ends of legs 250b, 250c are positioned adjacent to and/or contact bottom portion 230b. Bottom portion 230b and ends of legs 250b, 250c can cooperate to form a generally smooth transition. For example, an outer surface of ends of legs 250b, 250c can be substantially flush with an outer surface of bottom portion 230b. In some implementations, a distance by which the bottom portion 230b extends (for example, downward) from a remaining portion of the stem 230 a distance that is substantially equal to a thickness of leg 250b and/or leg 250c such that outer surfaces of the bottom portion 230b and the legs 250b, 250c are substantially flush. In some implementations, ends of legs 250b, 250c are separated by a gap $G_1$ which can be substantially equal to a width of the bottom portion 230b.

Channel 250 can surround less than an entirety of stem 230 when secured thereto. In some implementations, channel 250 surrounds less than approximately 90%, less than approximately 80%, less than approximately 70%, or less than approximately 60% of a perimeter of a cross-section of stem 230 when secured to stem 230. Additionally or alternatively, in some implementations, channel 250 surrounds at least approximately 10%, at least approximately 20%, at least approximately 30%, at least approximately 40%, at least approximately 50%, at least approximately 60%, at least approximately 70%, or at least approximately 80% of a perimeter of a cross-section of stem 230 when secured to stem 230.

In some implementations, when channel 250 secures to stem 230, channel 250 and stem 230 can form a generally rounded shape, for example, an oblong shape. In some implementations, channel 250 is formed to include gap $G_1$ and channel 250 can be flexed (for example temporarily flexed) to allow the channel 250 to be positioned around and/or secured to stem 230. In some implementations, channel 250 can be snapped into engagement around stem 230.

Strap 200a can be manufactured and/or assembled in a variety of ways. In some implementations, band 210a is formed via a molding (for example, injection molding) process. For example, ends 212, 214, edge members 216, 218, spine member 220, stems 230, tip 226, and/or coupling portion 228 can be formed via injection molding of a material, for example, an elastomeric material. Such elastomeric material can comprise silicone and/or rubber, for example. Such molding process can be utilized to form openings 224, openings 222, and/or opening 229. Channels 250 can be formed of a metallic material (for example, via an extrusion process). As discussed previously, channels 250 can comprise stainless steel. In some implementations, channels 250 only comprise a metallic material. In some implementations, the number of channels 250 corresponds to the number of stems 230 in base 210a. After the channels 250 are formed, channels 250 can be secured to stems 230 of base 210a. In some implementations, channels 250 are configured and/or are secured to stem 230 so as to be removably attachable by a user (for example, a wearer of a wearable device 1 including strap 200a). Alternatively, in some implementations, channels 250 are configured and/or are secured to stem 230 so as to be not removably attachable by a user (for example, a wearer of a wearable device 1 including strap 200a).

FIGS. 5A-5F illustrate a strap 300a. Strap 300a can be utilized with a wearable device 1 and/or a watch module 10 in a similar or identical manner as that described elsewhere herein with reference to strap 100a. Strap 300a can be similar or identical to strap 100a in some or many respects. With reference to at least FIGS. 5A-5B, strap 300a can include a base 310a (which may also be referred to as a "main body"), an end 312, an end 314 opposite end 312, a length extending between ends 312, 314, sides that can include and/or be defined by edge members 316, 318, a tip 326 at or near end 314, and/or a coupling portion 328 including an opening 329 at or near end 312. End 312, end 314, edge members 316, 218, tip 326, coupling portion 328, and/or opening 329 can be similar or identical to end 112, end 114, edge members 116, 118, tip 126, coupling portion 128, and/or opening 129 described above with reference to strap 100a. Base 310a can be similar or identical to base 110a in some or many respects. For example, base 310a can include one or more and/or a plurality of openings 322 that can be similar or identical to openings 122 discussed above with respect to base 110a. As another example, base 310a can include a spine member 320 which can be similar or identical to spine member 120 discussed above. Spine member 320 can include one or more of a plurality of openings 324 that can be similar or identical to openings 324, and the number of openings 324 in spine member 320 can be similar or identical to the number of openings 124 discussed above with respect to spine member 120. With reference to at least FIG. 5C, edge member 316, edge member 318, and spine member 320 can include narrowing portions 316a, 318a, 320a that can be identical to narrowing portions 116a, 118a, 120a discussed above with respect to edge member 116, edge member 118, and spine member 120 (respectively). In some implementations, strap 300a is identical to strap 100a except with respect to the stems 330 and channels 350 which are discussed further below. The number of openings 322, openings 324, and/or stems 330 can be similar or identical to the number of openings 122, openings 124, and/or stems 130 discussed above with respect to base 110a.

Base 310a can comprise a pliable (for example, stretchable) material. In some implementations, base 310a only comprises one material, and such material can be pliable (for example, stretchable). For example, 310a can comprise an elastomeric material, such as rubber and/or silicone. In some implementations, base 310a does not comprise a metallic material.

Figure 5A:
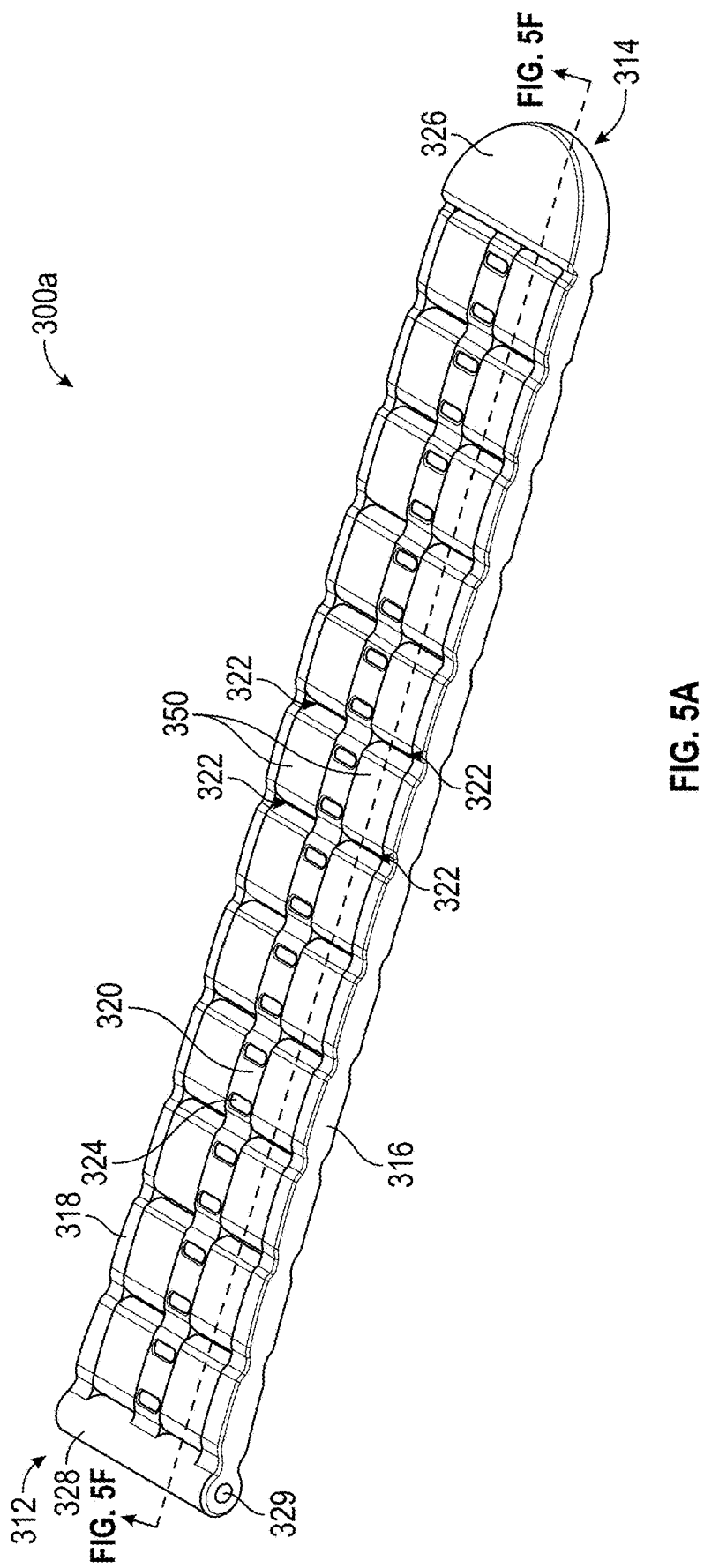
FIG. 5A illustrates a top perspective view of a strap in accordance with aspects of this disclosure.
Figure 5B:
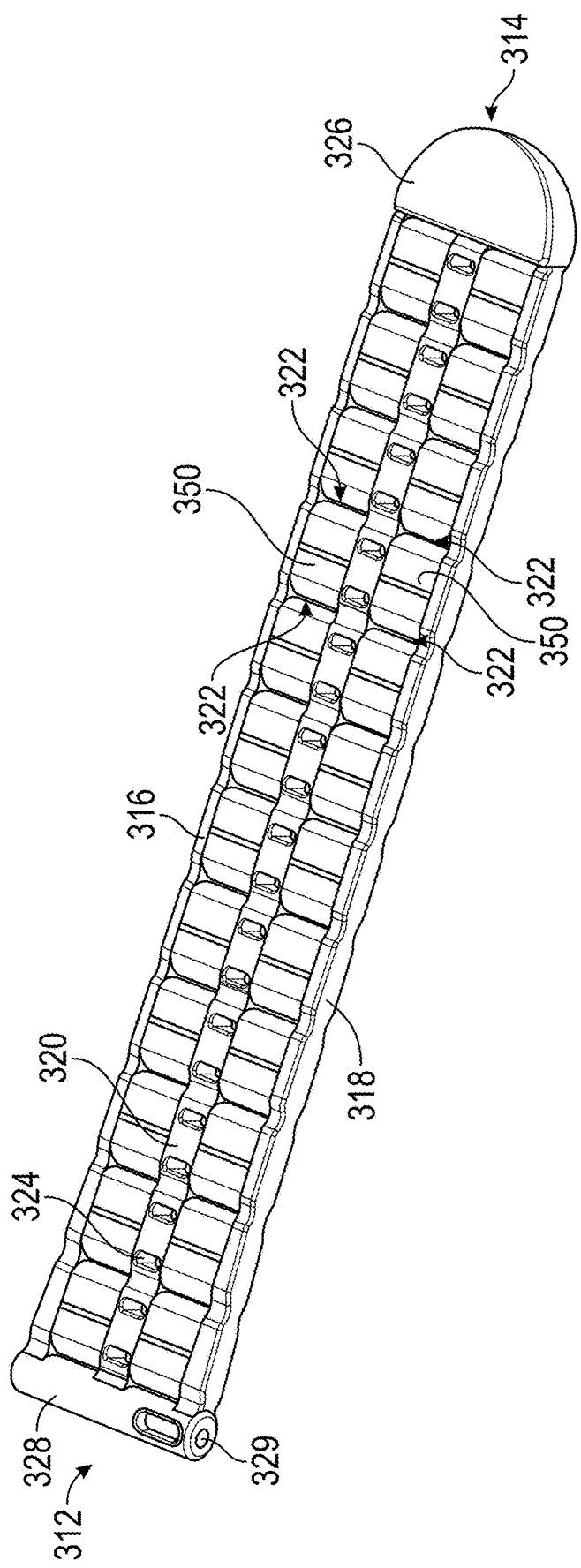
FIG. 5B illustrates a bottom perspective view of the strap of FIG. 5A in accordance with aspects of this disclosure.
Figure 5C:
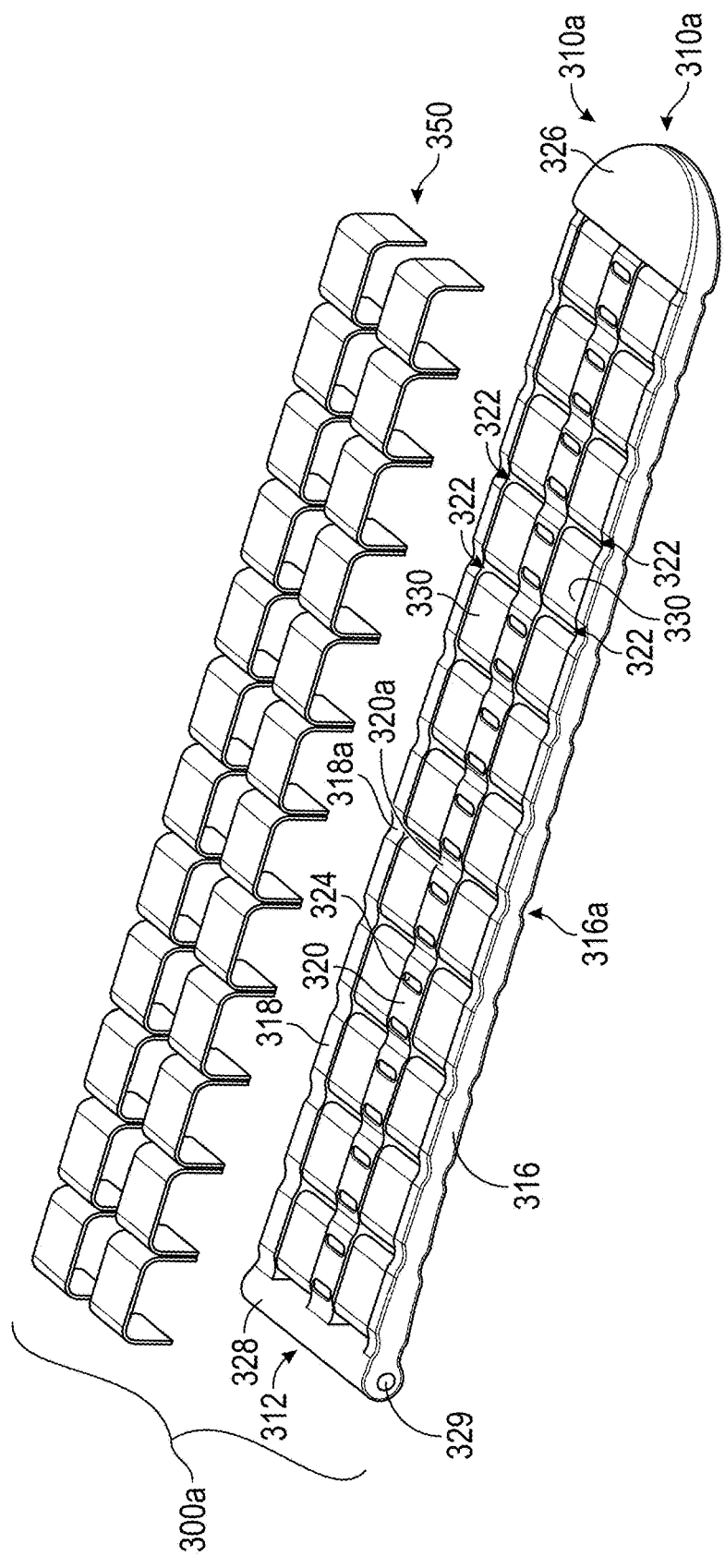
FIG. 5C illustrates an exploded perspective view of the strap of FIG. 5A in accordance with aspects of this disclosure.
Figure 5D:
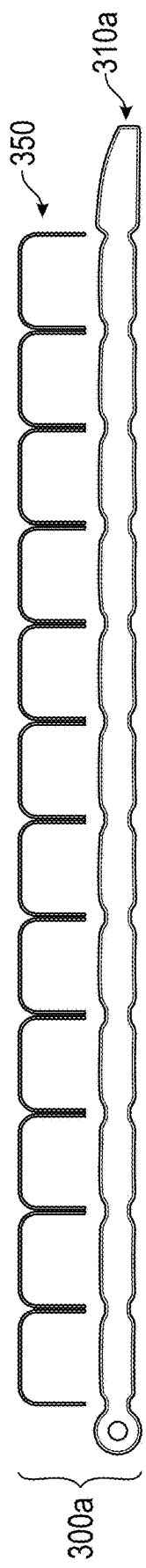
FIG. 5D illustrates an exploded side view of the strap of FIG. 5A in accordance with aspects of this disclosure.

Similar to strap 100a, strap 300a can include one or more or a plurality of stems 330. FIG. 5C-5D illustrate channels 350 detached (for example, disassembled) from base 310a. With reference to at least FIGS. 5G-5H, stem 330 can comprise a rounded cross-section. Stem 330 can comprise an oblong shape. Stem 330 can include a top portion 330a, a bottom portion 330b opposite the top portion 330a, and sides 330c, 330d. When the strap 300a is in use, for example when a wearable device 1 is secured to a user, bottom portion 330b can face toward skin of the wearer and/or be positioned closer to skin of the wearer than top portion 330a, and top portion 330a can face away from skin of the wearer and/or be positioned farther from skin of the wearer than bottom portion 330b.

Channel 350 can include a web 350a and one or more legs extending from web 350a. For example, channel 350 can include one or both of legs 350b, 350c that can extend from web 350a. Legs 350b, 350c can extend transverse (for example, perpendicular to) web 350a. Legs 350b, 350c can extend from ends of web 350a, for example, opposing ends of web 350a. In some implementations, web 350a comprises a greater length than one or both of legs 350b, 350c. Alternatively, in some implementations, web 350a has an equal or smaller length than one or both of legs 350b, 350c. In some implementations, web 350a is substantially planar.

Channel 350 can comprise a metallic material, such as stainless steel. In some implementations, channel 350 only comprises a metallic material. In some implementations, channel 350 does not comprise an elastomeric material. For example, in some implementations, channel 350 does not comprise rubber and/or do not comprise silicone. In some implementations, channel 350 does not comprise leather and/or do not comprise fabric.

Figure 5E:
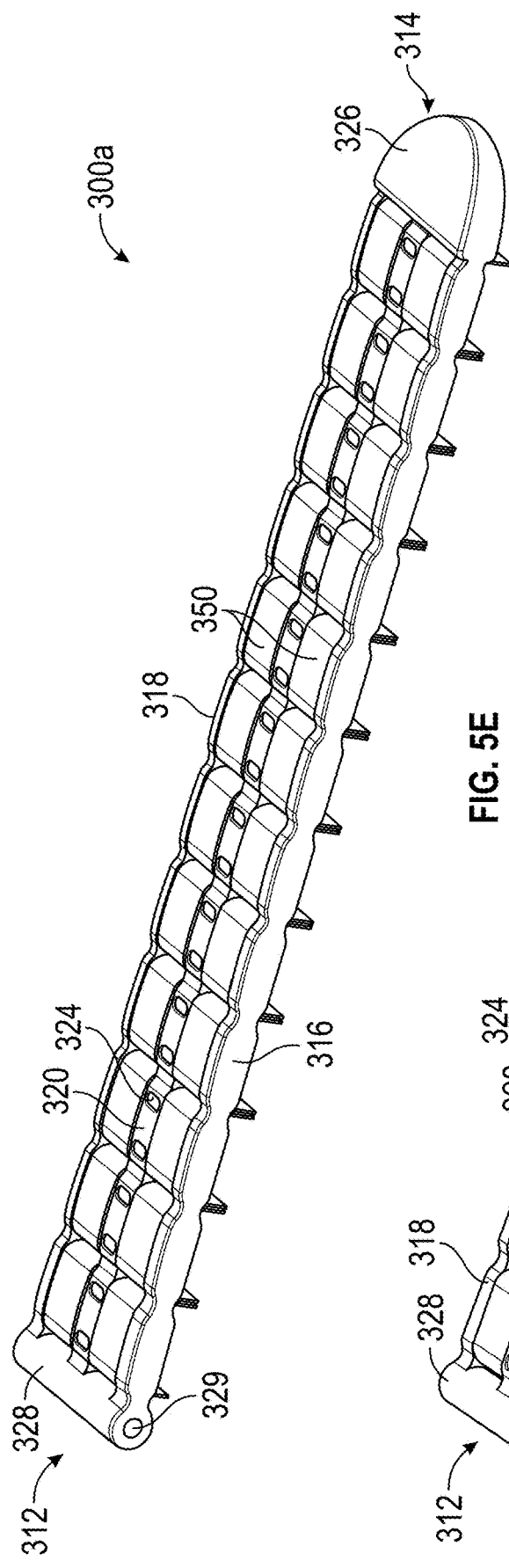
FIG. 5E illustrates a perspective view of the strap of FIG. 5A in a partially assembled state in accordance with aspects of this disclosure.
Figure 5F:
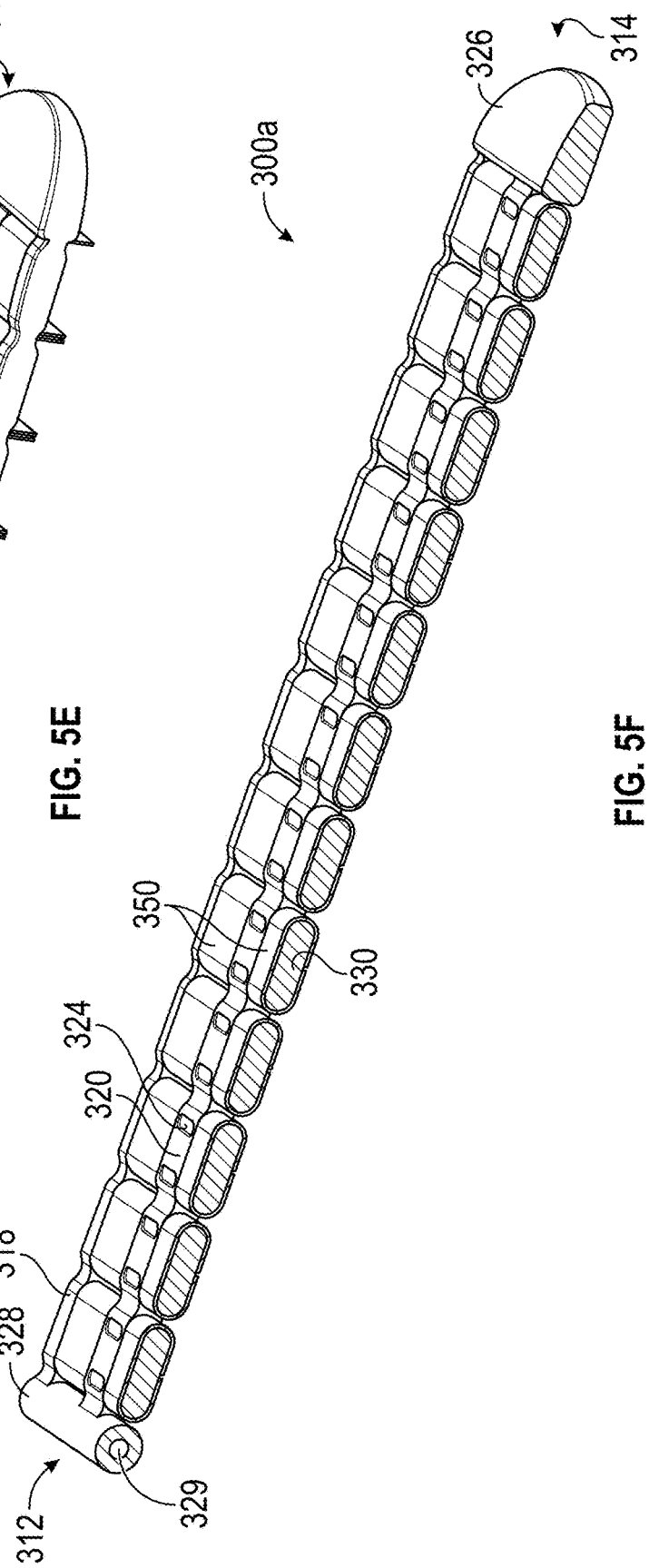
FIG. 5F a perspective view of a cross-section taken through the strap of FIG. 5A in accordance with aspects of this disclosure.
Figure 5G:
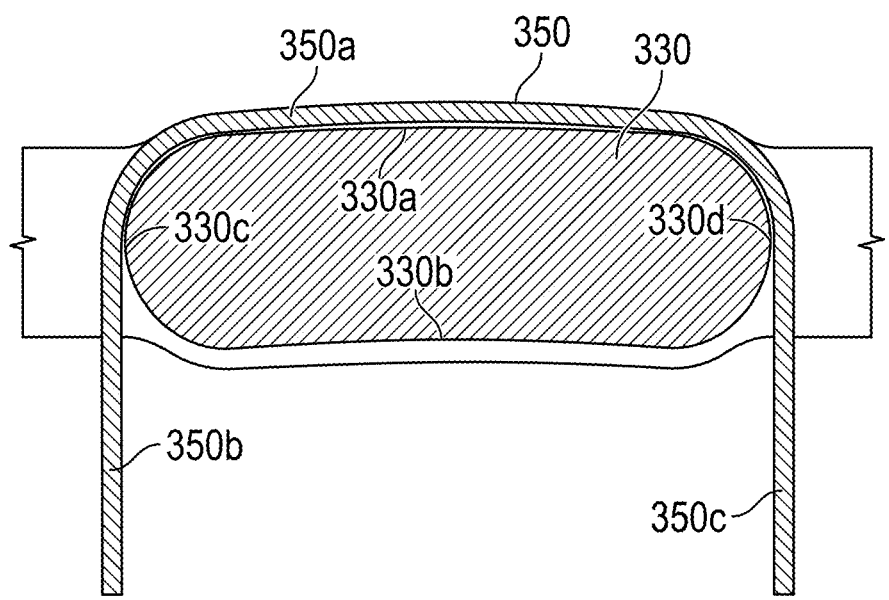
FIGS. 5G-5H illustrate enlarged cross-sectional views of portions of the strap of FIG. 5A in accordance with aspects of this disclosure.
Figure 5H:
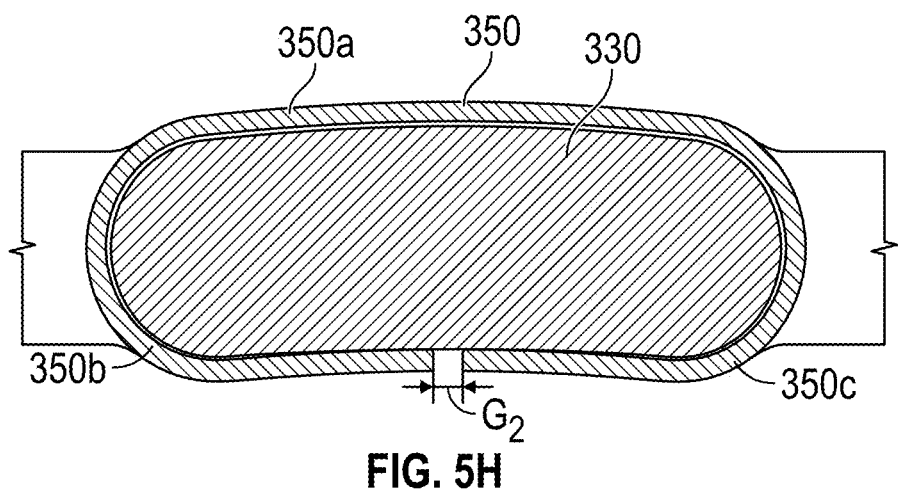

Channels 350 can be secured to base 310a in a variety of ways. Channels 350 can be secured over stems 330 by inserting legs 350b, 350c at least partially through openings 322 of base 310a. FIGS. 5C-5D illustrates channels 350 positioned above the stems 330 (for example, prior to insertion of legs 350b, 350c through openings 322) and FIGS. 5E and 5G illustrate channels 350 and stems 330 after such insertion. In some implementations, after legs 350b, 350c are inserted through openings 322, legs 350b, 350c can be bent (for example, crimped) around the stems 330 as illustrated in FIGS. 5F and 5H. In some implementations, channel 350 is secured to stem so as to surround an entirety of a cross-section of stem 330. In some implementations, channel 350 is secured to stem so as to surround less than an entirety of a cross-section of stem 330, for example, such that a gap G2 exists between ends of legs 350b, 350c when secured around stem 330. In some implementations, channel 350 surrounds at least approximately 80%, at least approximately 85%, at least approximately 90%, or at least approximately 95% of a perimeter of a cross-section of stem 330 when secured to stem 330. Additionally or alternatively, in some implementations, channel 350 surrounds greater than approximately 80% but less than 100% of the cross-section of stem 330, greater than approximately 90% but less than 100% of the cross-section of stem 330, or greater than approximately 95% but less than 100% of the cross-section of stem 330. In some implementations, gap $G_2$ is less than approximately 0.5 inch, less than approximately 0.4 inch, less than approximately 0.3 inch, less than approximately 0.2 inch, less than approximately 0.1 inch, less than approximately 0.05 inch, less than approximately 0.01 inch, or less than approximately 0.005 inch, for example.

FIGS. 6A-6D illustrate a strap 400a. Strap 400a can be utilized with a wearable device 1 and/or a watch module 10 in a similar or identical manner as that described elsewhere herein with reference to strap 100a. Strap 400a can be similar or identical to strap 100a in some or many respects. With reference to at least FIGS. 6A-6B, strap 400a can include a base 410a (which may also be referred to as a "main body"), an end 412, an end 414 opposite end 412, a length extending between ends 412, 414, sides that can include and/or be defined by edge members 416, 418, a tip 426 at or near end 414, and/or a coupling portion 428 including an opening 429 at or near end 412. End 412, end 414, edge members 416, 218, tip 426, coupling portion 428, and/or opening 429 can be similar or identical to end 112, end 114, edge members 116, 118, tip 126, coupling portion 128, and/or opening 129 described above with reference to strap 100a. Base 410a can be similar or identical to base 110a in some or many respects. For example, base 410a can include one or more and/or a plurality of openings 422 that can be similar or identical to openings 122 discussed above with respect to base 110a. As another example, base 410a can include a spine member 420 which can be similar or identical to spine member 120 discussed above. Spine member 420 can include one or more of a plurality of openings 424 that can be similar or identical to openings 124, and the number of openings 424 in spine member 420 can be similar or identical to the number of openings 124 discussed above with respect to spine member 120. Edge member 416, edge member 418, and spine member 420 can include narrowing portions 416a, 418a, 420a that can be identical to narrowing portions 116a, 118a, 120a discussed above with respect to edge member 116, edge member 118, and spine member 120 (respectively). In some implementations, strap 400a is identical to strap 100a except with respect to the stems 430 and channels 450 which are discussed further below. The number of openings 422, openings 424, and/or stems 430 can be similar or identical to the number of openings 122, openings 124, and/or stems 130 discussed above with respect to base 110a.

Base 410a can comprise a pliable (for example, stretchable) material. In some implementations, base 410a only comprises one material, and such material can be pliable (for example, stretchable). For example, 410a can comprise an elastomeric material, such as rubber and/or silicone. In some implementations, base 410a does not comprise a metallic material.

Similar to strap 100a, strap 400a can include one or more or a plurality of stems 430. With reference to at least FIG. 6D, stem 430 can comprise a rounded cross-section. For example, stem 430 can comprise a rounded rectangular shape. Channel 450 can comprise a cross-section that corresponds to a cross-section of the stem 430. In some implementations, channel 450 comprises a rounded rectangular cross-section. Channel 450 can be tubular. Channel 450 can surround an entirety of a cross-section of stem 430.

Channel 450 can comprise a metallic material, such as stainless steel. In some implementations, channel 450 only comprises a metallic material. In some implementations, channel 450 does not comprise an elastomeric material. For example, in some implementations, channel 450 does not comprise rubber and/or do not comprise silicone. In some implementations, channel 450 does not comprise leather and/or do not comprise fabric.

Figure 6E:
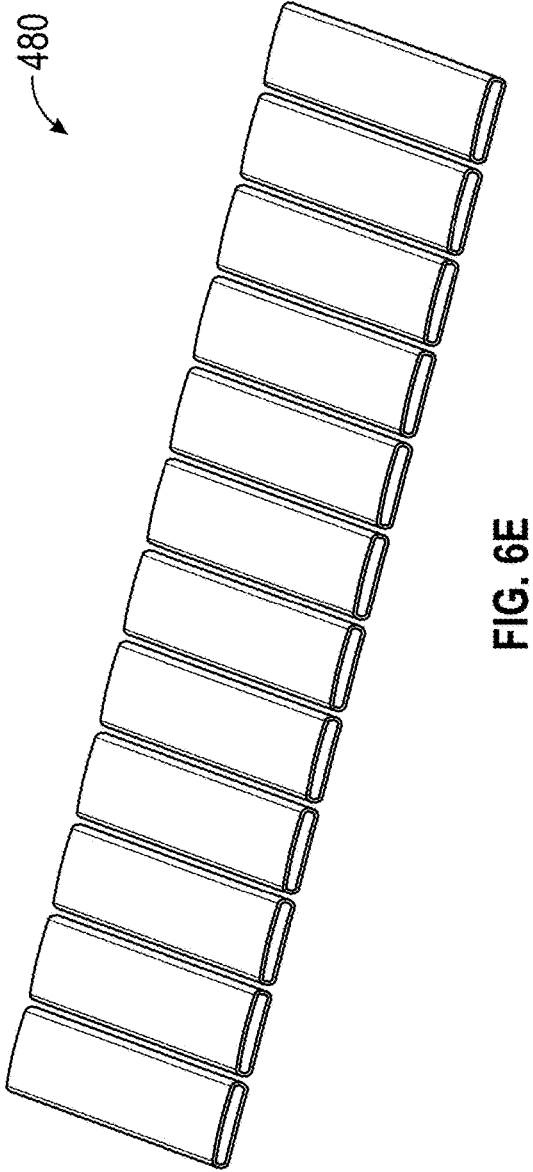
FIGS. 6E-6L illustrate an exemplary method of manufacturing the strap of FIG. 6A in accordance with aspects of this disclosure.
Figure 6F:
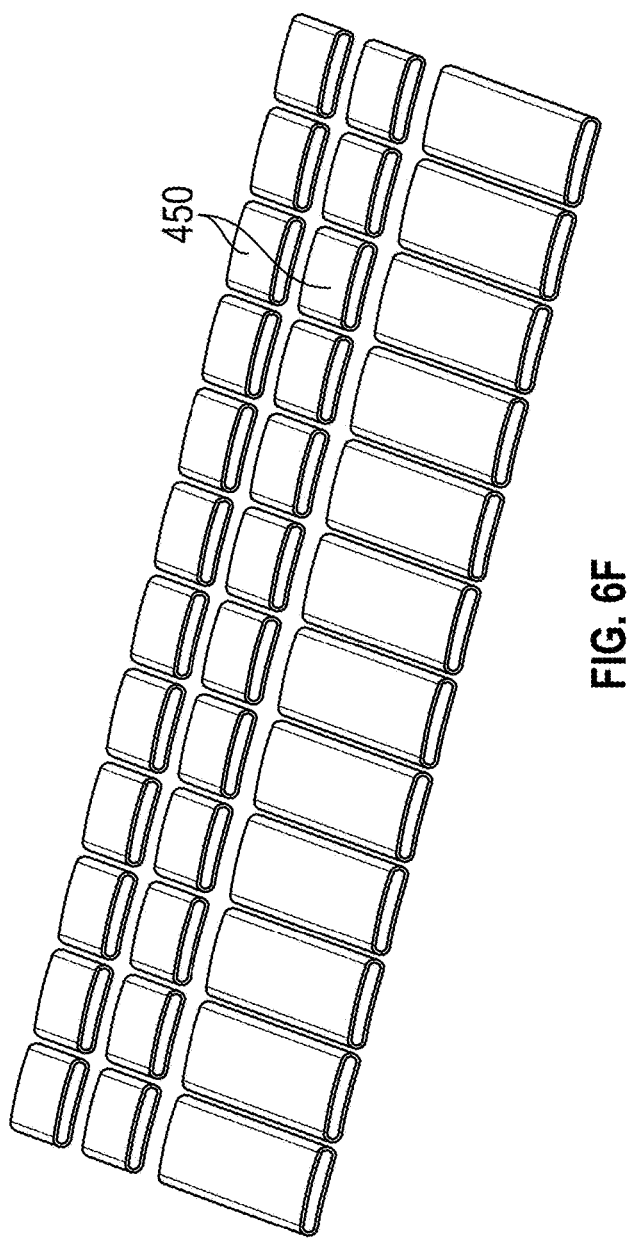

FIGS. 6E-6L illustrate an exemplary method of manufacturing strap 400a. With reference to FIG. 6E, one or more or a plurality of hollow tubes 480 can be obtained or formed (for example, via a metal extrusion process). In some implementations, tubes 480 are made of a metal or metallic material, for example stainless steel. In some implementations, tubes 480 only comprise a metallic material and do not comprise rubber, silicone, leather, and/or fabric. In some implementations, tubes 480 are formed to have a rounded cross-section, for example, a rounded rectangular cross-section. As illustrated in FIG. 6F, tubes 480 can be cut into shorter sections to form strap members, such as channels 450. In some implementations, all sharp edges of the tubes 480 are removed via deburring.

Figure 6G:
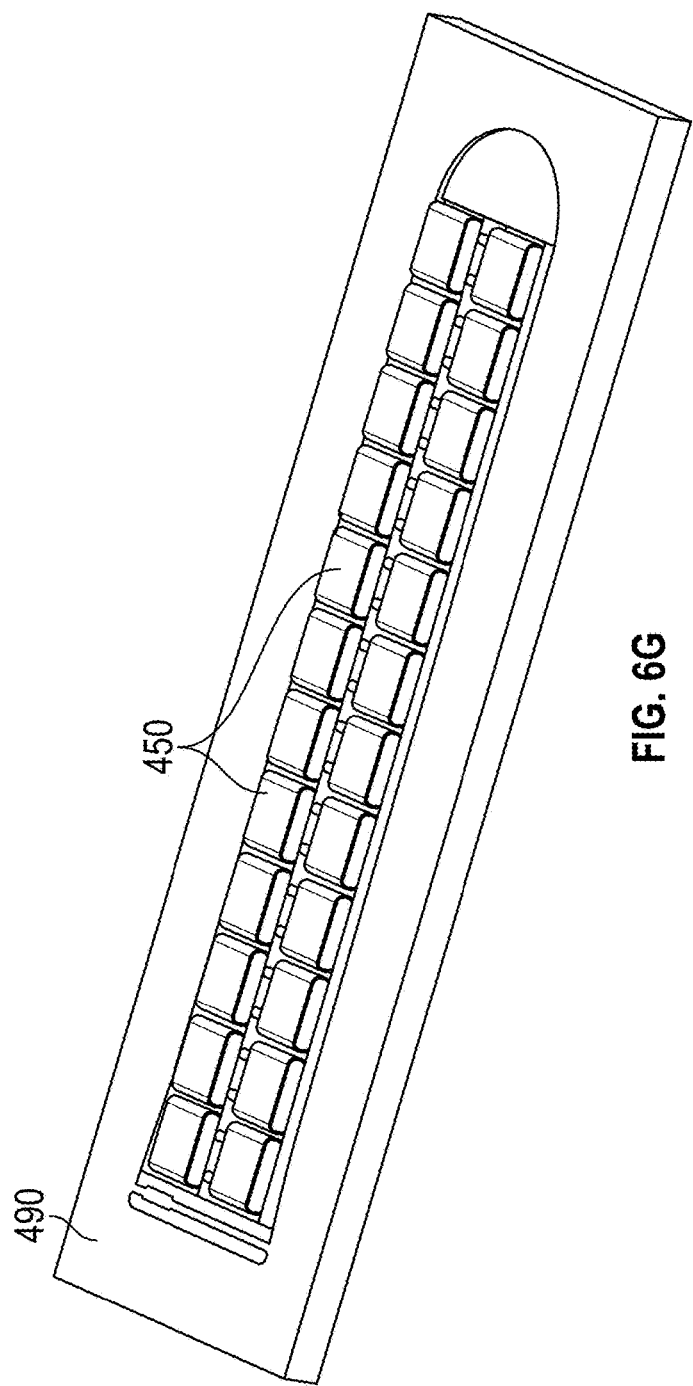
Figure 6H:
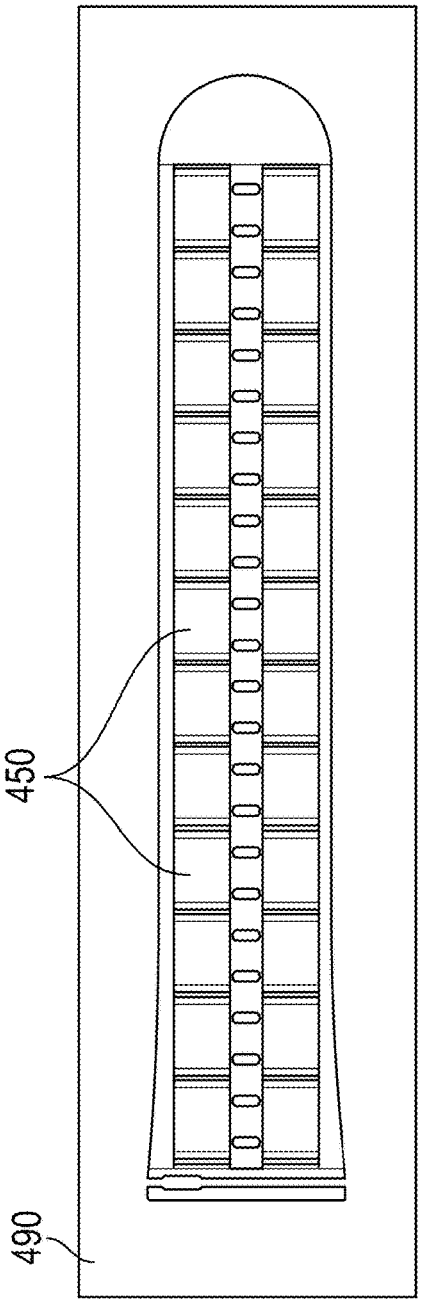
Figure 6I:
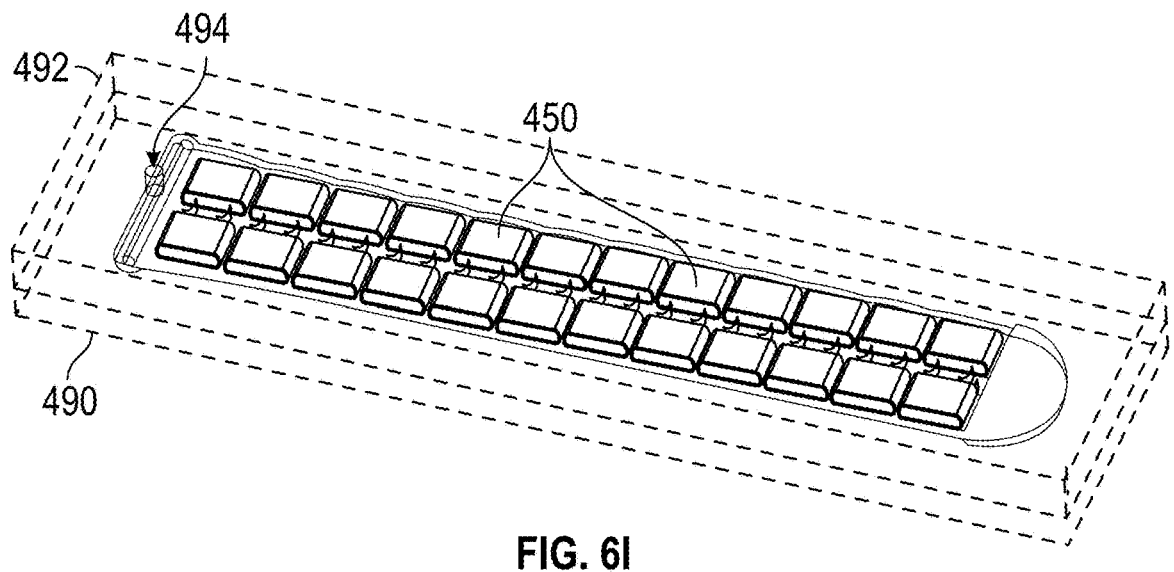
Figure 6J:
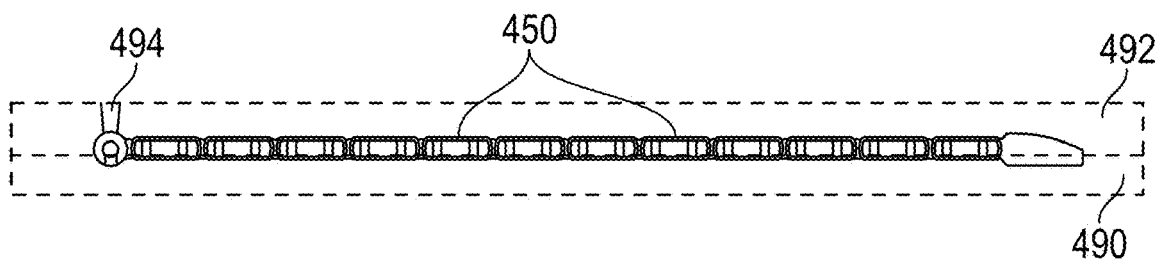
Figure 6K:
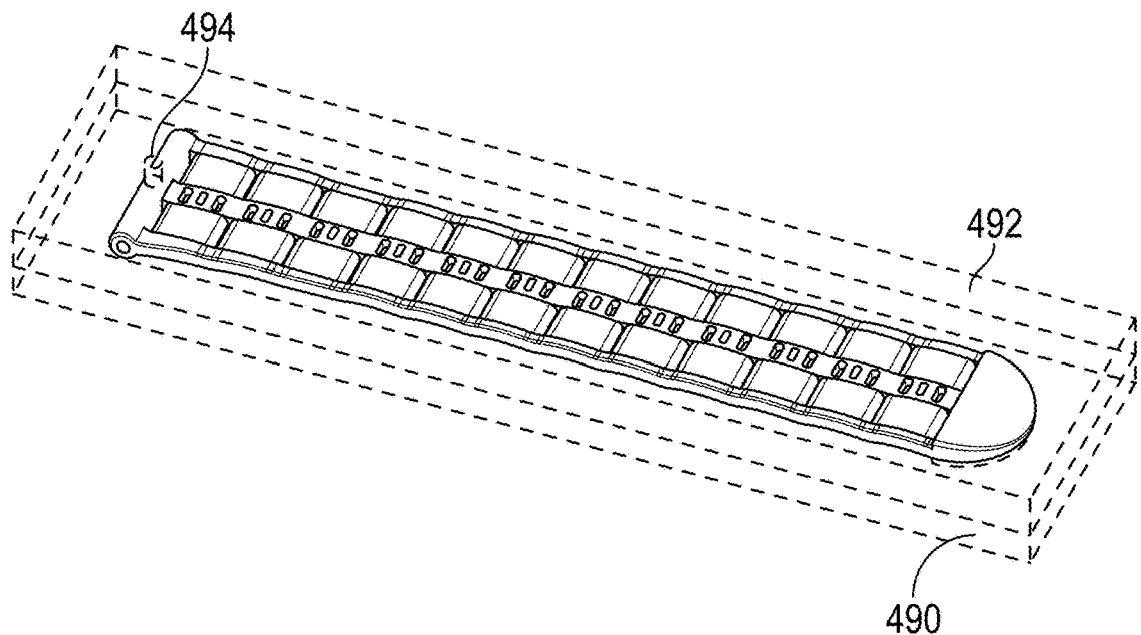
Figure 6L:
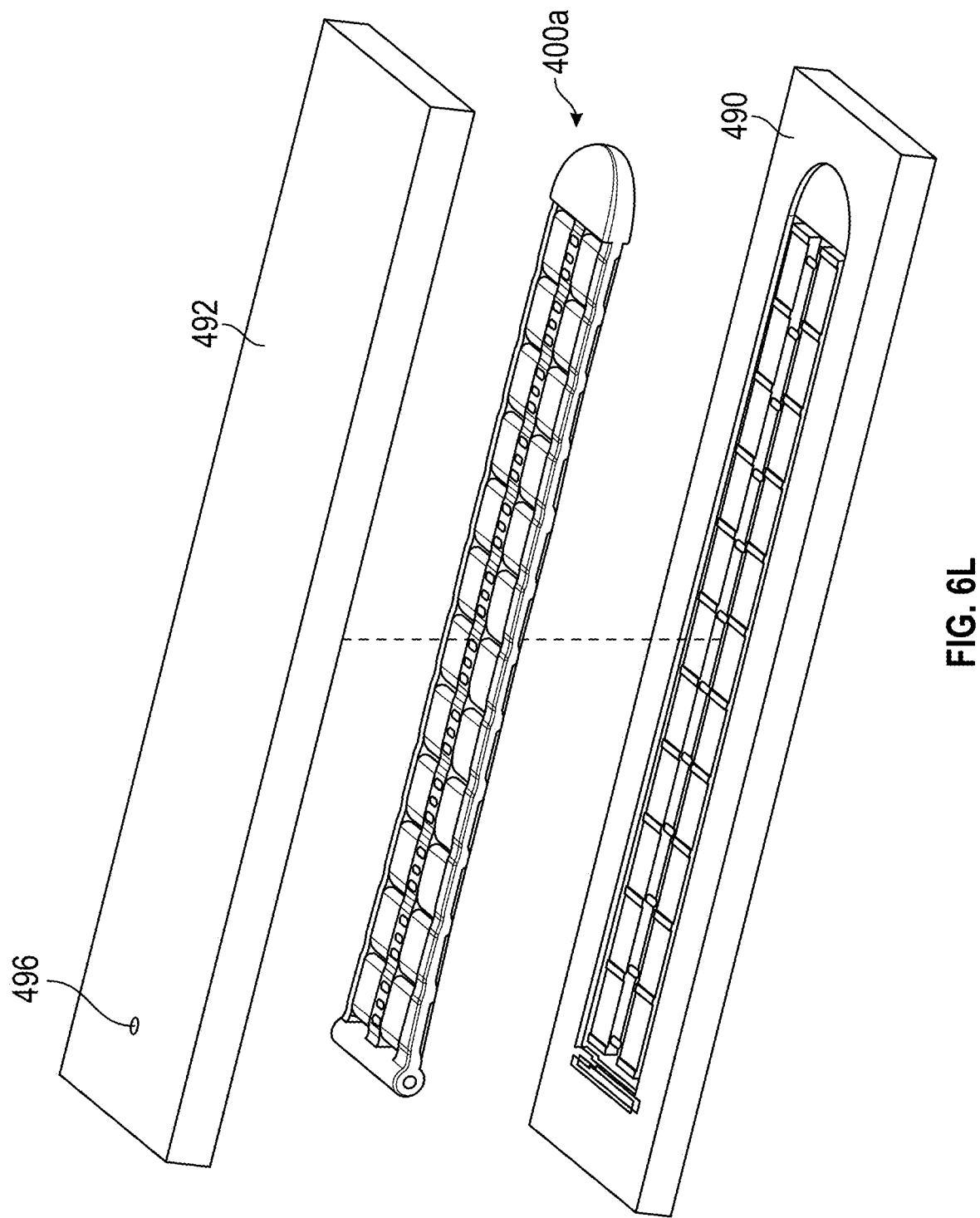

With reference to FIGS. 6G-6H, channels 450 can be arranged in a mold, for example a first mold portion 490. FIG. 6G illustrates a top perspective view of channels 450 in mold portion 490 and FIG. 6H illustrates a top view of channels 450 in mold portion 490. A second mold portion 492 can be positioned adjacent mold portion 490 to for an enclosed interior. In some implementations, mold portion 490 and/or 492 includes locations for each channel 450 arranged in multiple columns of multiple rows, and each of such location can be defined by walls or ribs in mold portion 490 and/or 492. In some implementations, mold portion 490 and/or 492 is configured to provide two columns and a plurality of rows within each column for receiving each of the channels 450. The number of columns and rows in the mold portion 490 and/or 492 can vary and correspond to the number of columns and rows of stems 430 and/or channels 450 for the strap 400a. The mold portion 490 and/or 492 can include one or more or a plurality of voids and/or portions configured to define portions of the base 410a of strap 400a after a material is inserted into the voids. For example, mold portion 490 and/or 492 can be configured to allow formation of (separately or together) any of the components discussed above with respect to base 410a.

After mold portions 490, 492 are assembled to form an enclosed interior that houses channels 450, a material can be inserted (for example, injected) into interior space defined by the mold portions 490, 492, for example, via an opening or port 492. The mold portions 490, 492 and/or channels 450 can be configured to allow such material to fill void spaces within the interior space and inside hollow portions of the channels 450. Such material can be a pliable material, for example, an elastomeric material including rubber and/or silicone. After the material cures, mold portions 490, 492 can be separated from each other and the finished strap 400a can be removed. Such finished strap 400a can include any of the features and/or components discussed above with respect to strap 400a.

Any of the straps described herein can be formed, at least in part, via a molding process with mold portions that can be similar or identical to mold portions 490, 492 in some or many respects. For example, any of the bases of the straps described herein can be formed via a molding process with mold portions that can be similar or identical to mold portions 490, 492 in some or many respects.

Additional Considerations and Terminology

Although this invention has been disclosed in the context of certain preferred embodiments, it should be understood that certain advantages, features and aspects of the systems, devices, and methods may be realized in a variety of other embodiments. Additionally, it is contemplated that various aspects and features described herein can be practiced separately, combined together, or substituted for one another, and that a variety of combination and subcombinations of the features and aspects can be made and still fall within the scope of the invention. Furthermore, the systems and devices described above need not include all of the modules and functions described in the preferred embodiments.

Conditional language used herein, such as, among others, "can," "could," "might," "may," "e.g.," and the like, unless specifically stated otherwise, or otherwise understood within the context as used, is generally intended to convey that certain features, elements, and/or steps are optional. Thus, such conditional language is not generally intended to imply that features, elements, and/or steps are in any way required or that one or more embodiments necessarily include logic for deciding, with or without other input or prompting, whether these features, elements, and/or steps are included or are to be always performed. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 10 degrees, 5 degrees, 3 degrees, or 1 degree. As another example, in certain embodiments, the terms "generally perpendicular" and "substantially perpendicular" refer to a value, amount, or characteristic that departs from exactly perpendicular by less than or equal to 10 degrees, 5 degrees, 3 degrees, or 1 degree.

Although certain embodiments and examples have been described herein, it will be understood by those skilled in the art that many aspects of the systems and devices shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Any methods disclosed herein need not be performed in the order recited. The methods disclosed herein may include certain actions taken by a practitioner; however, they can also include any third-party instruction of those actions, either expressly or by implication.

The methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, and/or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. The computer system may be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (for example, not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

Various illustrative logical blocks, modules, routines, and algorithm steps that may be described in connection with the disclosure herein can be implemented as electronic hardware (e.g., ASICs or FPGA devices), computer software that runs on general purpose computer hardware, or combinations of both. Various illustrative components, blocks, and steps may be described herein generally in terms of their functionality. Whether such functionality is implemented as specialized hardware versus software running on general-purpose hardware depends upon the particular application and design constraints imposed on the overall system. The described functionality can be implemented in varying ways for each particular application, but such implementation decisions should not be interpreted as causing a departure from the scope of the disclosure.

Moreover, various illustrative logical blocks and modules that may be described in connection with the disclosure herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. A processor can include an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of any method, process, routine, or algorithm described in connection with the disclosure herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features, it can be understood that various omissions, substitutions, and changes in the form and details of the devices or algorithms illustrated can be made without departing from the spirit of the disclosure. As can be recognized, certain portions of the description herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A strap for a wearable device configured to secure to a wrist of a user, the wearable device configured to measure one or more physiological parameters of the user, the strap comprising:
   a base comprising an integral structure made of a first material, the base further comprising:
      a first end configured to connect to a portion of the wearable device;
      a second end opposite the first end;
      a length extending between the first and second ends, wherein the base is configured to bend along the length to allow the strap to wrap around at least a portion of the user's wrist when in use;
      a width extending between opposite sides of the base;
      a plurality of openings spaced from one another along the length; and
      a plurality of stems, each of the plurality of stems positioned between two of said plurality of openings and extending generally in a direction of the width; and
   a plurality of pairs of channels positioned around the plurality of stems, each of the plurality of pairs of channels comprising:

a first channel positioned partially around one of the plurality of stems such that the first channel surrounds less than an entirety of the one of the plurality of stems, wherein the first channel comprises a second material; and a second channel positioned partially around the one of the plurality of stems such that the second channel surrounds less than said entirety of the one of the plurality of stems, wherein the second channel comprises the second material;

wherein the first and second channels are secured to one another around the one of the plurality of stems such that portions of the first and second channels overlap one another;

wherein the second material of the first and second channels is less pliable than the first material of the base.

2. The strap of claim 1, wherein the first material comprises stainless steel.

3. The strap of claim 1, wherein the second material comprises at least one of silicone and rubber.

4. The strap of claim 1, wherein:
the first channel comprises a web and legs extending from opposite ends of the web of the first channel;
the second channel comprises a web and legs extending from opposite ends of the web of the second channel; and
the legs of the first channel overlap the legs of the second channel.

5. The strap of claim 4, wherein the webs of the first and second channels do not overlap one another.

6. The strap of claim 4, wherein the webs of the first and second channels are generally planar and wherein the legs of the first and second channels are curved.

7. The strap of claim 4, wherein the legs of the first channel overlap only the legs of the second channel.

8. The strap of claim 4, wherein:
the one of the plurality of stems comprises a top portion, a bottom portion opposite the top portion, and opposing sides connecting the top and bottom portions;
the sides of the one of the plurality of stems are positioned adjacent the legs of the second channel; and
the overlapping legs of the first and second channels, non-overlapping portions of the first and second channels, and the sides of the one of the plurality of stems cooperate to define a generally rounded shape around the one of the plurality of stems.

9. The strap of claim 8, wherein:
the legs of the second channel contact the sides of the one of the plurality of stems; and
the sides of the one of the plurality of stems are configured such that at least a portion of an outer surface of each of the legs of the second channel is substantially flush with a plane of the top portion of the one of the plurality of stems.

10. The strap of claim 1, wherein:
the base further comprises:
a first edge member at least partially defining a first side of the base between the first and second ends;
a second edge member at least partially defining a second side of the base between the first and second ends, said second side being opposite said first side; and
a spine member extending along at least a portion of the length and positioned between the first and second edge members, wherein the spine member is generally parallel to the first and second edge members; and the plurality of openings comprises:
a first plurality of openings spaced from one another along at least a portion of the length and extending between the first edge member and the spine member; and
a second plurality of openings spaced from one another along at least a portion of the length and extending between the second edge member and the spine member; and the plurality of stems comprises:
a first plurality of stems, each of the first plurality of stems positioned between two of said first plurality of openings and extending between the first edge member and the spine member; and
a second plurality of stems, each of the second plurality of stems positioned between two of said second plurality of openings and extending between the second edge member and the spine member.

11. A wearable device comprising the strap of claim 1, wherein the wearable device is configured to measure at least one of oxygen saturation and pulse rate of the user.

12. A strap for a wearable device configured to secure to a wrist of a user, the strap comprising:
a base comprising an integral structure made of a first material, the base further comprising:
a first end configured to connect to a portion of the wearable device;
a second end opposite the first end;
a length extending between the first and second ends;
a width extending between opposite sides of the base;
a plurality of openings spaced from one another along the length; and
a plurality of stems, each of the plurality of stems positioned between two of said plurality of openings and extending generally in a direction of the width; and a plurality of pairs of channels positioned around the plurality of stems, each of the plurality of pairs of channels comprising:
a first channel positioned at least partially around one of the plurality of stems; and
a second channel positioned at least partially around the one of the plurality of stems and secured to the first channel;
wherein the first and second channels comprise a second material that is less pliable than the first material of the base.

13. The strap of claim 12, wherein the first material comprises a metallic material and wherein the second material comprises at least one of silicone and rubber.

14. The strap of claim 12, wherein the first and second channels are not integral with one another.

15. The strap of claim 12, wherein:
the first channel comprises a web and legs extending from opposite ends of the web of the first channel;
the second channel comprises a web and legs extending from opposite ends of the web of the second channel; and
the legs of the first channel overlap the legs of the second channel.

16. The strap of claim 15, wherein the webs of the first and second channels do not overlap one another.

17. The strap of claim 15, wherein:

the one of the plurality of stems comprises a top portion, a bottom portion opposite the top portion, and opposing sides connecting the top and bottom portions;

the sides of the one of the plurality of stems contact the legs of the second channel;

the legs of the second channel are sandwiched between the sides of the one of the plurality of stems and the legs of the first channel; and the overlapping legs of the first and second channels, non-overlapping portions of the first and second channels, and the sides of the one of the plurality of stems cooperate to define a generally rounded shape around the one of the plurality of stems.

18. A strap for a wearable device configured to secure to a portion of a user's body, the strap comprising:

a base comprising a first material, the base further comprising:

a first end, a second end opposite the first end, and a length extending between the first and second ends;

a plurality of openings spaced from one another along the length; and a plurality of stems, each of the plurality of stems positioned between two of said plurality of openings; and a plurality of strap members positioned around the plurality of stems and comprising a second material that is less pliable than the first material.

19. The strap of claim 18, wherein the first material comprises a metallic material and wherein the second material comprises at least one of silicone and rubber.

20. The strap of claim 18, wherein the plurality of strap members comprises a plurality of pairs of channels positioned around the plurality of stems, each of the plurality of pairs of channels comprising:

a first channel positioned partially around one of the plurality of stems such that the first channel surrounds less than an entirety of the one of the plurality of stems; and a second channel positioned partially around the one of the plurality of stems such that the second channel surrounds less than said entirety of the one of the plurality of stems;

wherein the first and second channels are secured to one another around the one of the plurality of stems such that portions of the first and second channels overlap one another.

\* \* \* \* \*